(12) United States Patent
Givoly et al.

(10) Patent No.: US 10,109,374 B1
(45) Date of Patent: Oct. 23, 2018

(54) METHODS AND SYSTEMS AND COMPUTER PROGRAM FOR PROVIDING PERSONALIZED MEDICAL INFORMATION

(71) Applicant: Medivizor International Limited, Road Town, Tortola (VG)

(72) Inventors: Tal Givoly, Irvine, CA (US); Oren Fuerst, Newark, DE (US)

(73) Assignee: Medivizor International Limited, Road Town, Tortola (VG)

( * ) Notice: Subject to any disclaimer, the term of this patent is extended or adjusted under 35 U.S.C. 154(b) by 380 days.

(21) Appl. No.: 13/732,982

(22) Filed: Jan. 2, 2013

(51) Int. Cl.
   *G16H 10/60* (2018.01)
   *G06F 17/30* (2006.01)
   *G06F 19/00* (2018.01)

(52) U.S. Cl.
   CPC ....... *G16H 10/60* (2018.01); *G06F 17/30522* (2013.01); *G06F 19/322* (2013.01)

(58) Field of Classification Search
   CPC ........ G06Q 50/22; G06Q 50/24; G16H 10/60; G06F 17/30522; G06F 19/322
   See application file for complete search history.

(56) References Cited

U.S. PATENT DOCUMENTS

| | | | | |
|---|---|---|---|---|
| 8,412,542 B2* | 4/2013 | Mok | ..................... | G06F 19/322 705/2 |
| 8,639,226 B2* | 1/2014 | Hutchings et al. | ........ | 455/414.1 |
| 8,706,530 B2* | 4/2014 | Ohnemus et al. | ................ | 705/3 |
| 8,732,240 B1* | 5/2014 | Tomkins | ........... | G06F 17/30041 709/204 |
| 2013/0080266 A1* | 3/2013 | Molyneux | .............. | G06Q 10/00 705/14.72 |
| 2014/0004492 A1* | 1/2014 | O'Reilly et al. | .............. | 434/236 |

* cited by examiner

*Primary Examiner* — Eliza A Lam
(74) *Attorney, Agent, or Firm* — Greenberg Traurig, LLP

(57) ABSTRACT

A computer-implemented method that includes receiving, by a computer system, current medical data from at least one electronic source; identifying, by the computer system, at least one medical-related filtering criterion related to an individual or a group of individuals; filtering, by the computer system, the current medical data based, at least in part, on at least one medical-related filtering criterion to identify current personalized medical data, where the current personalized medical data is related to the individual or the group of individuals; and presenting, by the computer system, the current personalized medical data to the individual or the group of individuals.

14 Claims, 87 Drawing Sheets

| | | | |
|---|---|---|---|
| Medivizor (with Logo) | | | News* | Sign In | Help |
| Sign Up | | | |
| Basic Information | Nickname | davidk | (why?) |
| * Mandatory Fields | Gender* | ● Male ○ Female | (why?) |
| | Age (Month/Year of Birth)* | Sep ▼ 1973 ▼ | (why?) |
| | Ethnicity | Unspecified ▼ | (why?) |
| | Primary residence | USA ▼ 95814 ▼ | (why?) |
| Conditions | | L 🔍 + | |
| | | Lactose Intolerance | |
| | | Leukemia | |
| | | Leukemia in Children | |
| | | Liver Cancer | |
| | | Liver Failure | |
| | | Lung Cancer | |
| Treatments | | begin typing a treatment here 🔍 + | |

About Medivizor | Contact | Privacy Policy
© copyright 2012

Notes:
Medical Conditions is an example of how additional medical data about the individual will be entered. The same type of interface would be for Treatments and Medical Professionals with the appropriate natural changes.

Fig. 9

High-level Architecture

Fig. 67
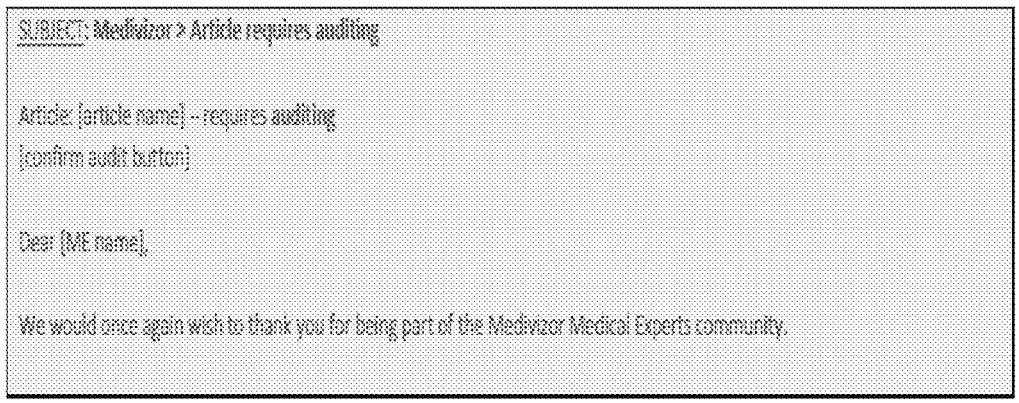
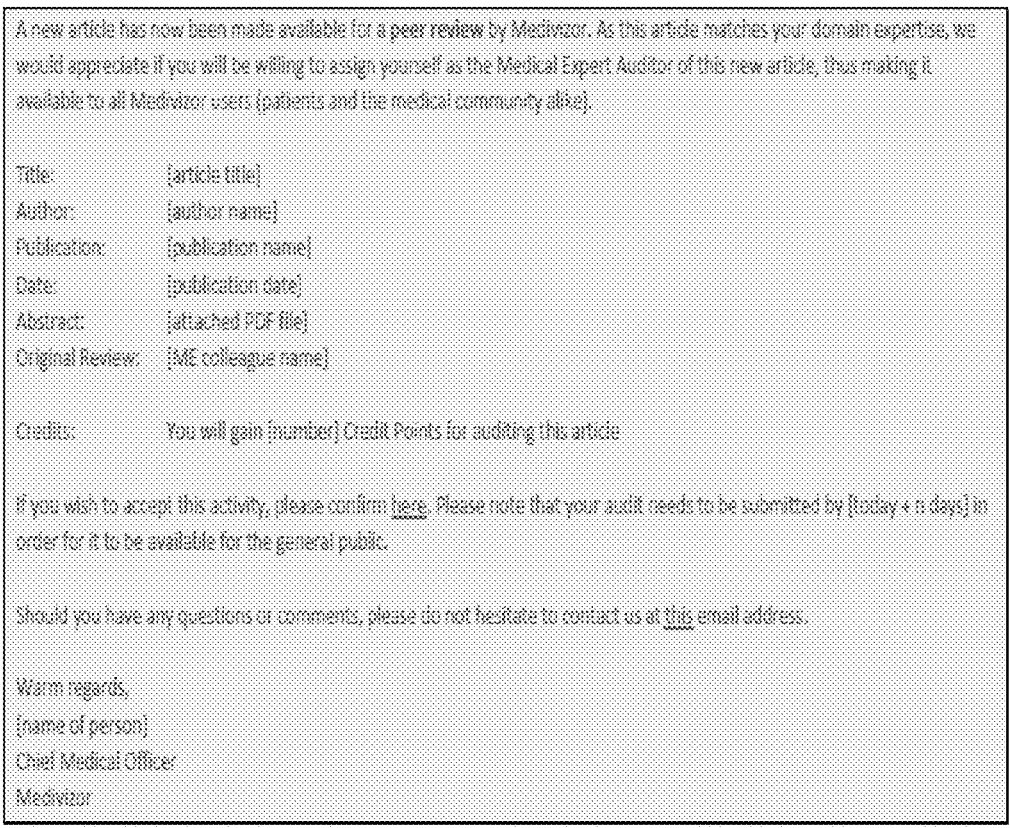
The here visible link & button above would open an automatically generated email. The ME only needs to 'send' the email (without changing its subject or body). This email is used by the automated Medivizor system. The email would contain the relevant information linking it to the ME and mentioned article.

Fig. 68
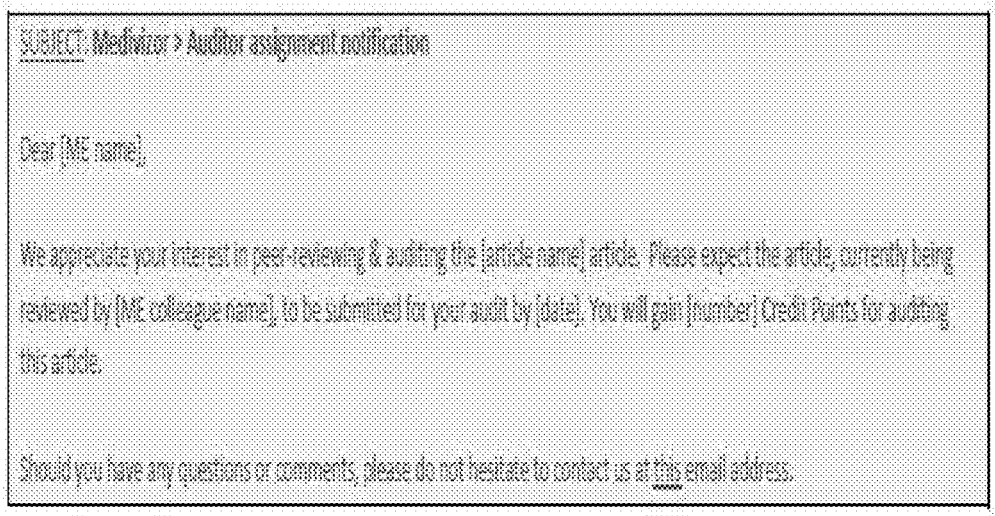
In case the Me Auditor was identified prior to the Me Reviewer, the text above would be modified to say "We will soon provide further information as to when you will receive the article for auditing" instead of providing a clear date.

Fig. 70

SUBJECT: Medivizor > Article auditor guidelines

Article: [article name] – auditing guidelines
[login to Medivizor button]

Dear [ME name],

The article [article name], originally reviewed by [ME colleague name] is now ready to be peer-reviewed. This activity includes the following deliverables:

1. Condition Classification – relating the article to the specific conditions, including any associated treatments.
2. Layman's Summary – for the patient community
3. Professional Summary – for the medical community Attached you may find the following:

1. The article in PDF format (titled [file name])
2. A Word document for the Layman's and Professional summaries (titled [file name]) – this includes the original review summaries
3. Check list and tips (titled [file name])

Once you are ready to submit your work, please login to Medivizor. Please note that the Condition Classification auditing can only be done online, while auditing the summaries can be done offline and uploaded once done. You will gain [number] Credit Points for reviewing this article.

As a reminder, please note that your audit needs to be submitted by [today + n days] in order for it to be available for the general public.

Should you have any questions or comments, please do not hesitate to contact us at this email address.

Warm regards,
[name of person]
Chief Medical Officer
Medivizor

The login visible link & button above would open the Medivizor UI as described later on in this section. The ME will be required to re-enter his password to login.

Fig. 73

SUBJECT: Medivizor > Article editor guidelines

Article: [article name] – editor guidelines
[login to Medivizor button]

Dear [ME name],

Thank you for your willingness to edit the article [article name], originally reviewed by [ME Reviewer name] and then peer-reviewed by [ME Auditor name]. This activity includes the following deliverables:

1. Condition Classification – relating the article to the specific conditions, including any associated treatments
2. Layman's Summary – for the patient community
3. Professional Summary – for the medical community Attached you may find the following:

1. The article in PDF format (titled [file name])
2. A Word document for the Layman's and Professional summaries (titled [file name]) – this includes both the original review version and the peer reviewed one
3. Check list and tips (titled [file name])

Once you are ready to submit your work, please login to Medivizor. Please note that the Condition Classification auditing can only be done online, while auditing the summaries can be done offline and uploaded once done. You will gain [number] Credit Points for reviewing this article.

As a reminder, please note that your editing needs to be submitted by [today + n days] in order for it to be available for the general public.

Should you have any questions or comments, please do not hesitate to contact us at this email address.

Warm regards,
[name of person]
Chief Medical Officer
Medivizor

*The login visible link & button above would open the Medivizor UI as described later on in this section. The ME will be required to re-enter his password to login.*

METHODS AND SYSTEMS AND COMPUTER PROGRAM FOR PROVIDING PERSONALIZED MEDICAL INFORMATION

A portion of the disclosure of this patent document contains material which is subject to copyright protection. The copyright owner has no objection to the facsimile reproduction by anyone of the patent document or patent disclosure as it appears in the Patent and Trademark Office patent file or records, but otherwise reserves all copyright rights whatsoever.

TECHNICAL FIELD

The present invention relates to medical information systems.

BACKGROUND

Systems that provide medical information are known in the art.

SUMMARY OF INVENTION

In some embodiments, the computer-implemented method includes receiving, by a computer system, current medical data from at least one electronic source; identifying, by the computer system, at least one medical-related filtering criterion related to an individual or a group of individuals; filtering, by the computer system, the current medical data based, at least in part, on at least one medical-related filtering criterion to identify current personalized medical data, where the current personalized medical data is related to the individual or the group of individuals; and presenting, by the computer system, the current personalized medical data to the individual or the group of individuals.

In some embodiments, the computer-implemented method further includes comparing, by the computer system, the current personalized medical data to past personalized medical data to identify that the past personalized medical data is obsolete in view of the current personalized medical data; and notifying, by the computer system, the individual or the group of individuals that the past personalized medical data is obsolete.

In some embodiments, the computer-implemented method further includes receiving, by the computer system, data associated with an individual or a group of individuals; and filtering, by the computer system, the current medical data based, at least in part, on the data associated with the individual or the group of individuals.

In some embodiments, the current medical data that includes health-related information relevant to at least one health condition of the individual or at least one health condition of the group of individuals.

In some embodiments, the current medical data includes at least one social media posting.

In some embodiments, the at least one medical-related filtering criterion is selected from the group of a demographic criterion, a health condition criterion, and a medical treatment criterion.

In some embodiments, the computer-implemented method further includes determining, by the computer system, a degree of relevance of discrete information within the current personalized medical data based on relevance to the individual or the group of individuals; and presenting, by the computer system, the discrete information within the current personalized medical data to the individual or the group of individuals according to the degree of relevance.

In some embodiments, the computer system includes at least one specially programmed computer module for receiving current medical data from at least one electronic source; identifying, by the computer system, at least one medical-related filtering criterion related to an individual or a group of individuals; filtering, by the computer system, the current medical data based, at least in part, on at least one medical-related filtering criterion to identify current personalized medical data, where the current personalized medical data is related to the individual or the group of individuals; and presenting the current personalized medical data to the individual or the group of individuals.

In some embodiments, the computer system further includes comparing the current personalized medical data to past personalized medical data to identify that the past personalized medical data is obsolete in view of the current personalized medical data; and notifying the individual or the group of individuals that the past personalized medical data is obsolete.

In some embodiments, the current medical data comprises health-related information relevant to at least one health condition of the individual or at least one health condition of the group of individuals.

In some embodiments, the current medical data comprises at least one social media posting.

In some embodiments, the at least one medical-related filtering criterion is selected from the group of a demographic criterion, a health condition criterion, and a medical treatment criterion.

In some embodiments, the computer system further includes determining a degree of relevance of discrete information within the current personalized medical data based on relevance to the individual or the group of individuals; and presenting the discrete information within the current personalized medical data to the individual or the group of individuals according to the degree of relevance.

In some embodiments, the computer program product embodied on a non-transitory computer readable medium includes computer code for receiving current medical data from at least one electronic source; identifying, by the computer system, at least one medical-related filtering criterion related to an individual or a group of individuals; filtering, by the computer system, the current medical data based, at least in part, on at least one medical-related filtering criterion to identify current personalized medical data, where the current personalized medical data is related to the individual or the group of individuals; and presenting the current personalized medical data to the individual or the group of individuals.

In some embodiments, the computer program product that includes the computer code for comparing the current personalized medical data to past personalized medical data to identify that the past personalized medical data is obsolete in view of the current personalized medical data; and notifying the individual or the group of individuals that the past personalized medical data is obsolete.

In some embodiments, the current medical data comprises health-related information relevant to at least one health condition of the individual or at least one health condition of the group of individuals.

In some embodiments, the at least one medical-related filtering criterion is selected from the group of a demographic criterion, a health condition criterion, and a medical treatment criterion.

In some embodiments, the computer program product further includes the computer code for determining a degree of relevance of discrete information within the current personalized medical data based on relevance to the individual or the group of individuals; and presenting the discrete information within the current personalized medical data to the individual or the group of individuals according to the degree of relevance.

BRIEF DESCRIPTION OF THE DRAWINGS

Figure 1:
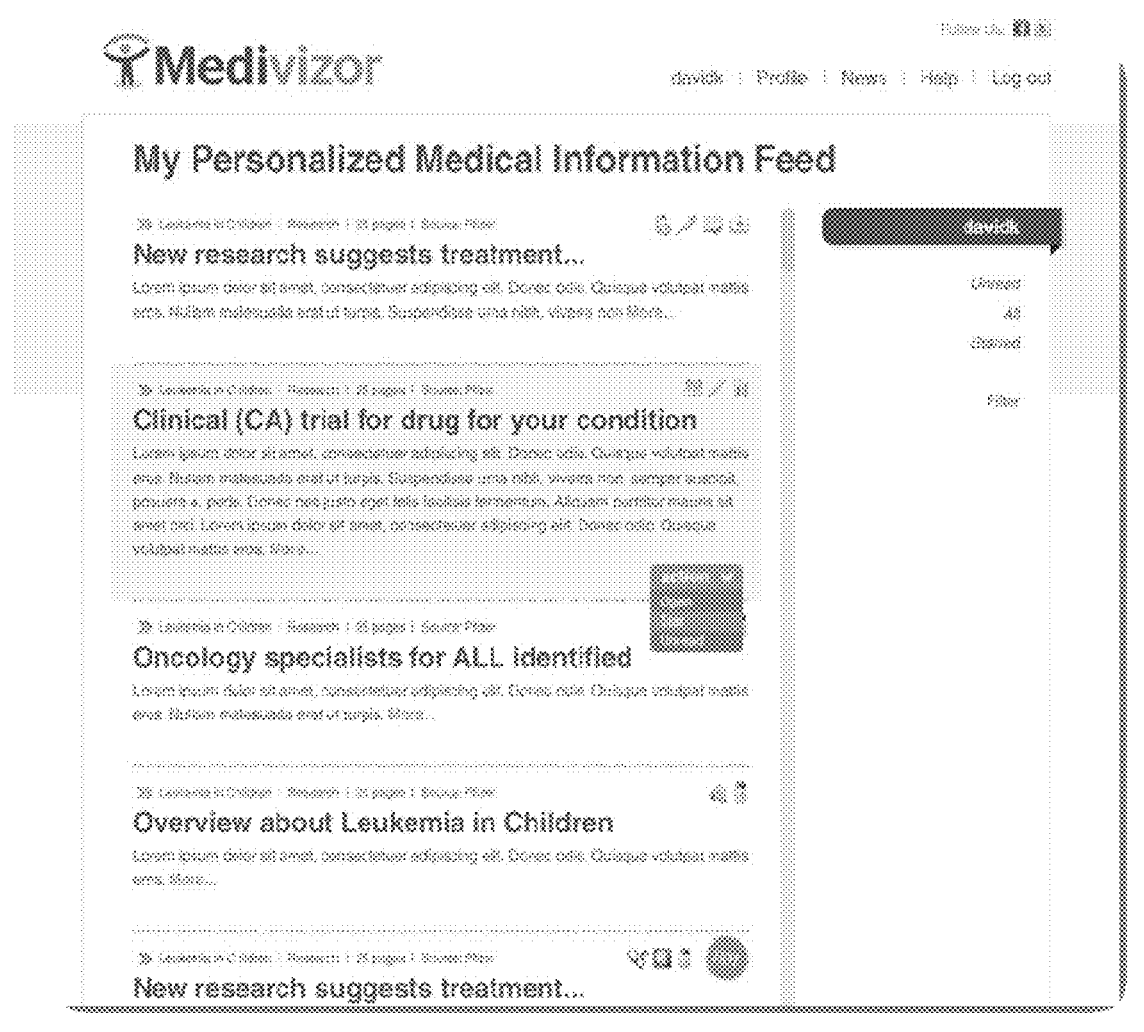

FIG. 1 illustrates features of some embodiments of the present invention.

Figure 4:
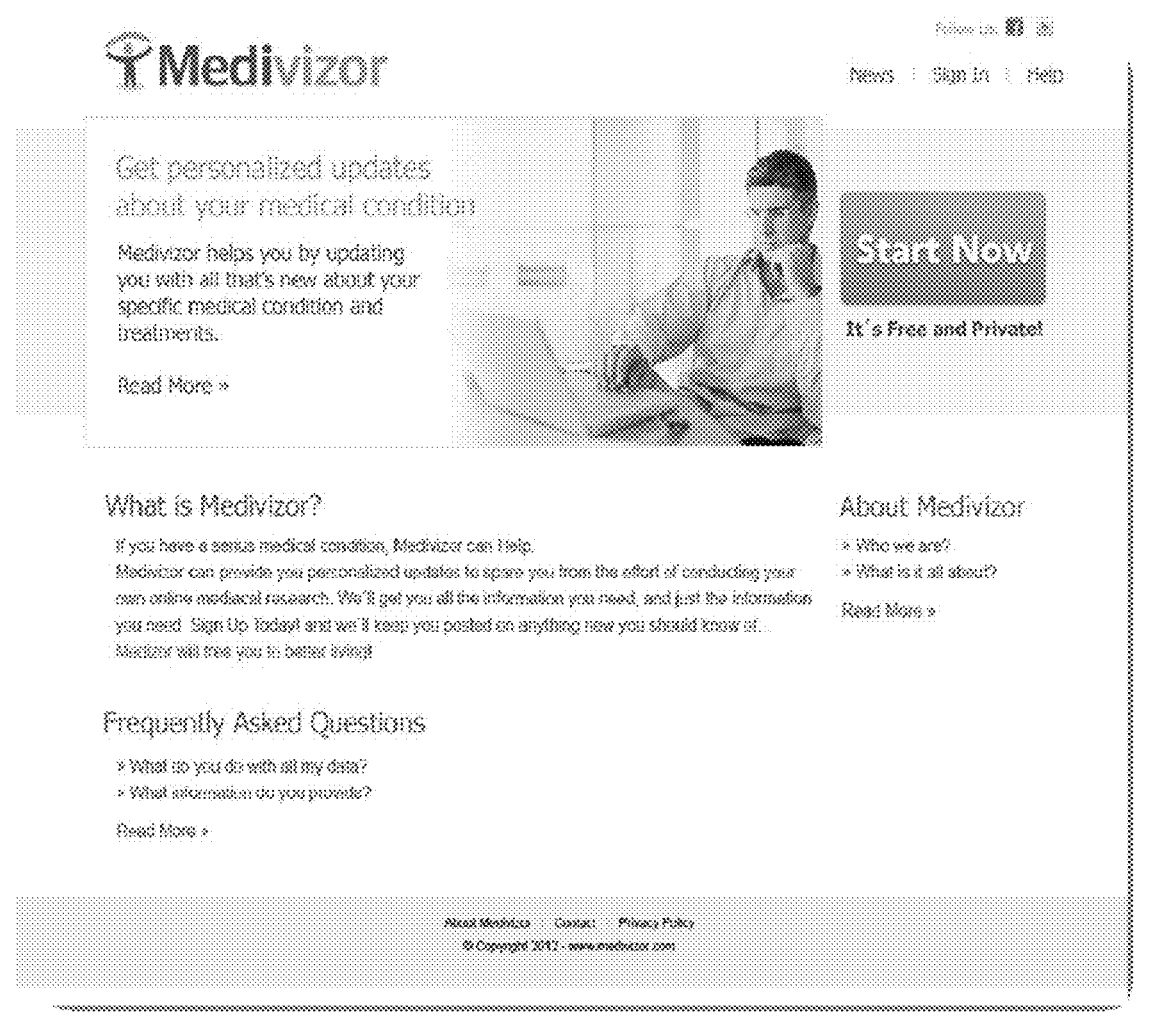

FIG. 4 illustrates features of some embodiments of the present invention.

FIG. 6 illustrates features of some embodiments of the present invention.

Figure 9:
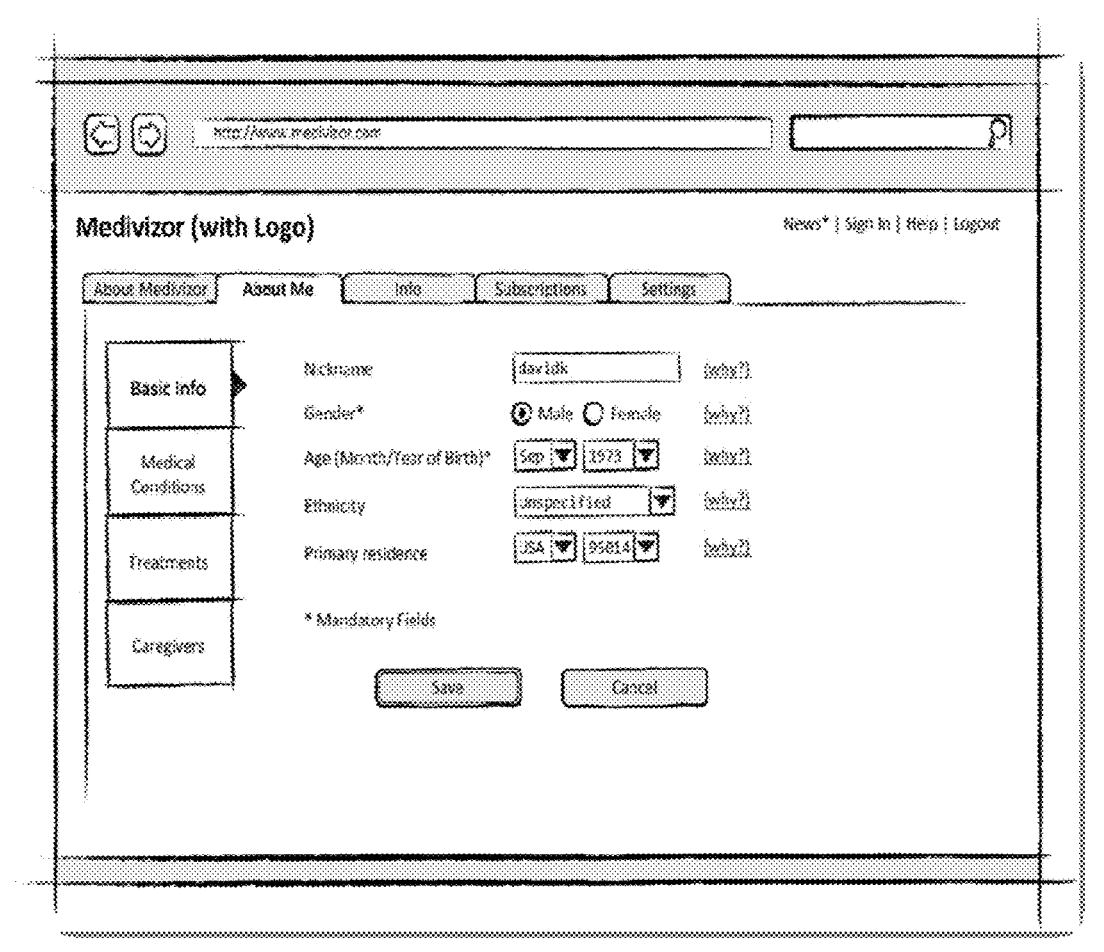

FIG. 9 illustrates features of some embodiments of the present invention.

FIG. 53 illustrates features of some embodiments of the present invention.

FIG. 54 illustrates features of some embodiments of the present invention.

FIG. 61 illustrates features of some embodiments of the present invention.

FIG. 64 illustrates features of some embodiments of the present invention.

FIG. 67 illustrates features of some embodiments of the present invention.

FIG. 68 illustrates features of some embodiments of the present invention.

FIG. 70 illustrates features of some embodiments of the present invention.

FIG. 73 illustrates features of some embodiments of the present invention.

FIG. 74 illustrates features of some embodiments of the present invention.

Figure 2:
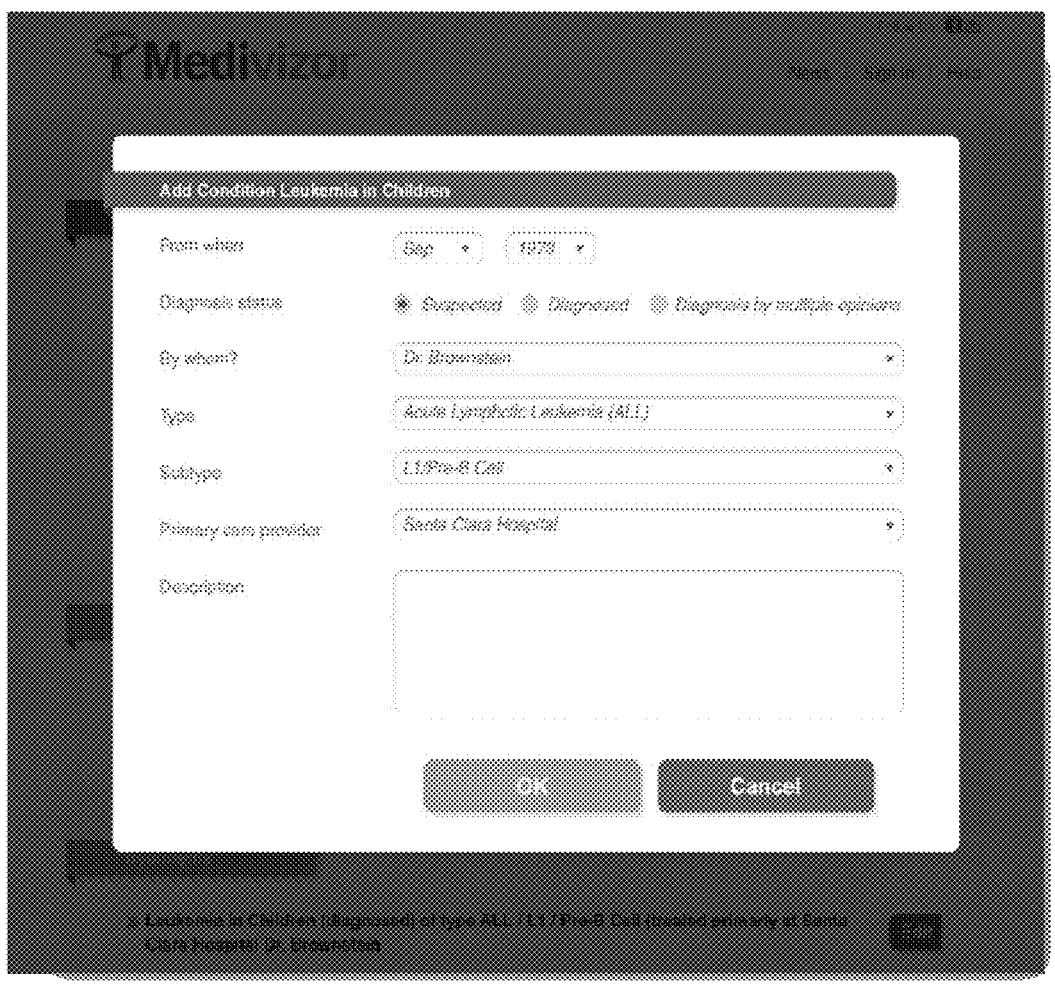
FIG. 2 illustrates features of some embodiments of the present invention.
Figure 3:
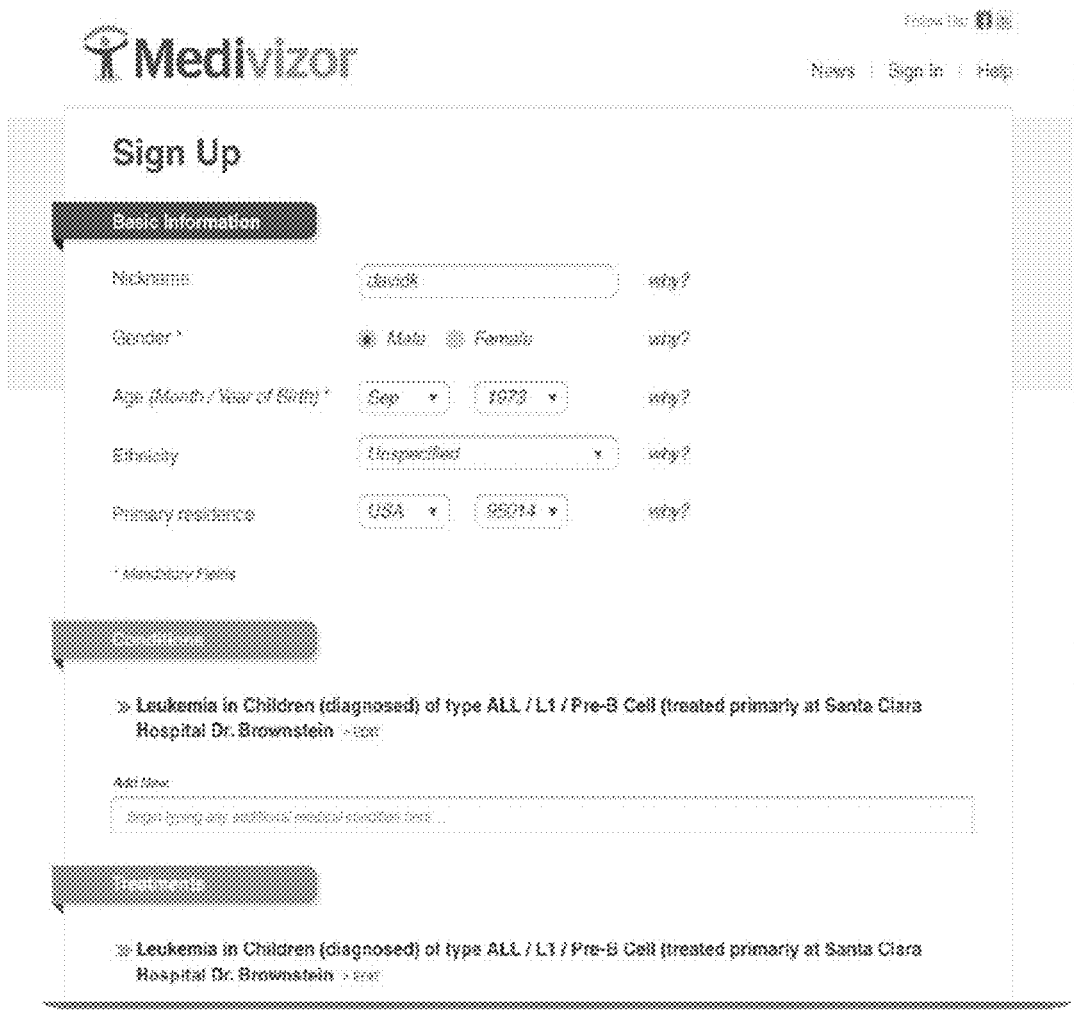
FIG. 3 illustrates features of some embodiments of the present invention.
Figure 5:
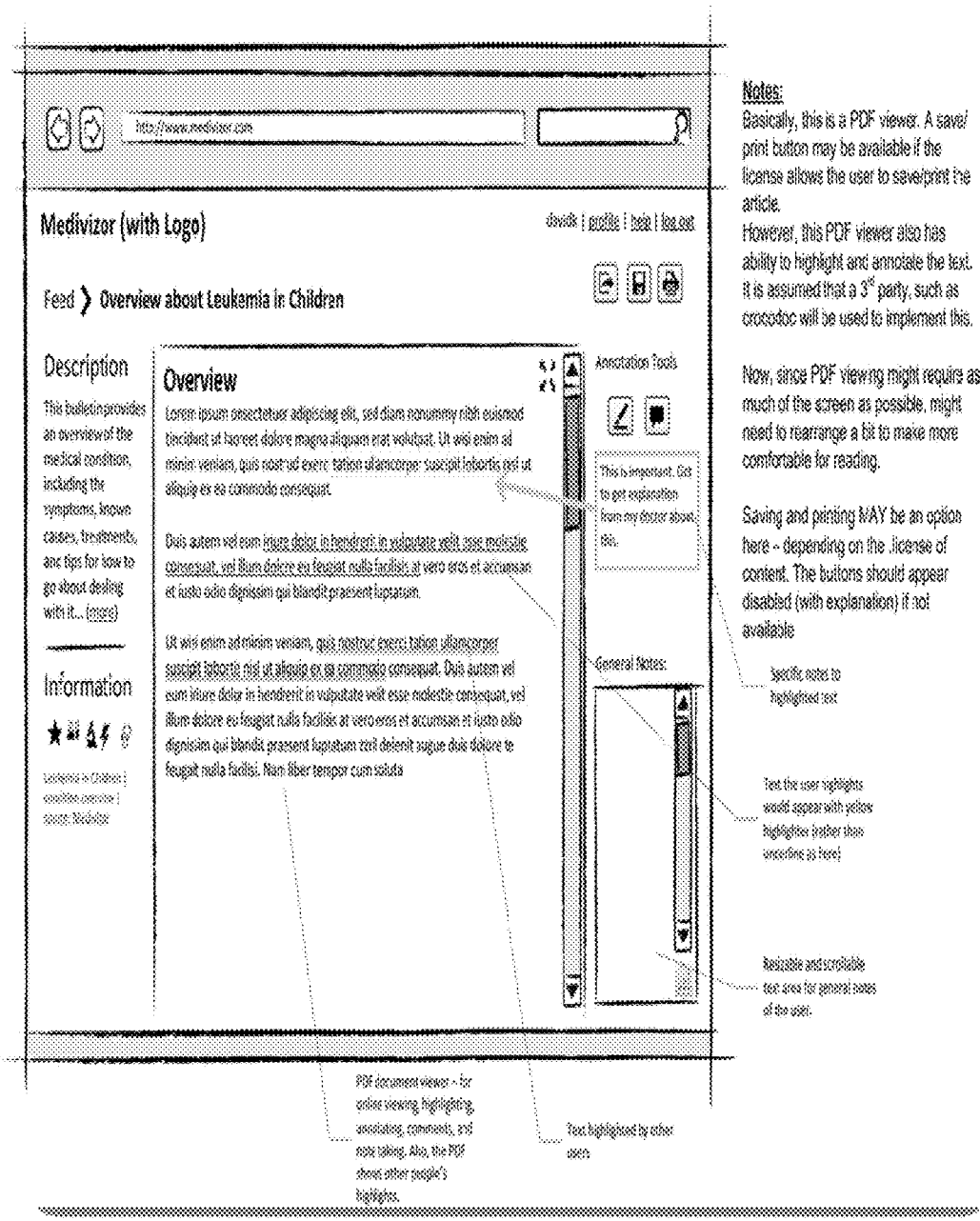
FIG. 5 illustrates features of some embodiments of the present invention.
Figure 7:
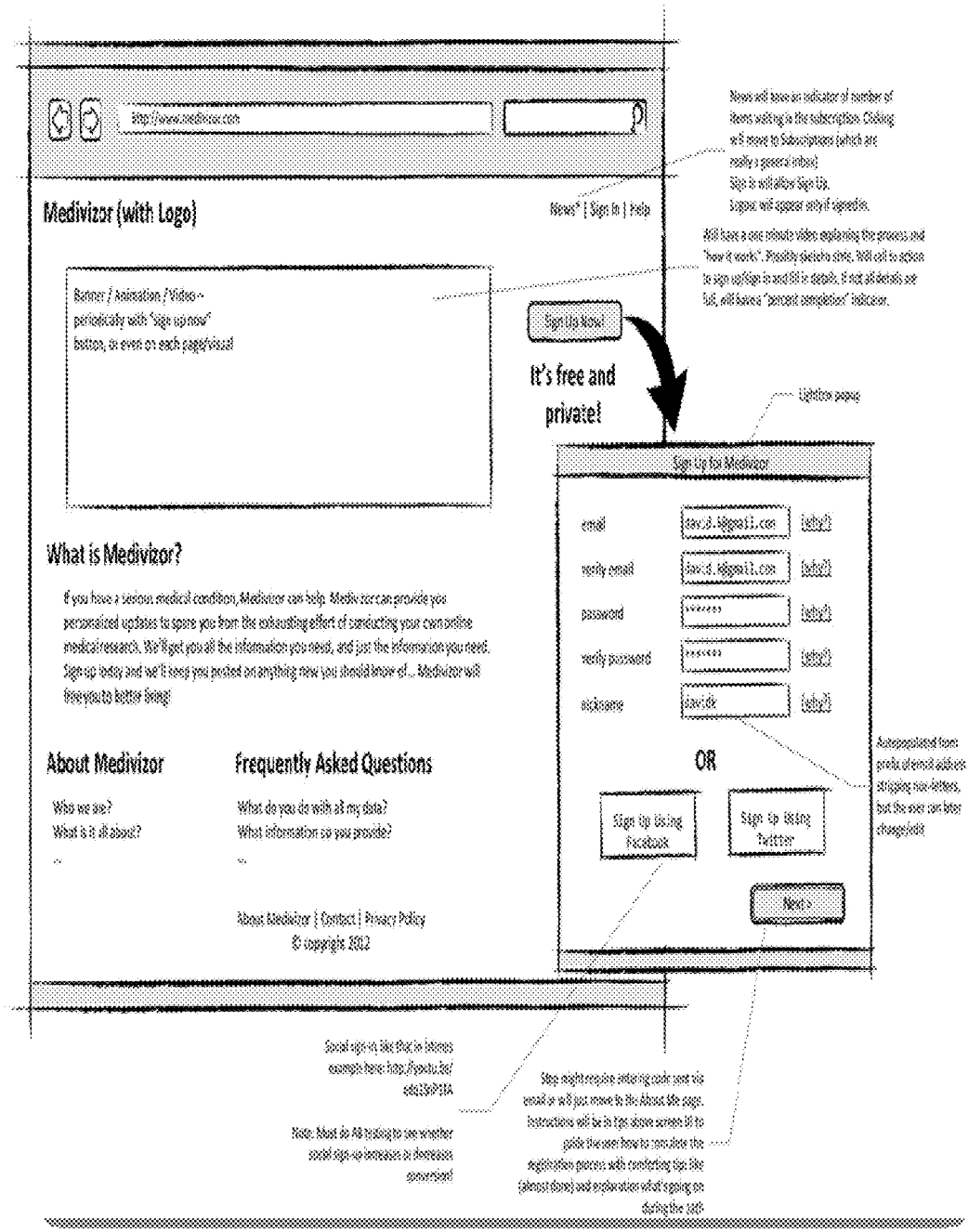
FIG. 7 illustrates features of some embodiments of the present invention.
Figure 8:
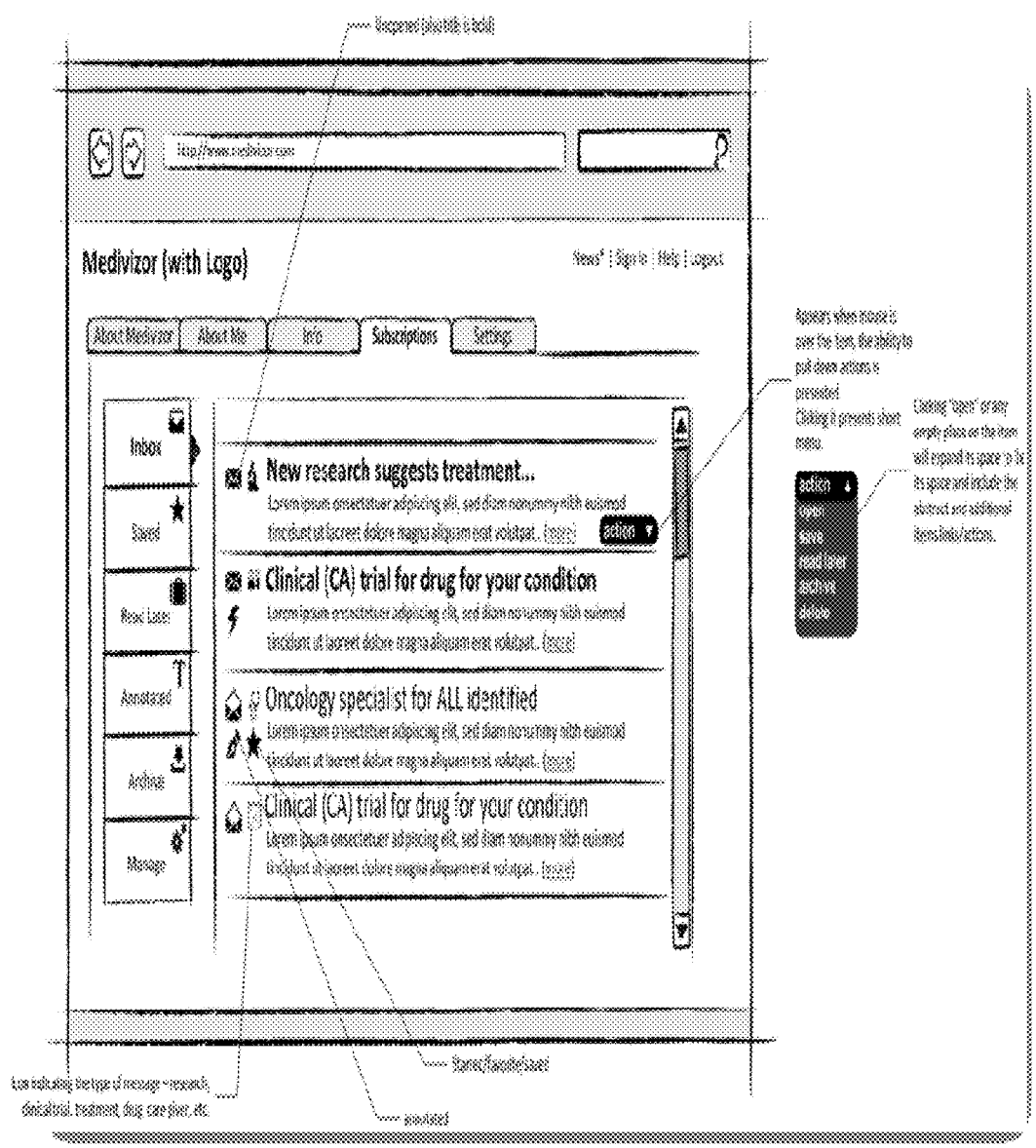
FIG. 8 illustrates features of some embodiments of the present invention.
Figure 10:
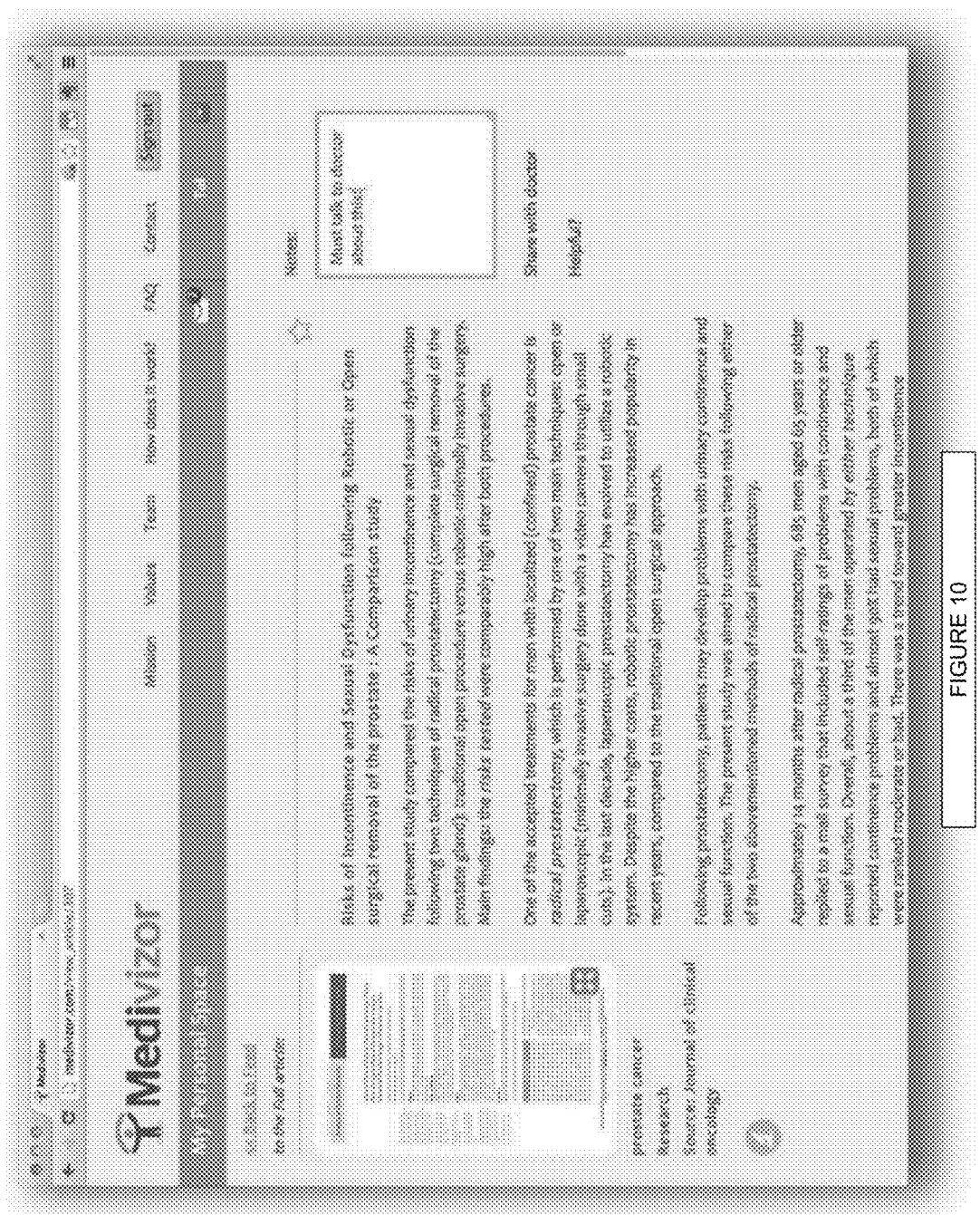
FIG. 10 illustrates features of some embodiments of the present invention.
Figure 11:
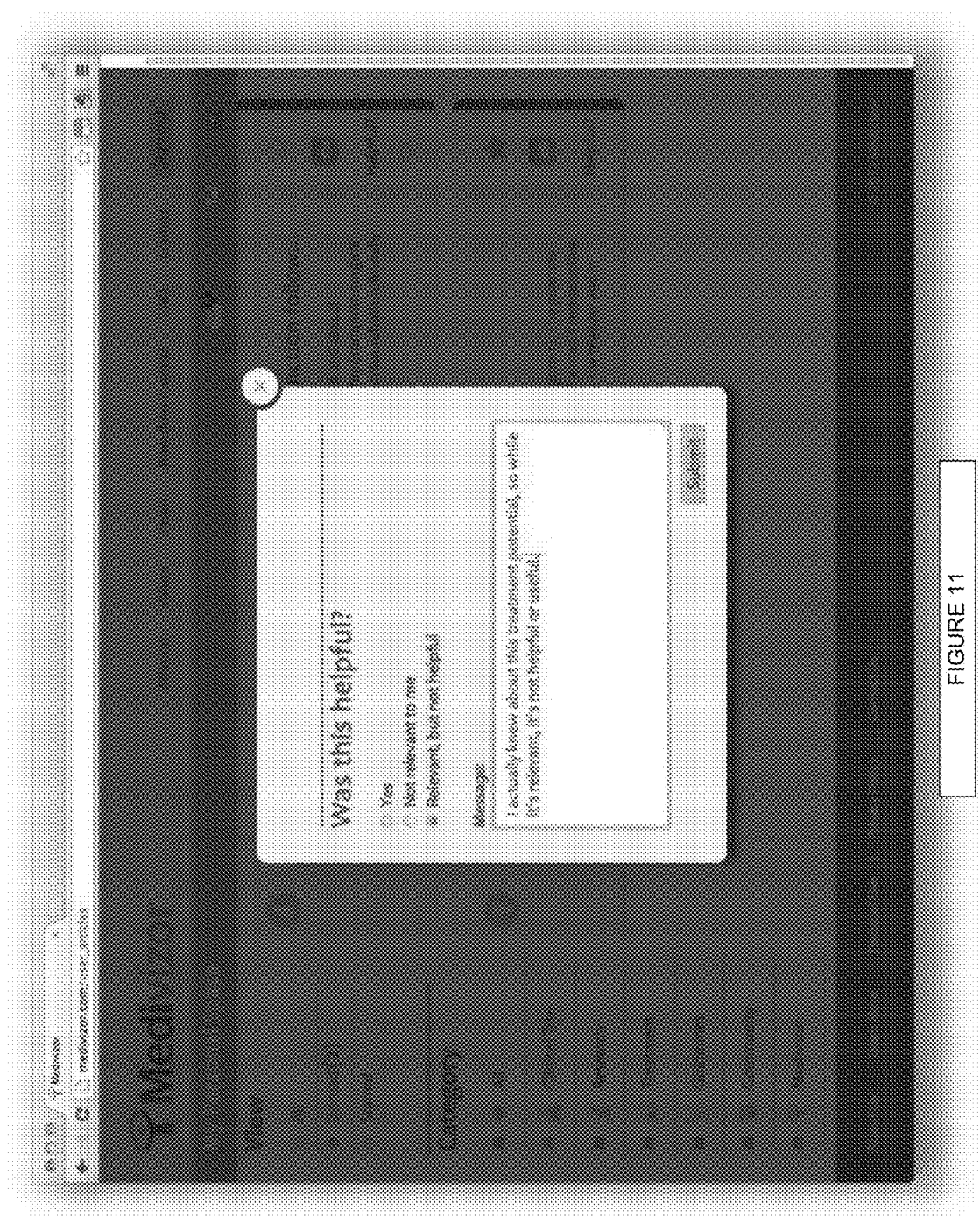
FIG. 11 illustrates features of some embodiments of the present invention.
Figure 12:
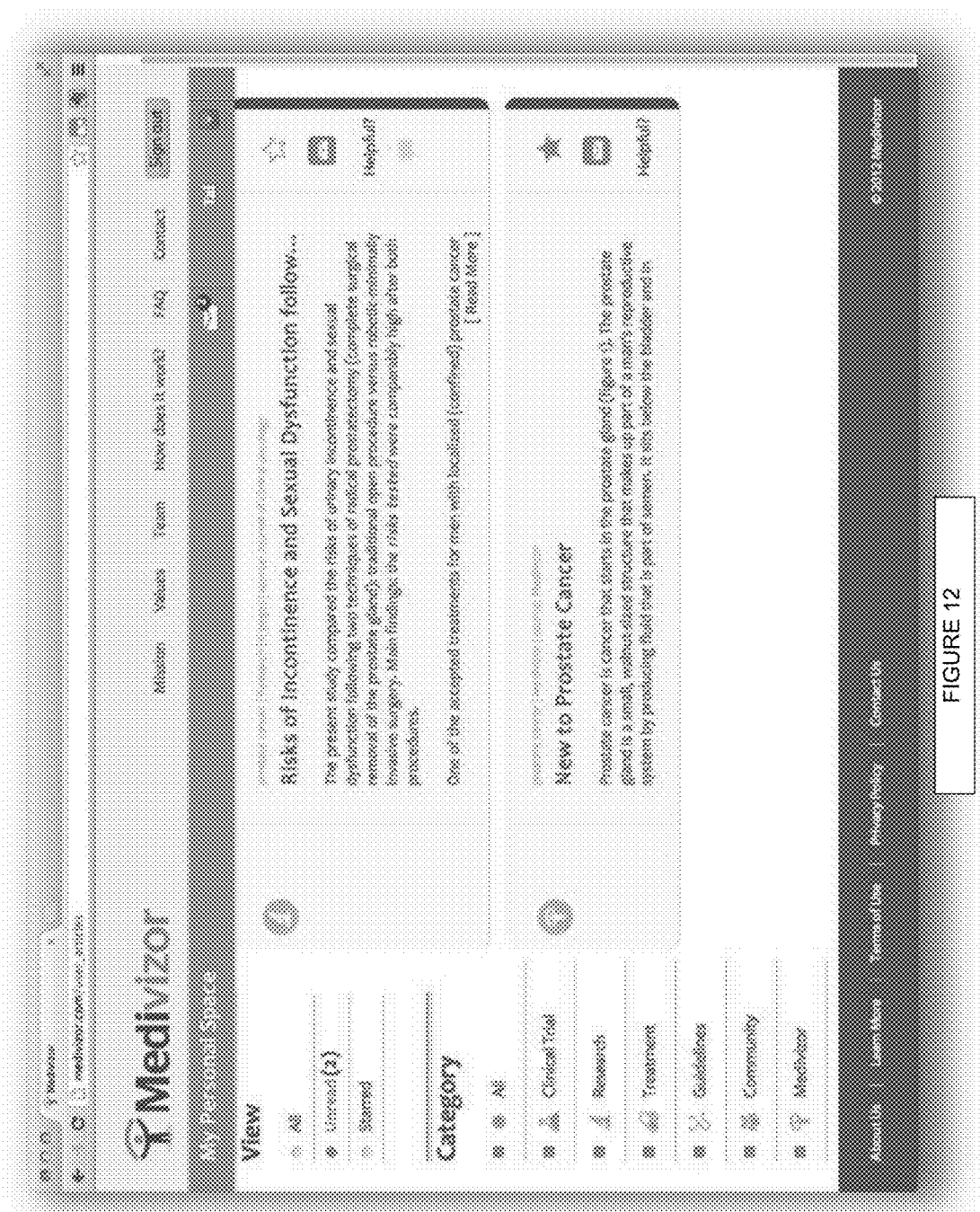
FIG. 12 illustrates features of some embodiments of the present invention.
Figure 13:
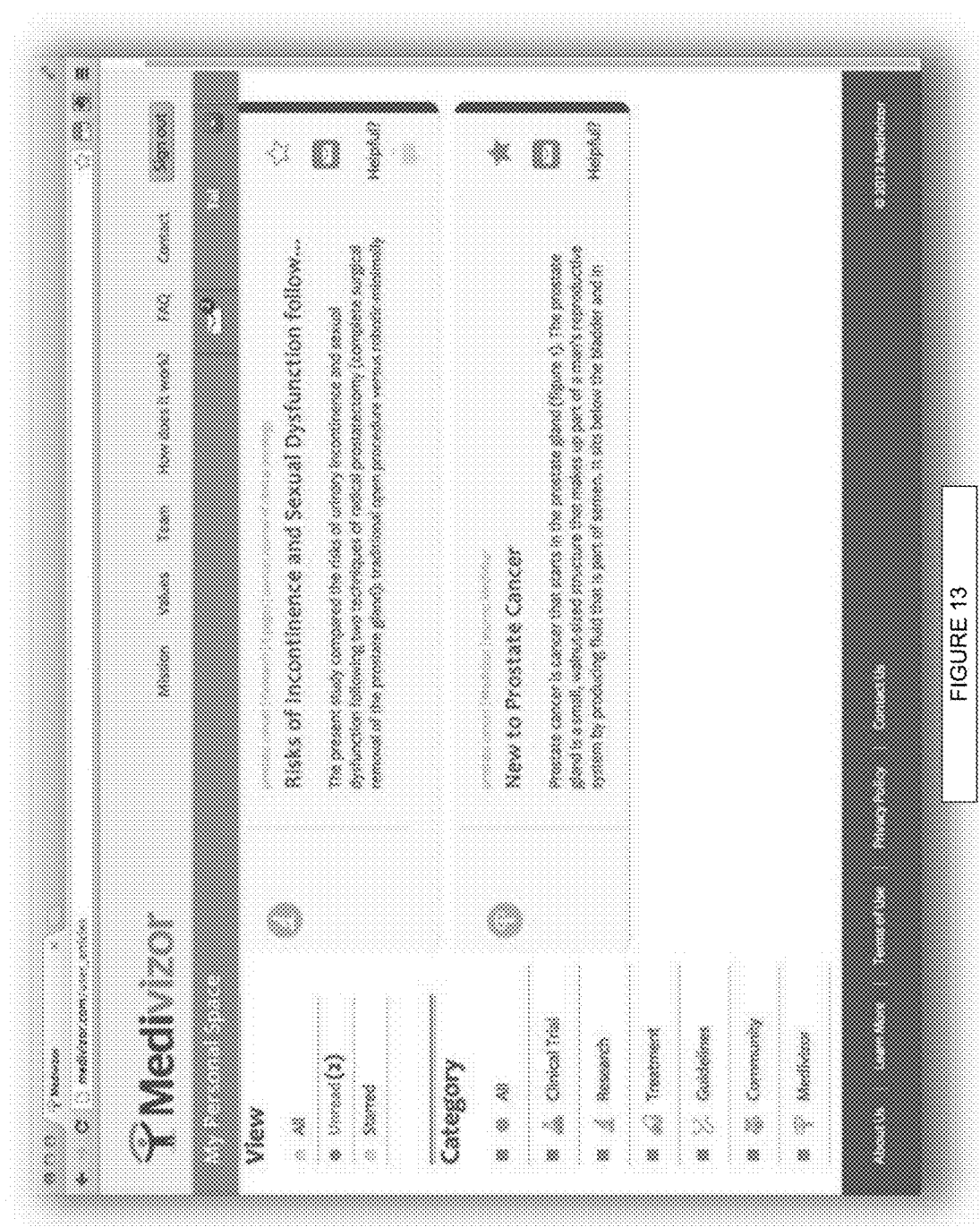
FIG. 13 illustrates features of some embodiments of the present invention.
Figure 14:
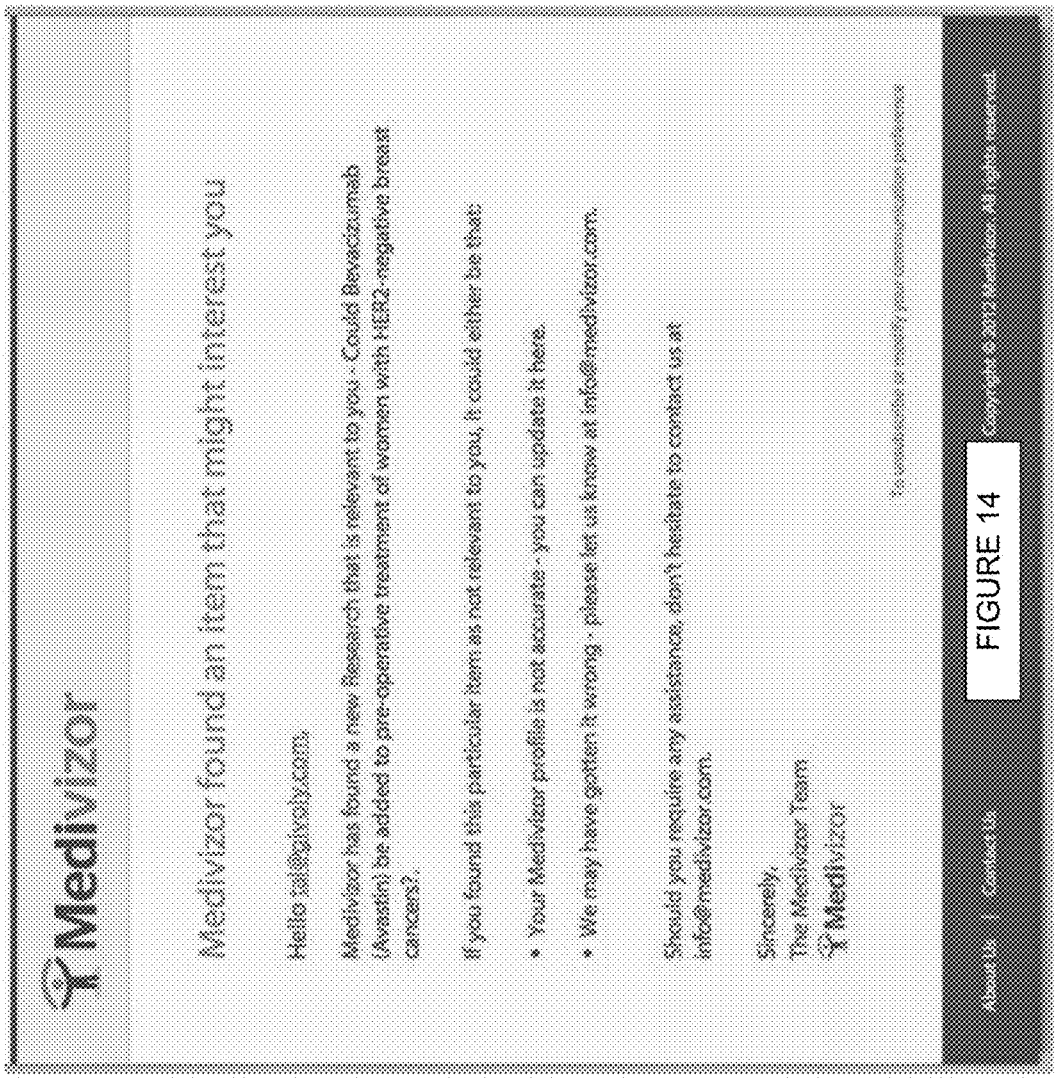
FIG. 14 illustrates features of some embodiments of the present invention.
Figure 15:
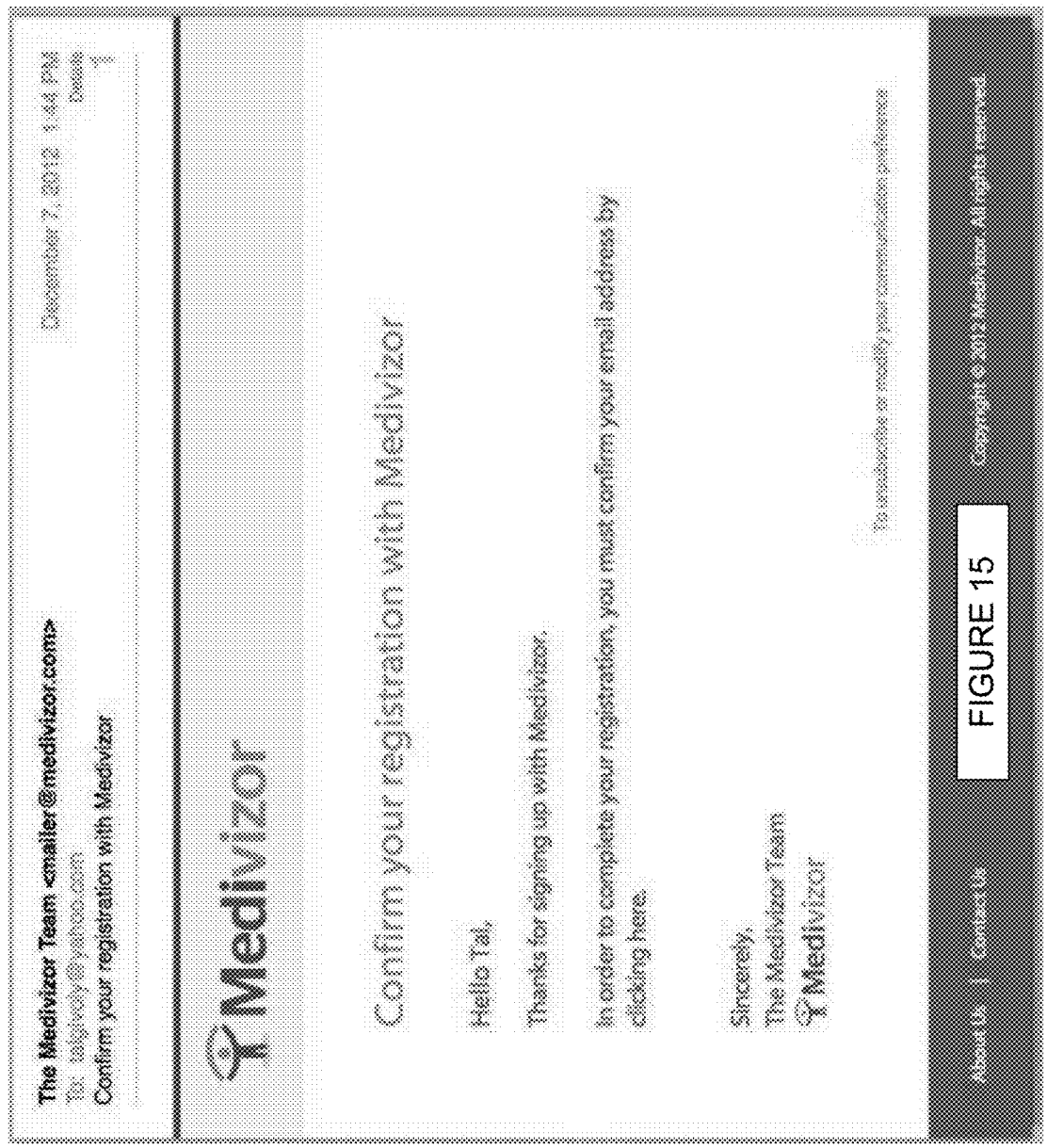
FIG. 15 illustrates features of some embodiments of the present invention.
Figure 16:
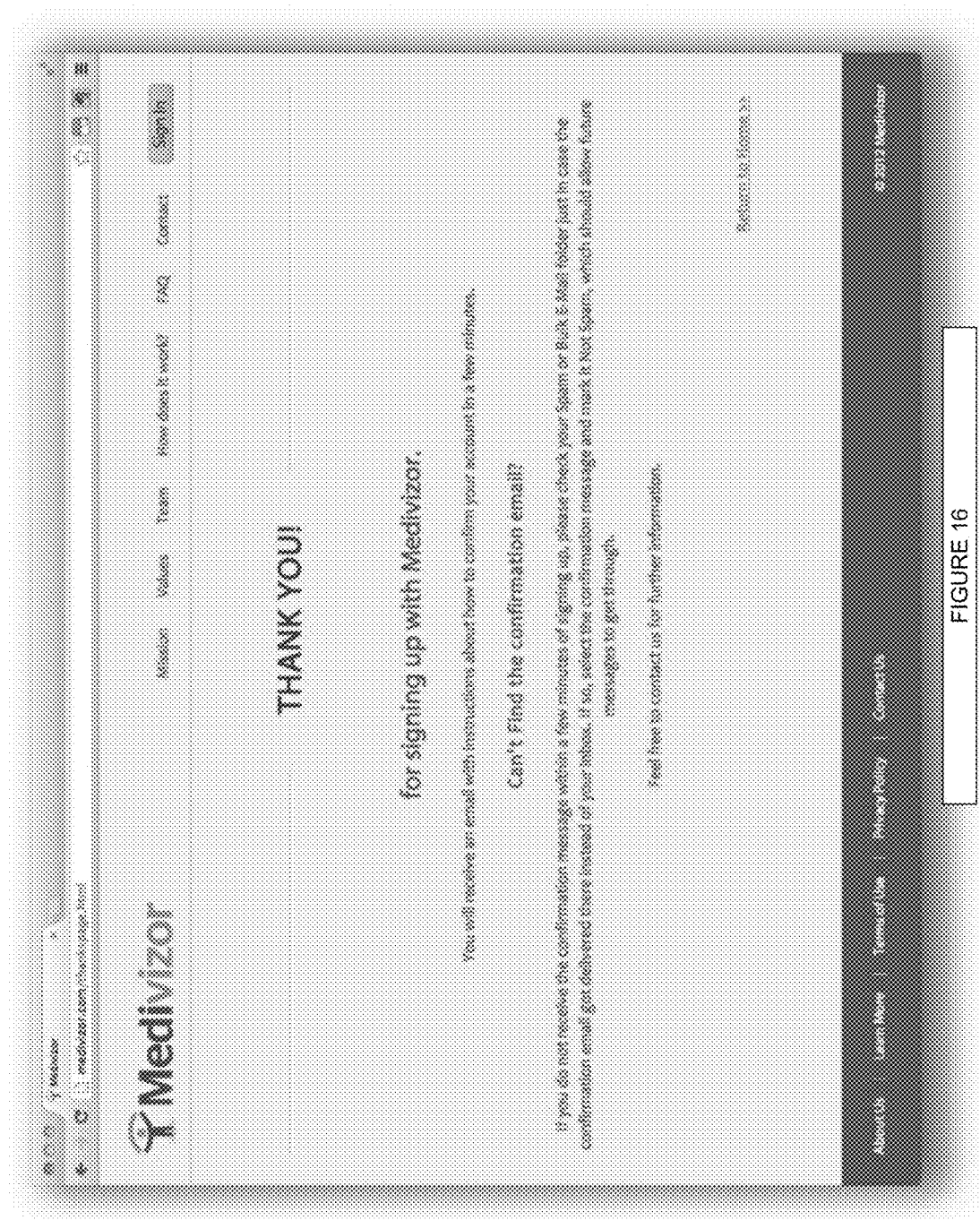
FIG. 16 illustrates features of some embodiments of the present invention.
Figure 17:
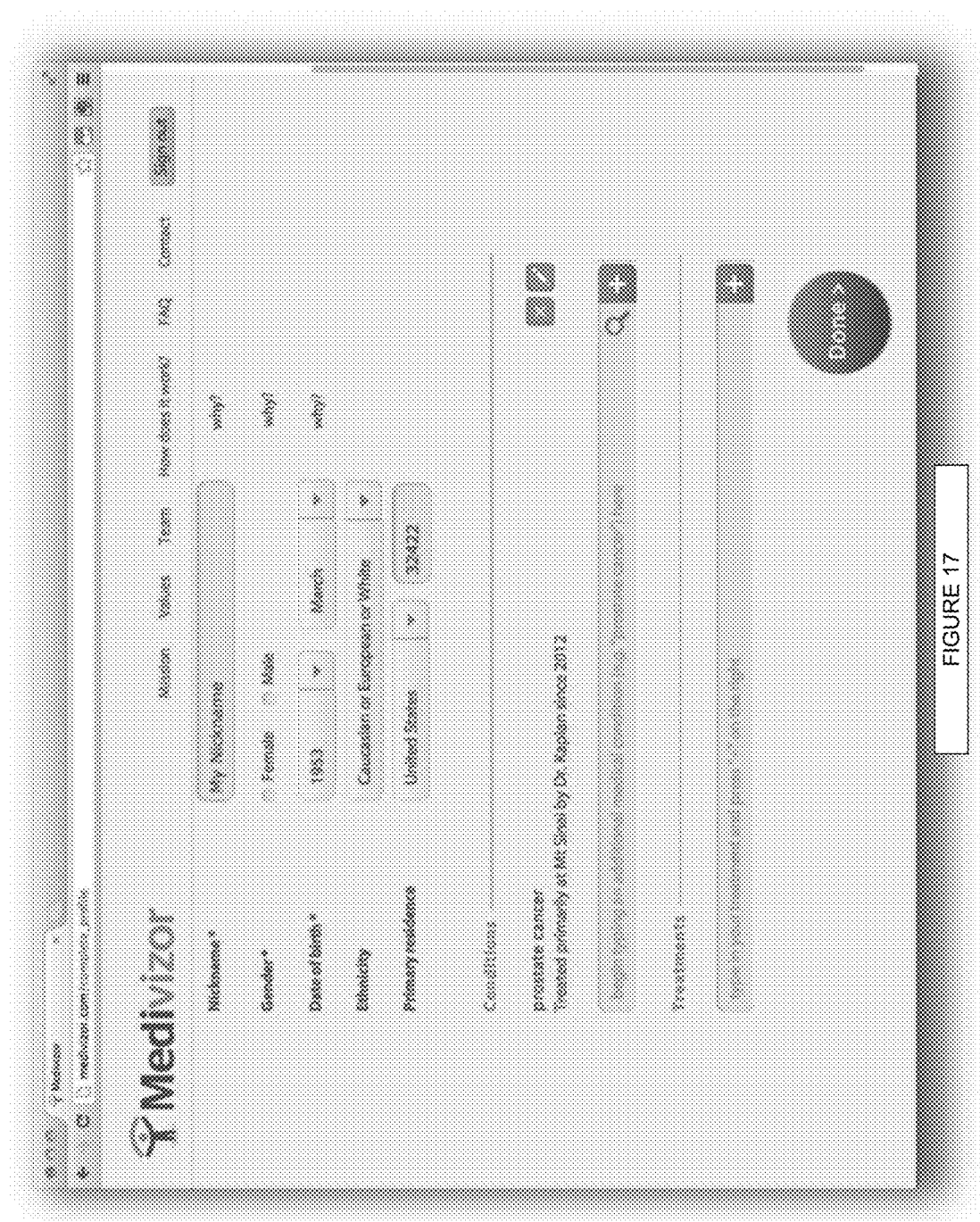
FIG. 17 illustrates features of some embodiments of the present invention.
Figure 18:
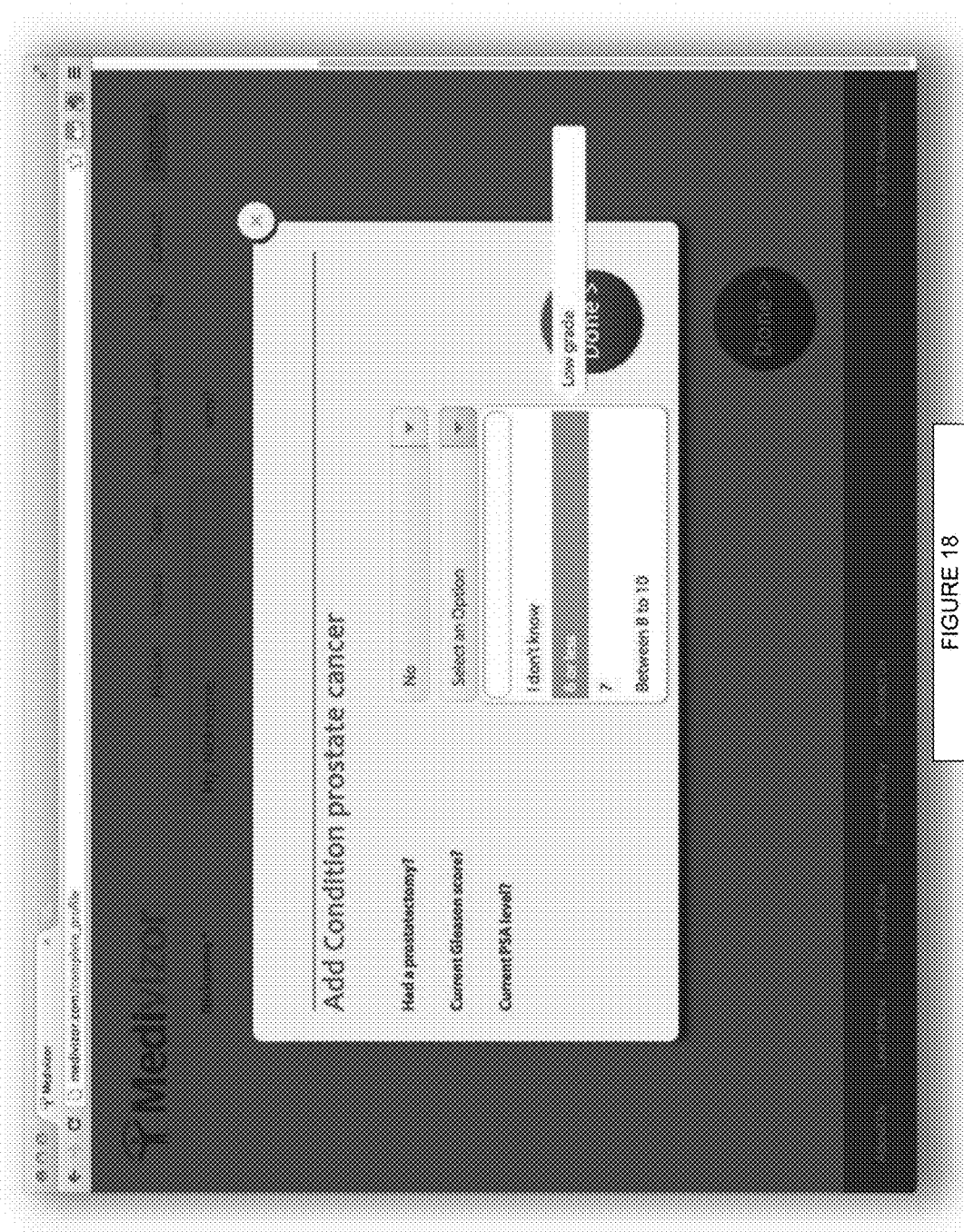
FIG. 18 illustrates features of some embodiments of the present invention.
Figure 19:
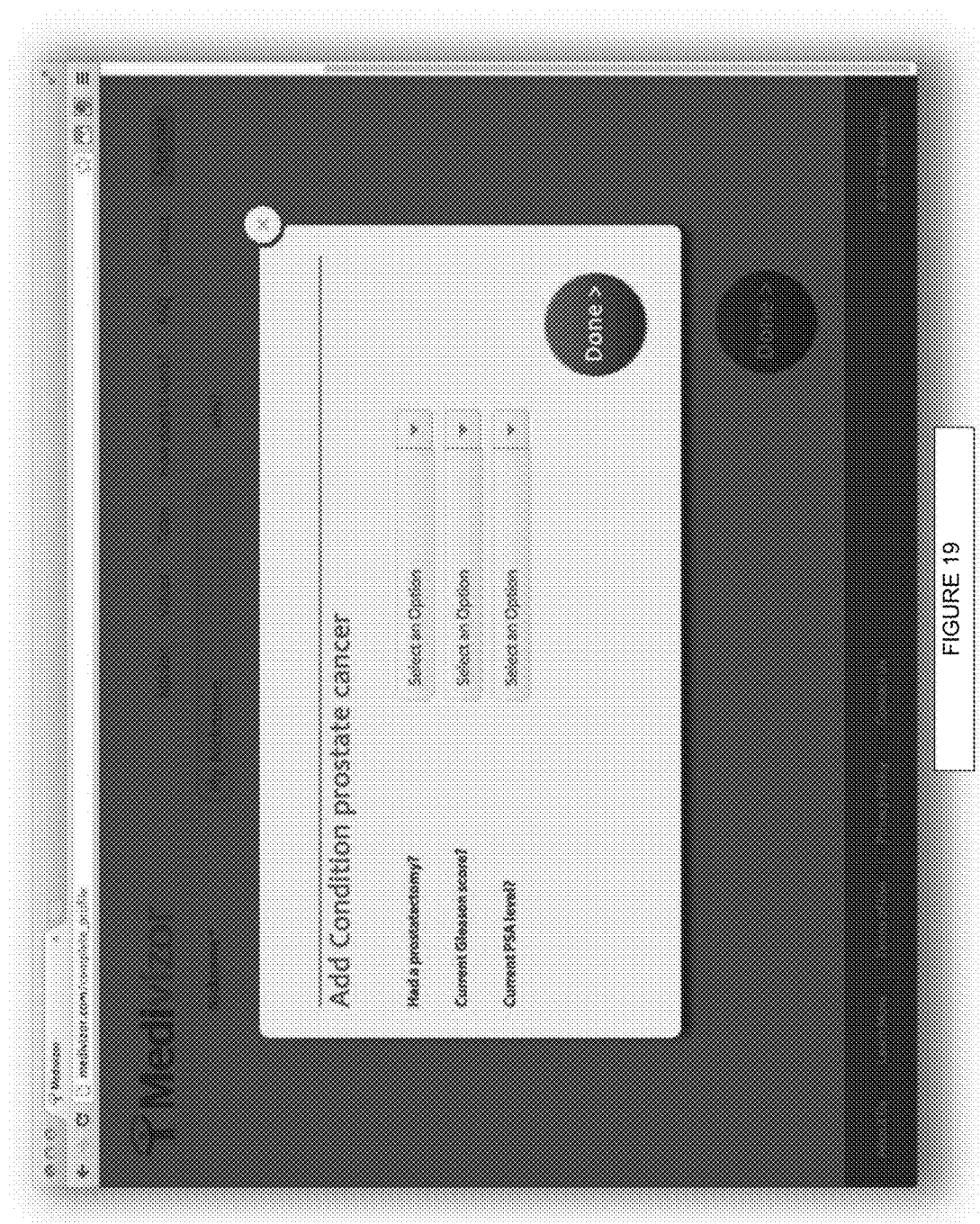
FIG. 19 illustrates features of some embodiments of the present invention.
Figure 20:
FIG. 20 illustrates features of some embodiments of the present invention.
Figure 21:
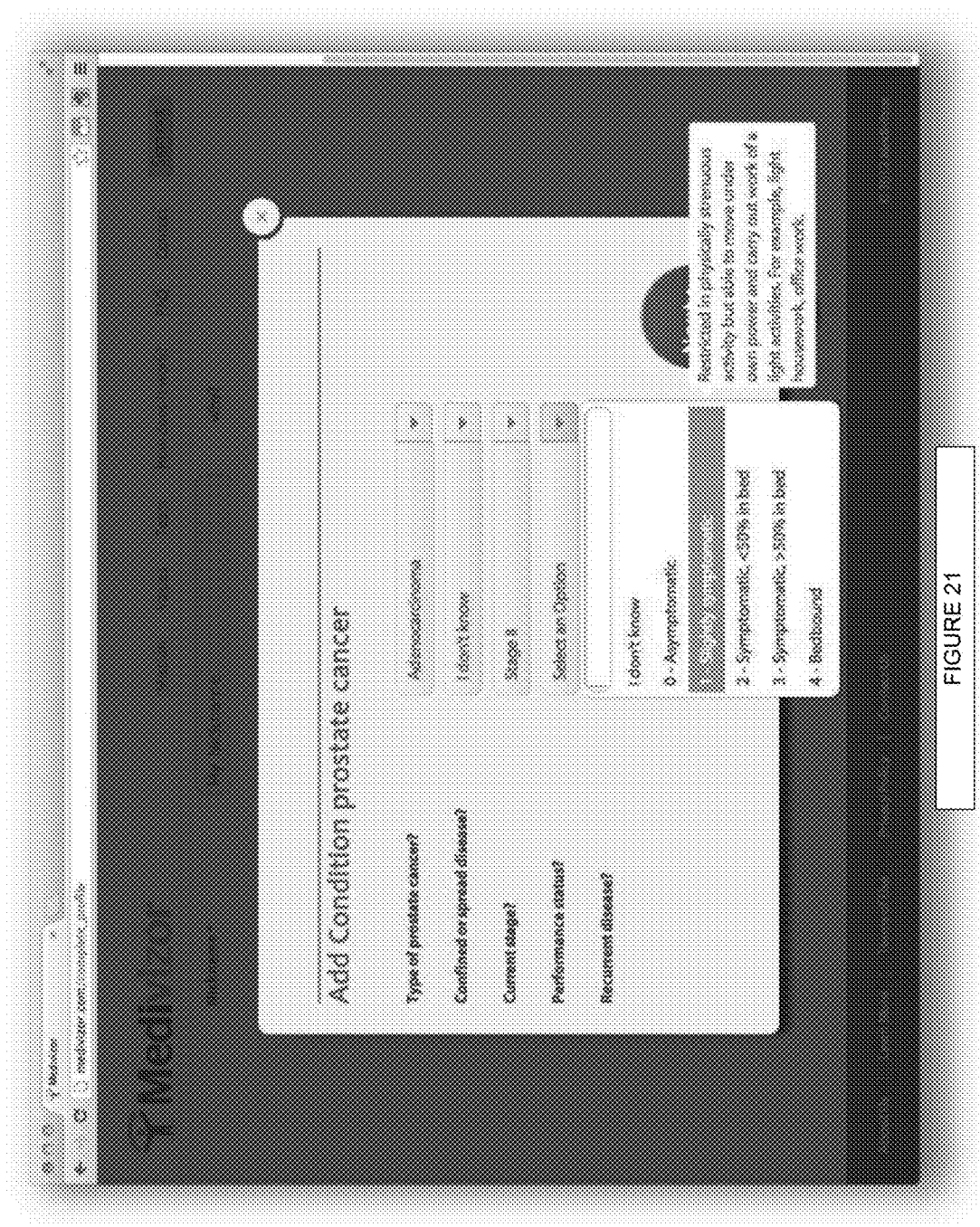
FIG. 21 illustrates features of some embodiments of the present invention.
Figure 22:
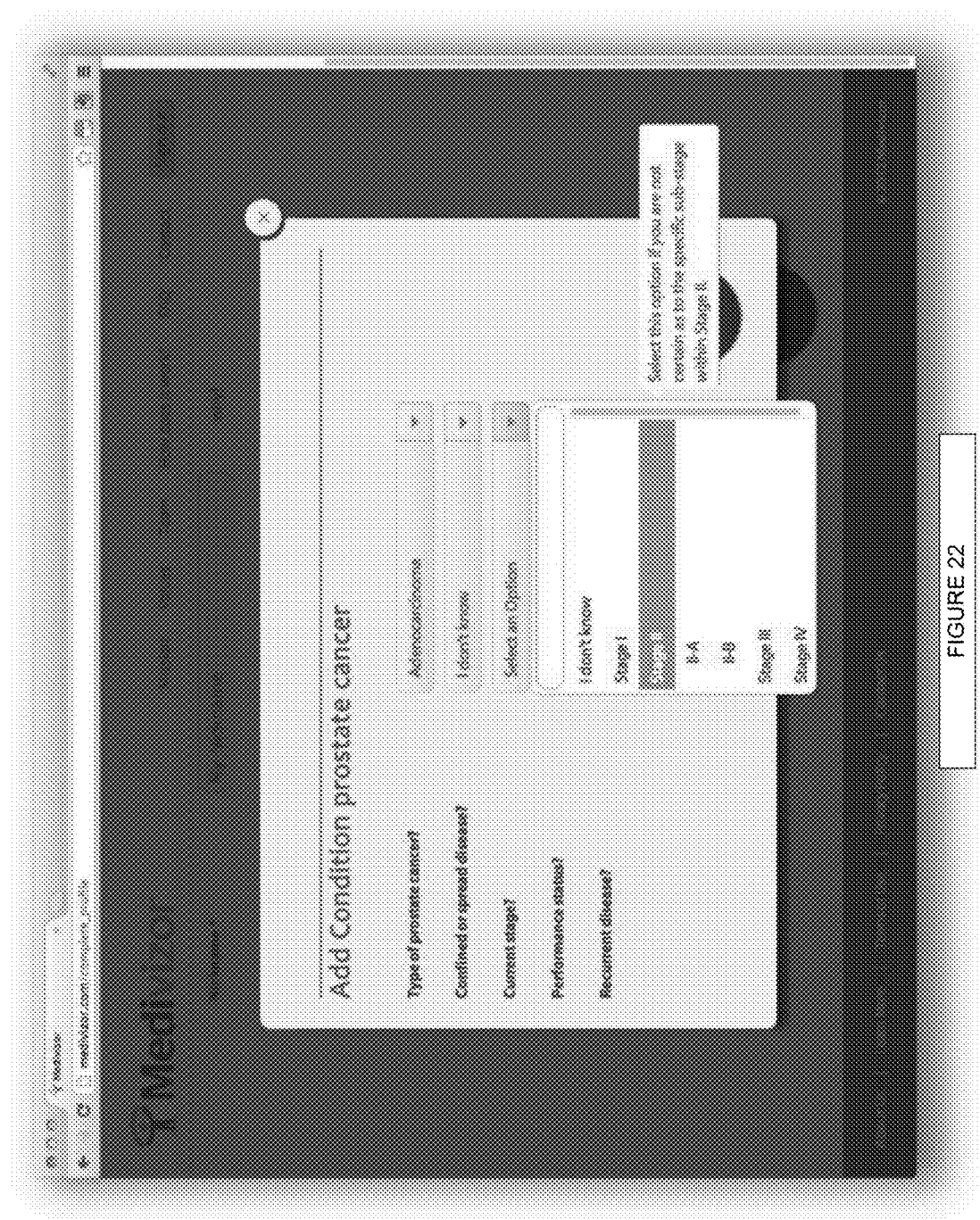
FIG. 22 illustrates features of some embodiments of the present invention.
Figure 23:
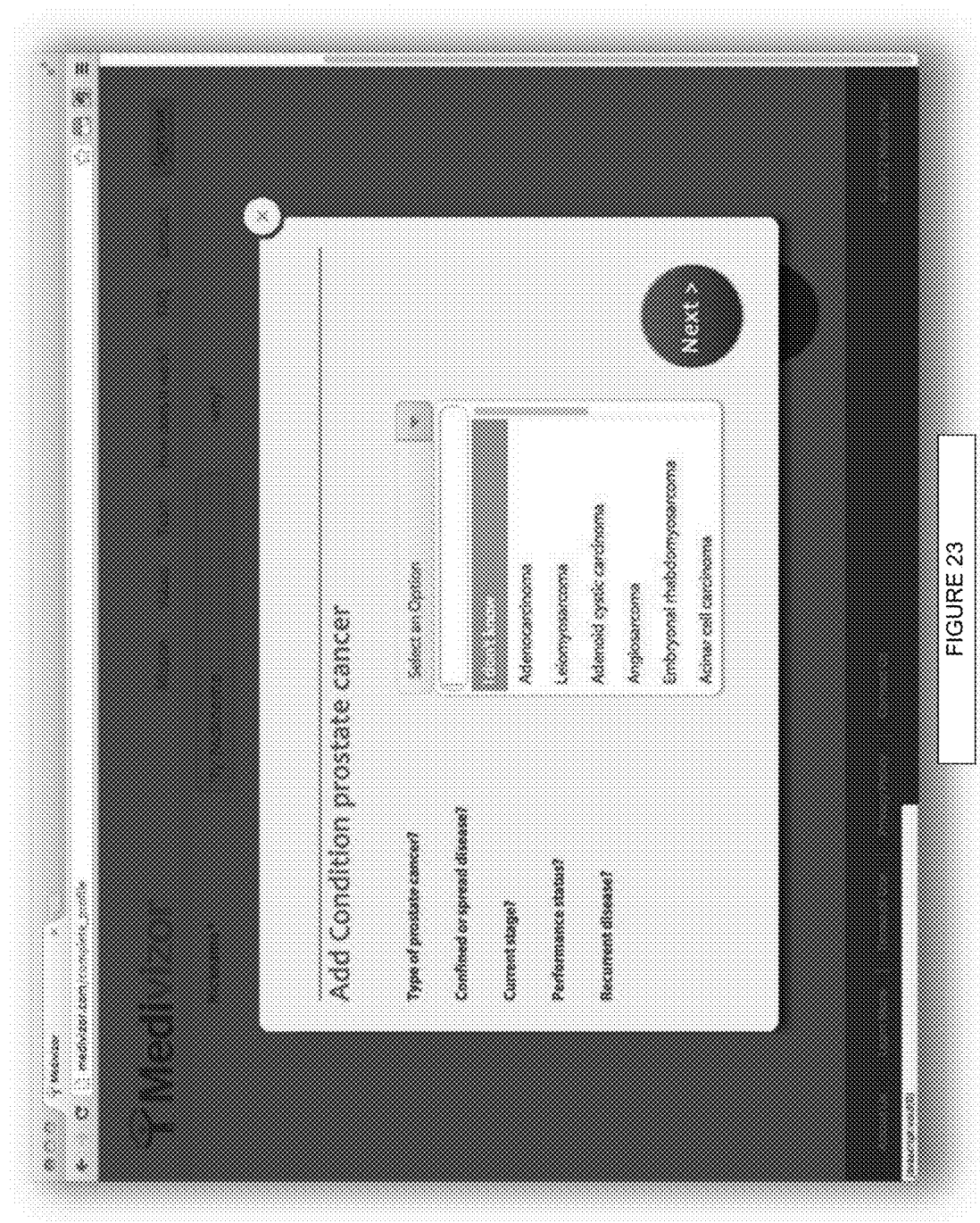
FIG. 23 illustrates features of some embodiments of the present invention.
Figure 24:
FIG. 24 illustrates features of some embodiments of the present invention.
Figure 25:
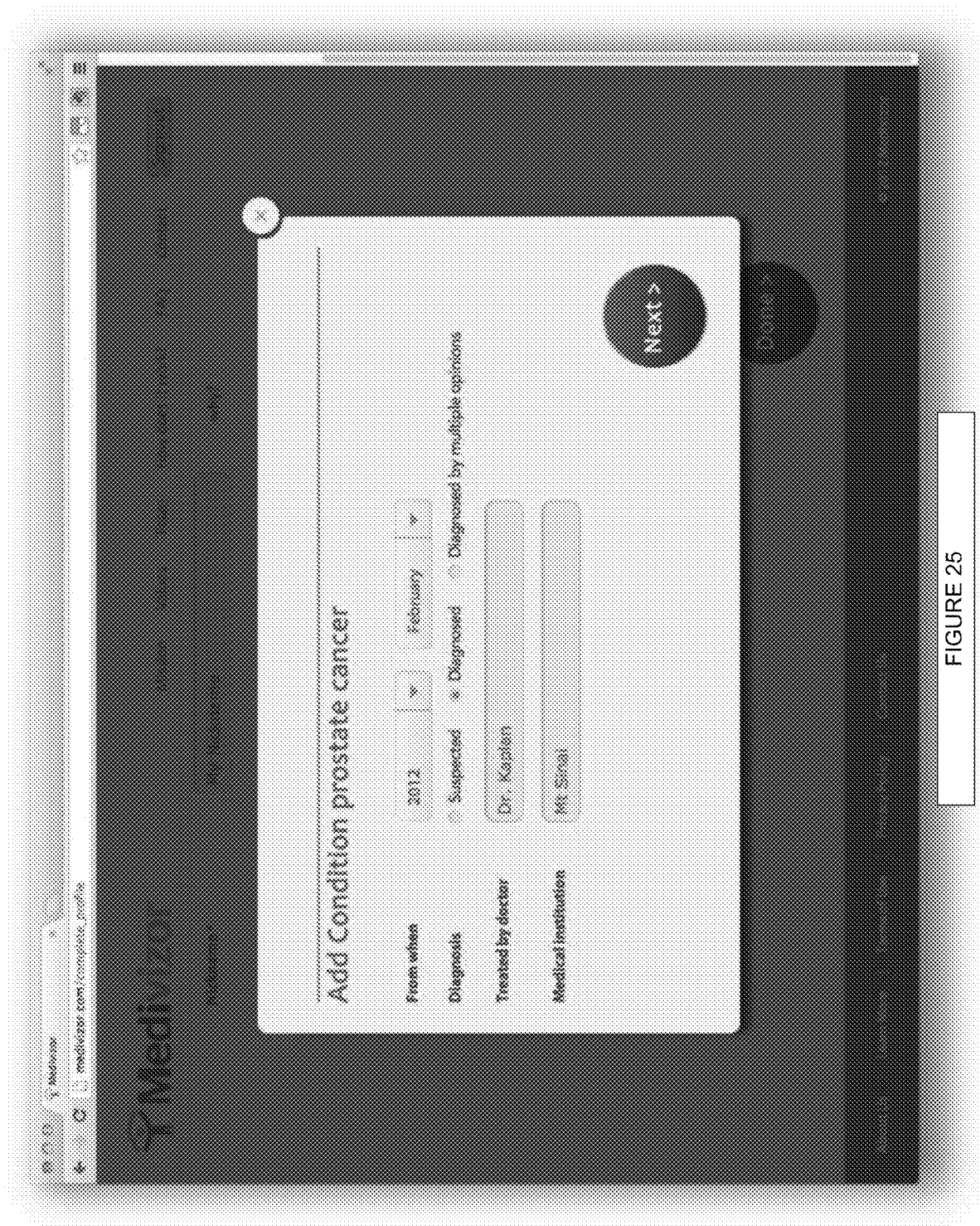
FIG. 25 illustrates features of some embodiments of the present invention.
Figure 26:
FIG. 26 illustrates features of some embodiments of the present invention.
Figure 27:
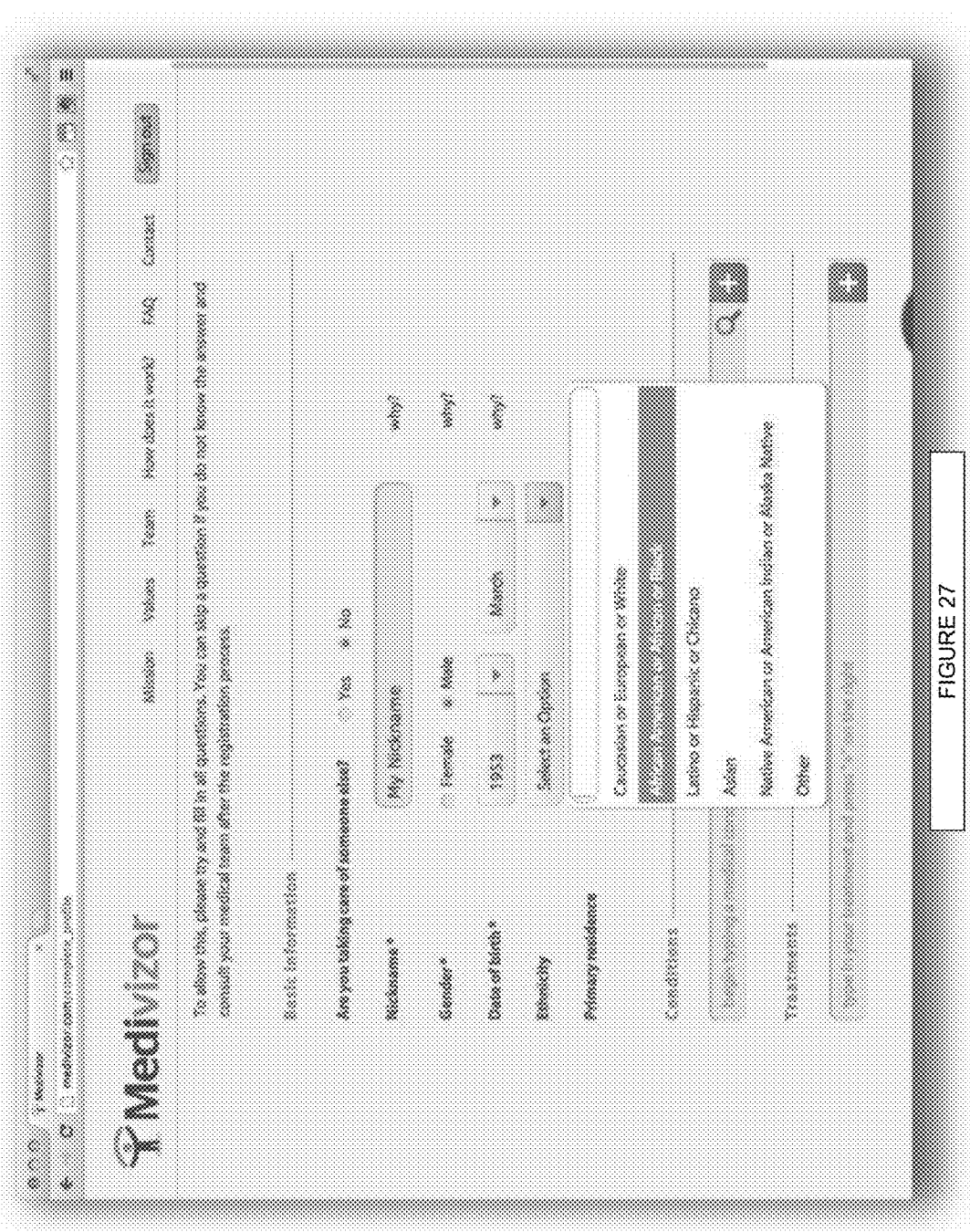
FIG. 27 illustrates features of some embodiments of the present invention.
Figure 28:
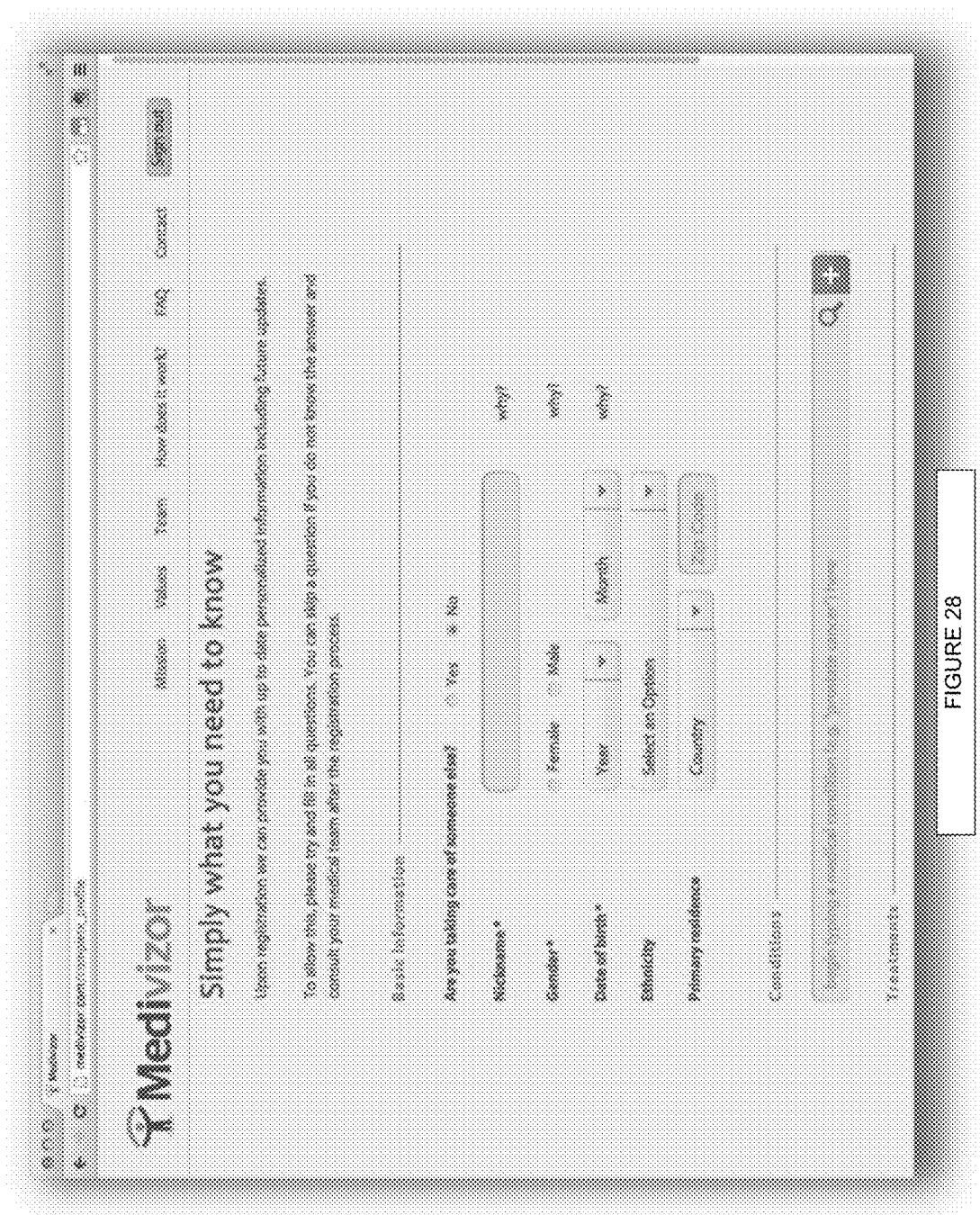
FIG. 28 illustrates features of some embodiments of the present invention.
Figure 29:
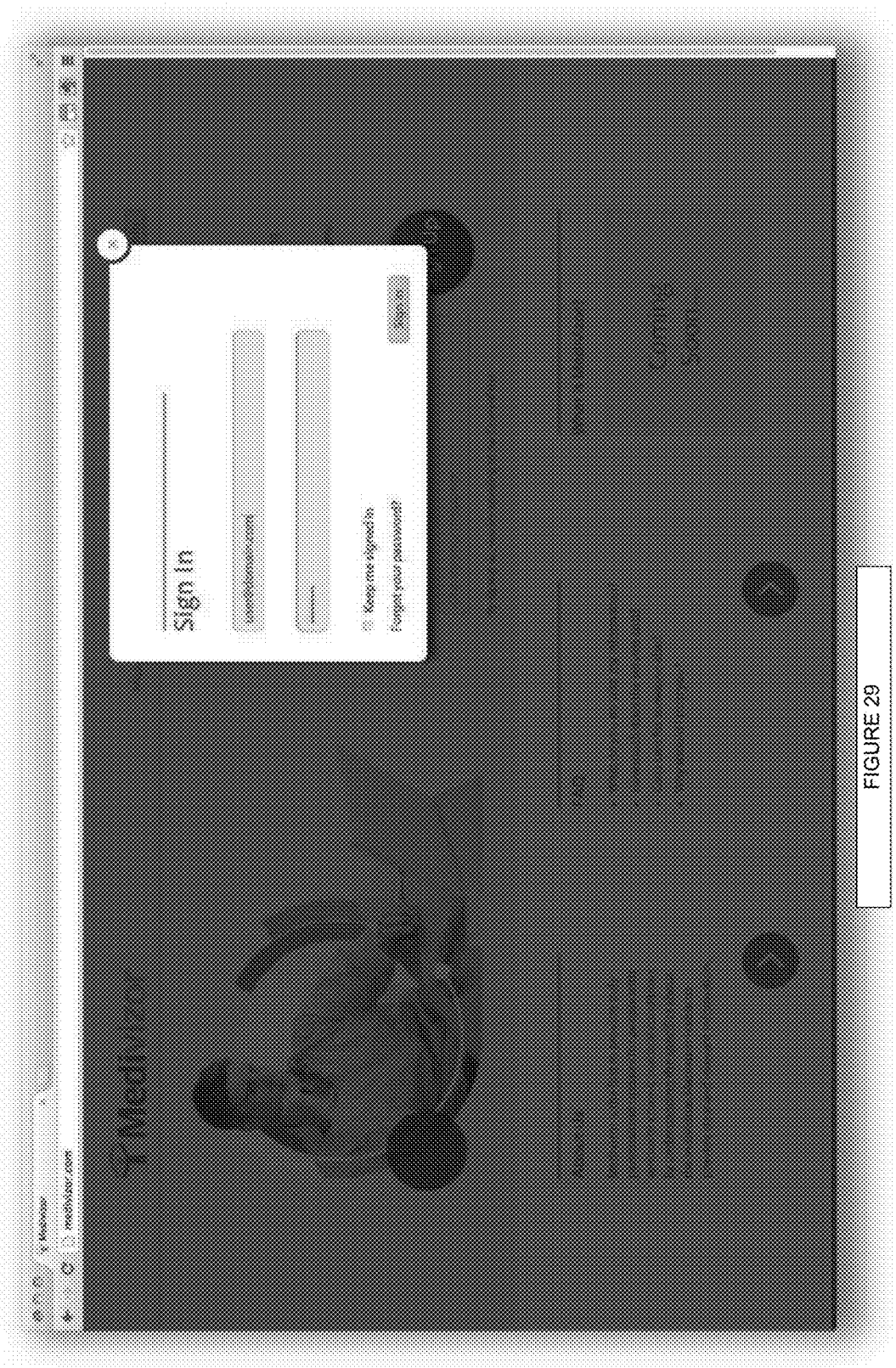
FIG. 29 illustrates features of some embodiments of the present invention.
Figure 30:
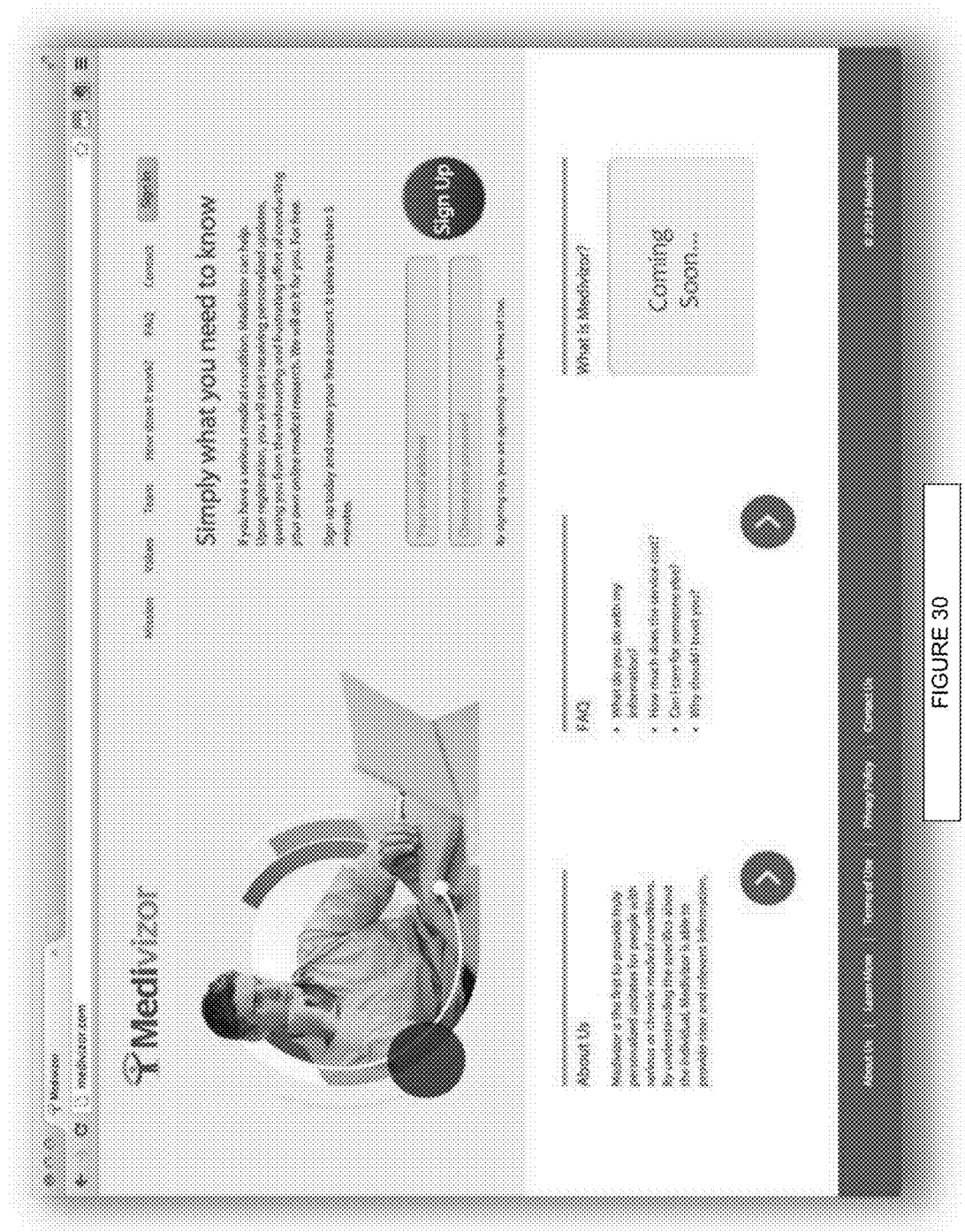
FIG. 30 illustrates features of some embodiments of the present invention.
Figure 31:
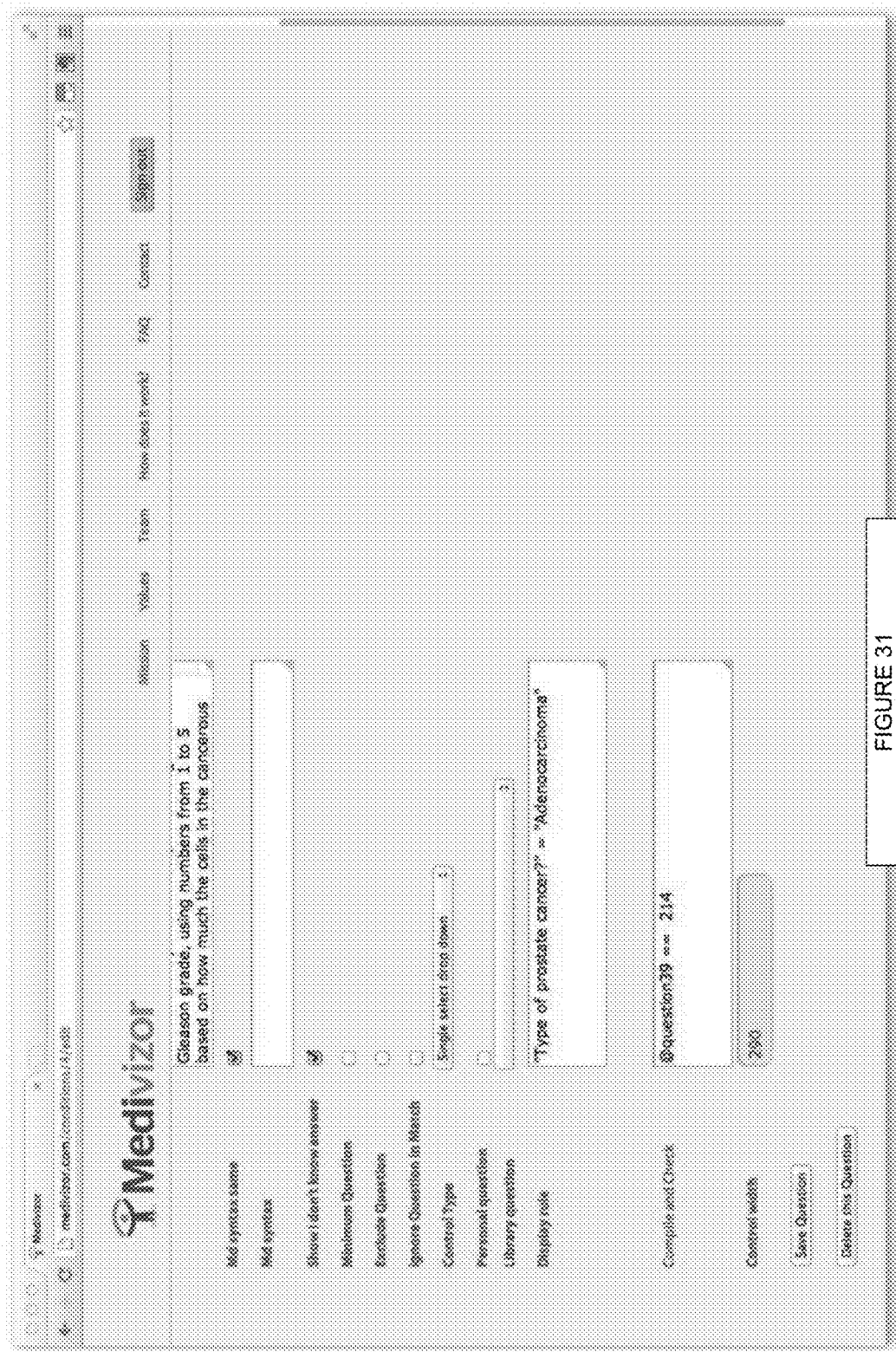
FIG. 31 illustrates features of some embodiments of the present invention.
Figure 32:
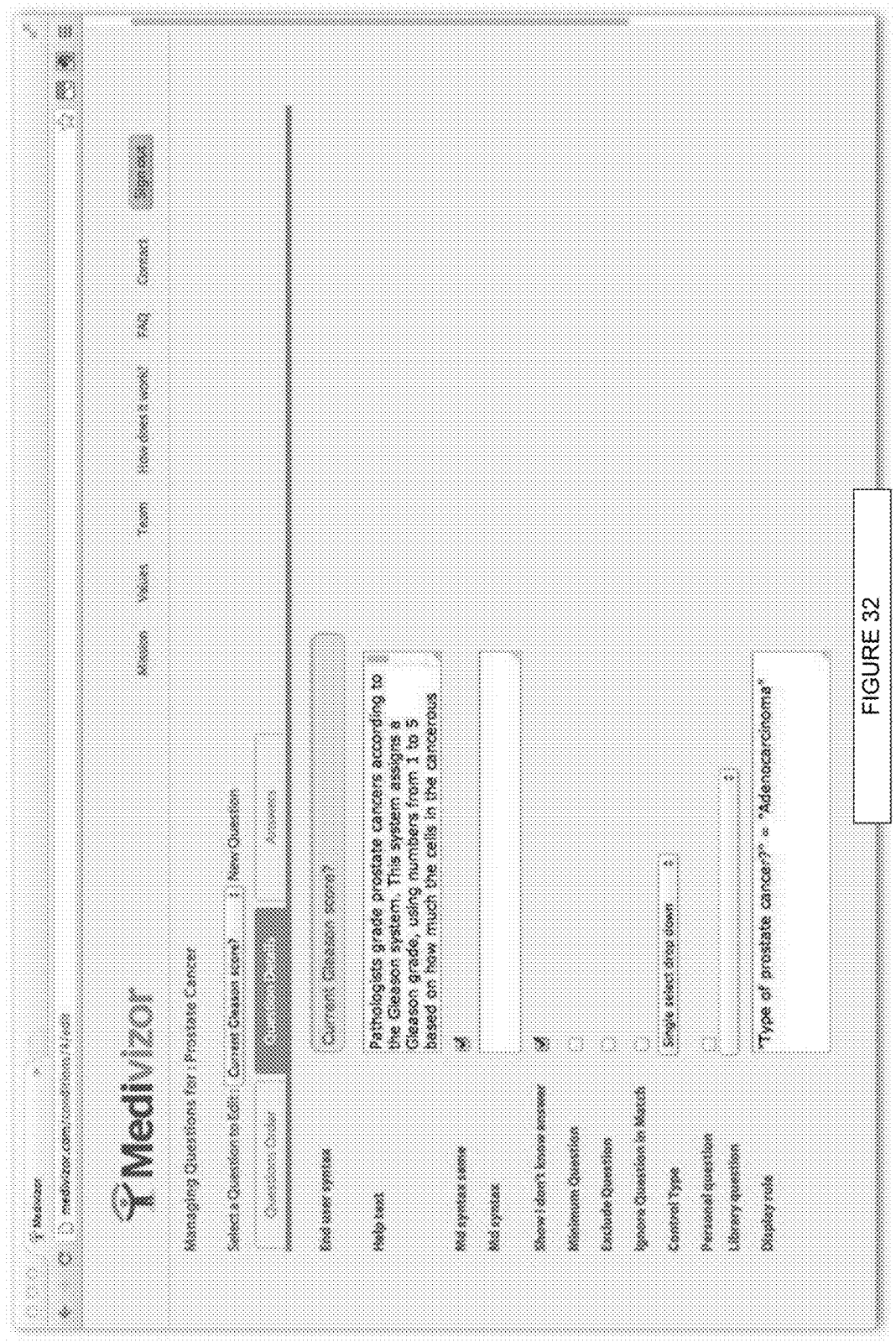
FIG. 32 illustrates features of some embodiments of the present invention.
Figure 33:
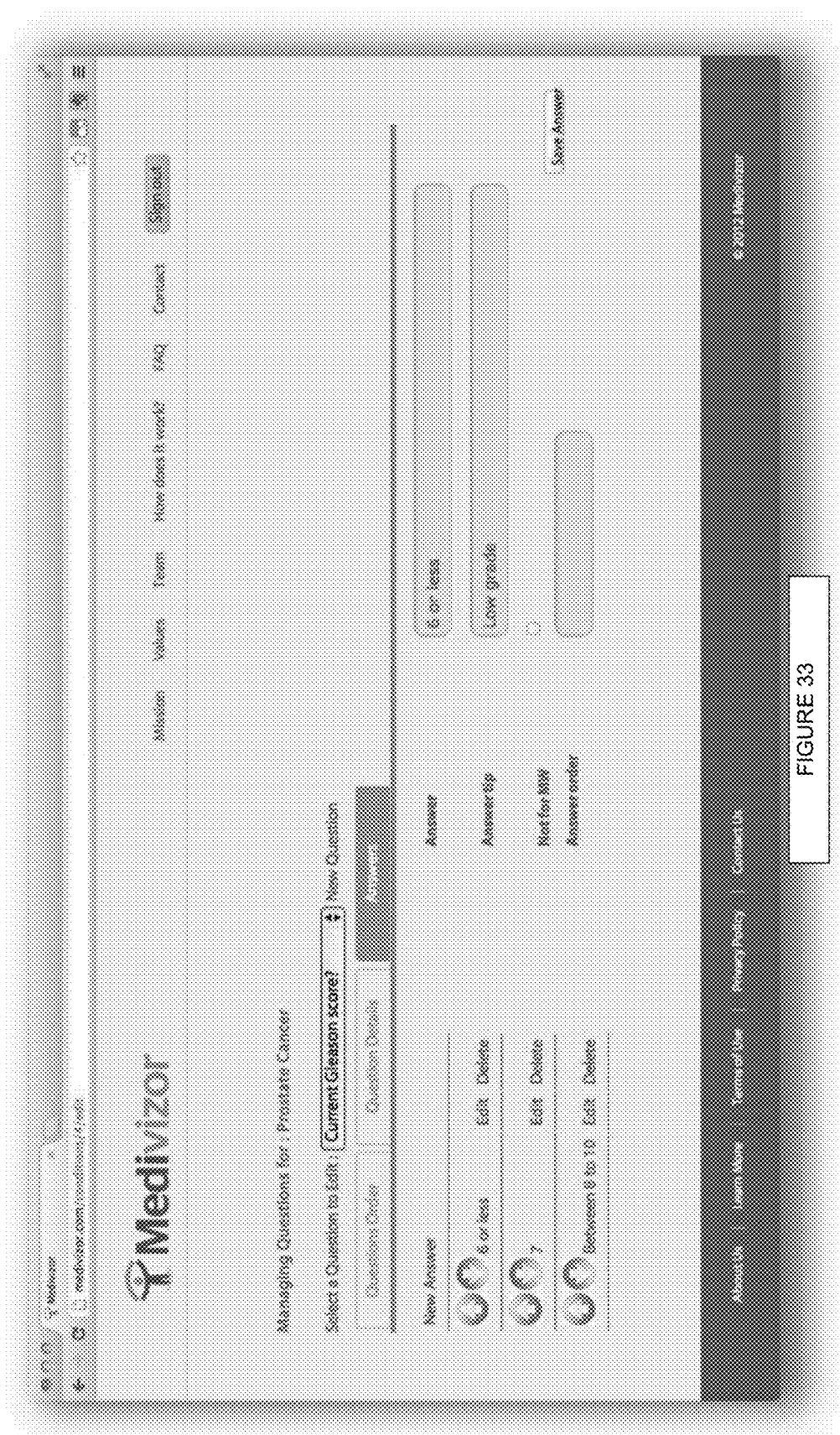
FIG. 33 illustrates features of some embodiments of the present invention.
Figure 34:
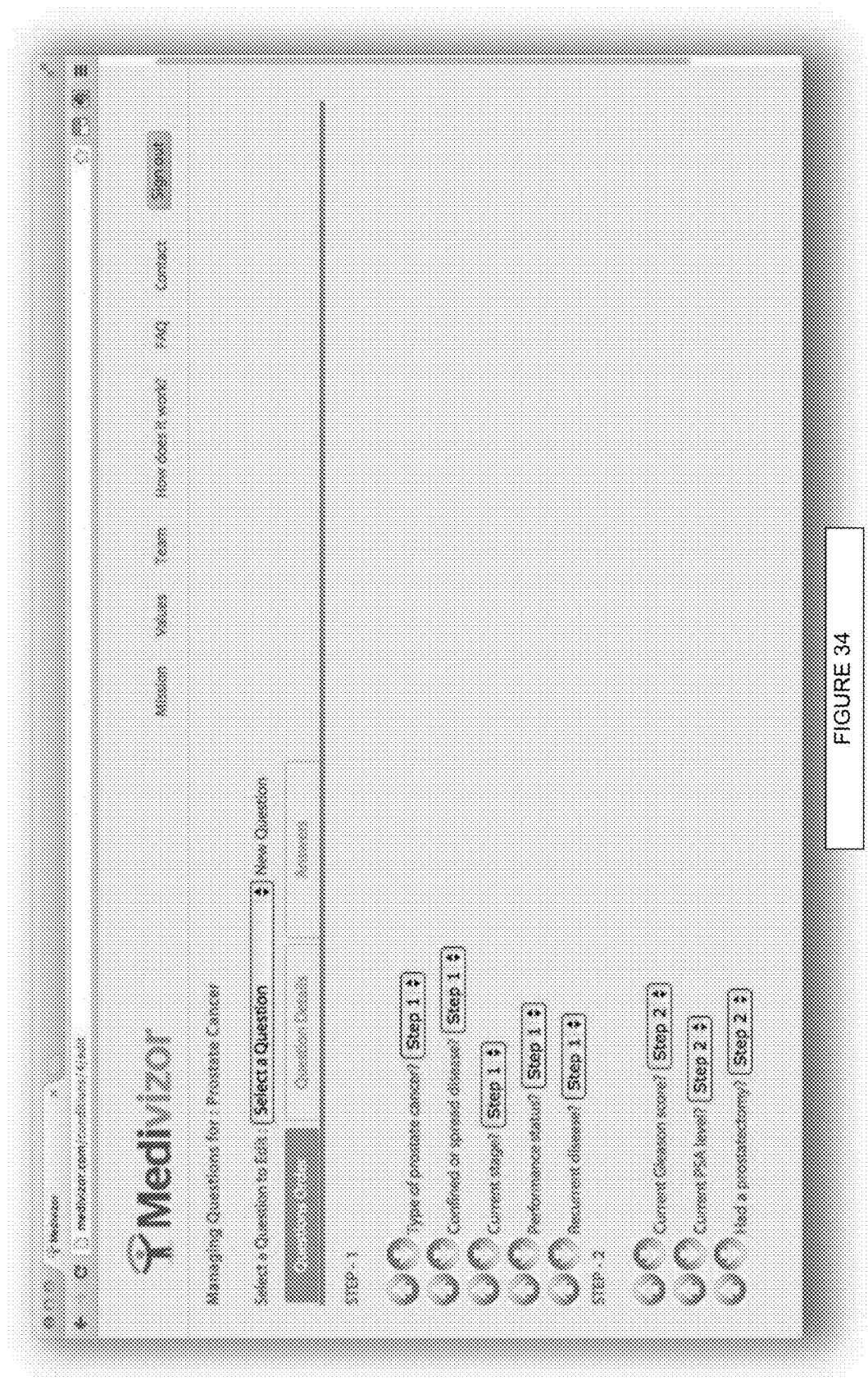
FIG. 34 illustrates features of some embodiments of the present invention.
Figure 35:
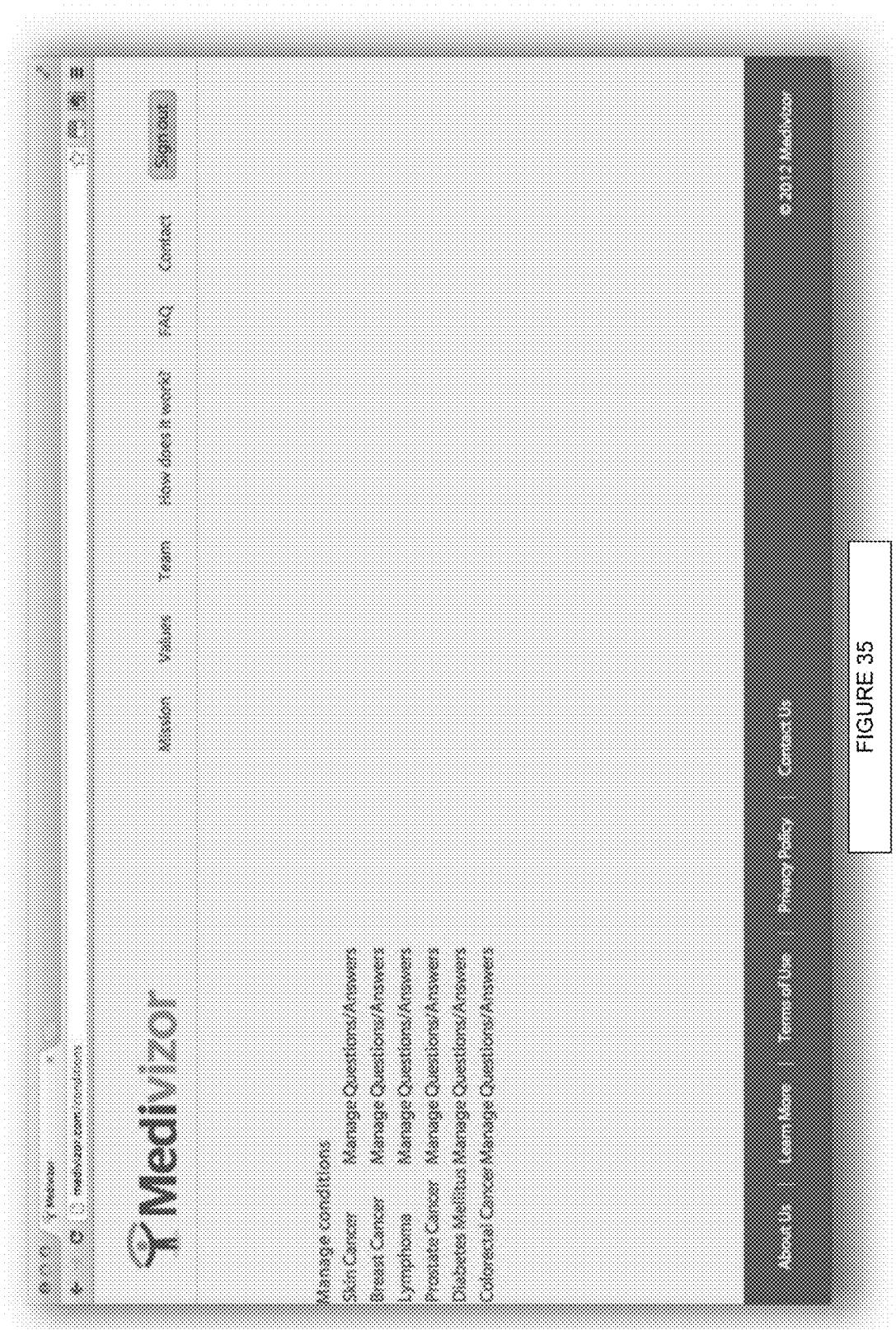
FIG. 35 illustrates features of some embodiments of the present invention.
Figure 36:
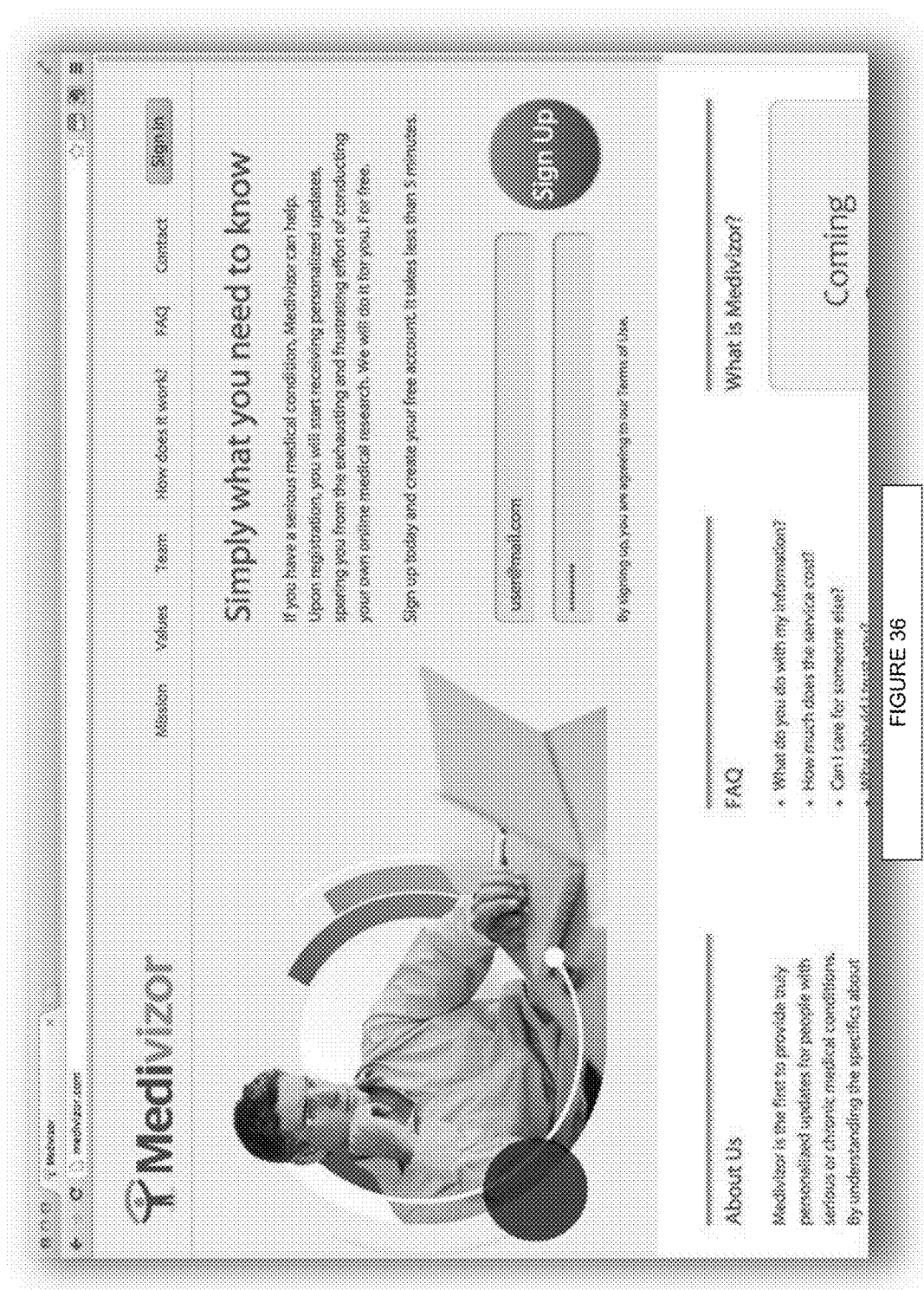
FIG. 36 illustrates features of some embodiments of the present invention.
Figure 37:
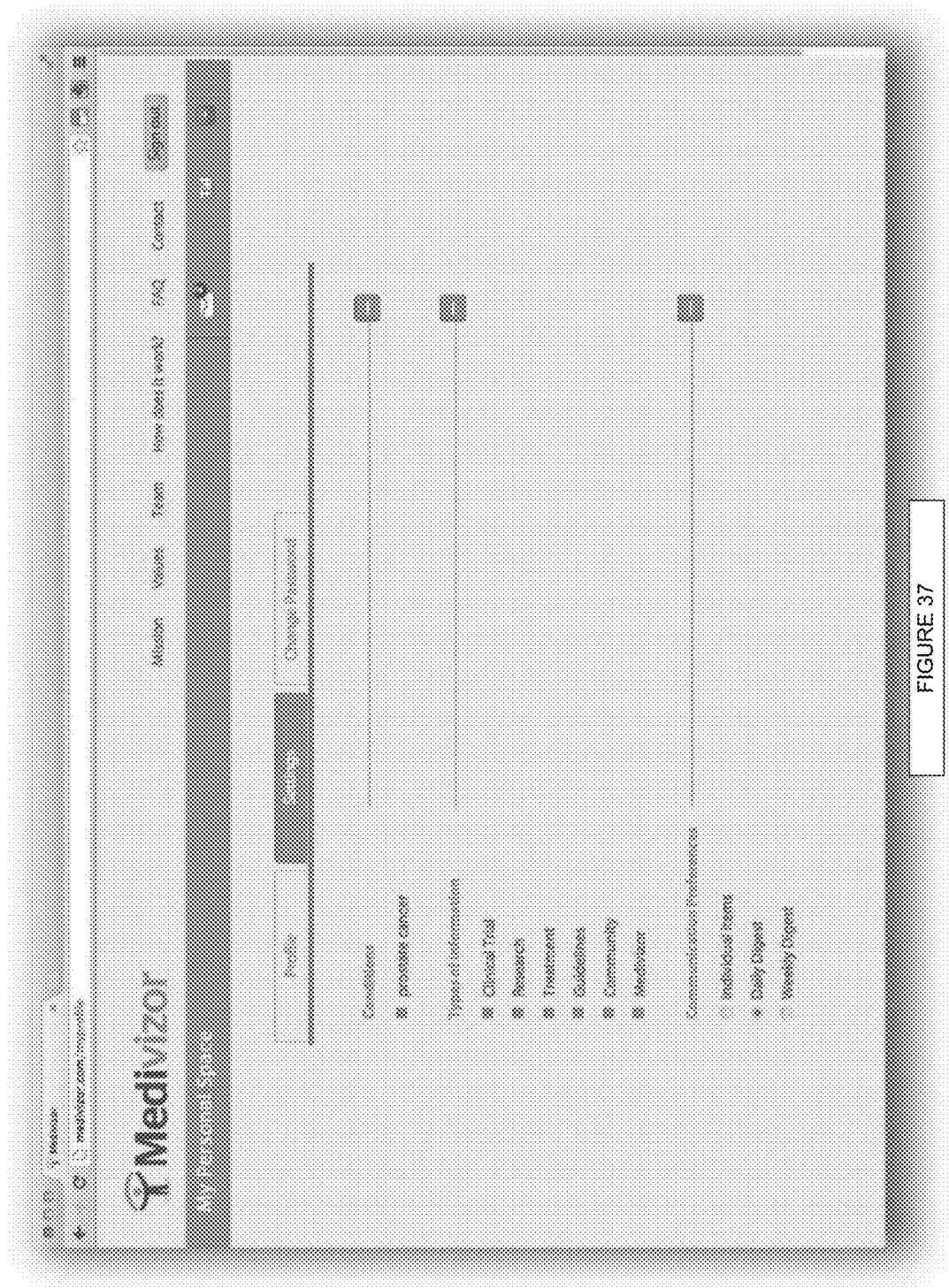
FIG. 37 illustrates features of some embodiments of the present invention.
Figure 38:
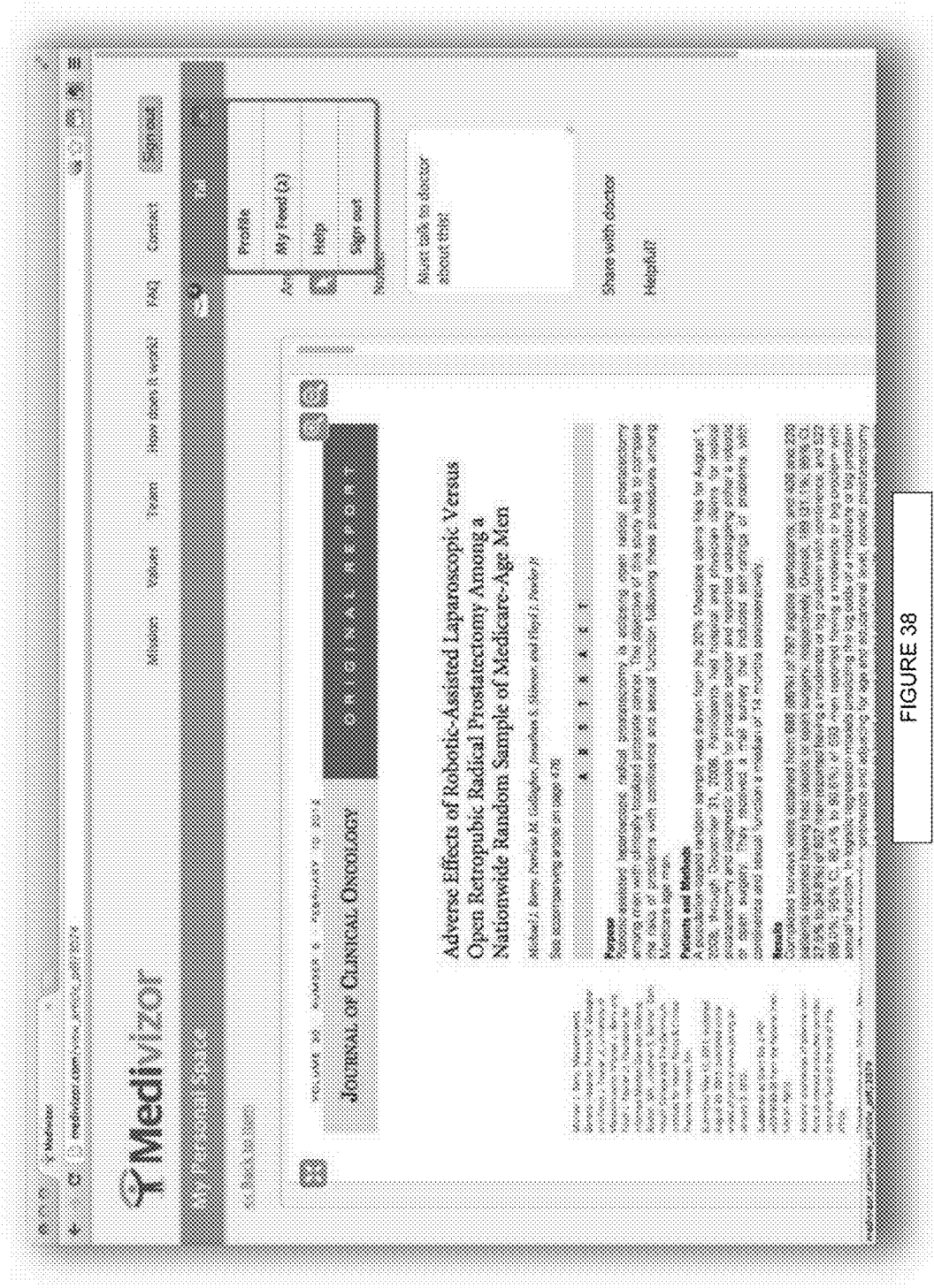
FIG. 38 illustrates features of some embodiments of the present invention.
Figure 39:
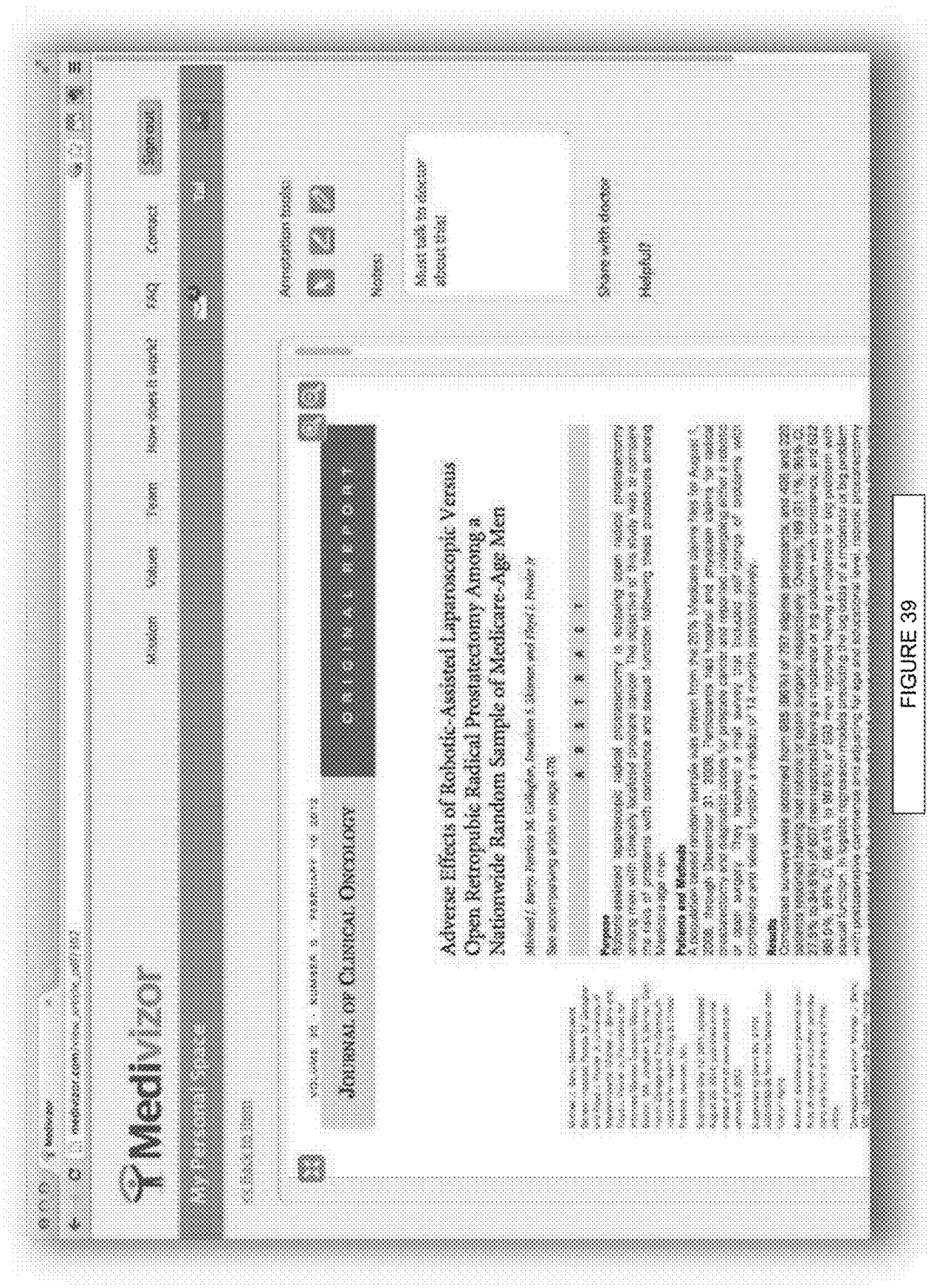
FIG. 39 illustrates features of some embodiments of the present invention.
Figure 40:
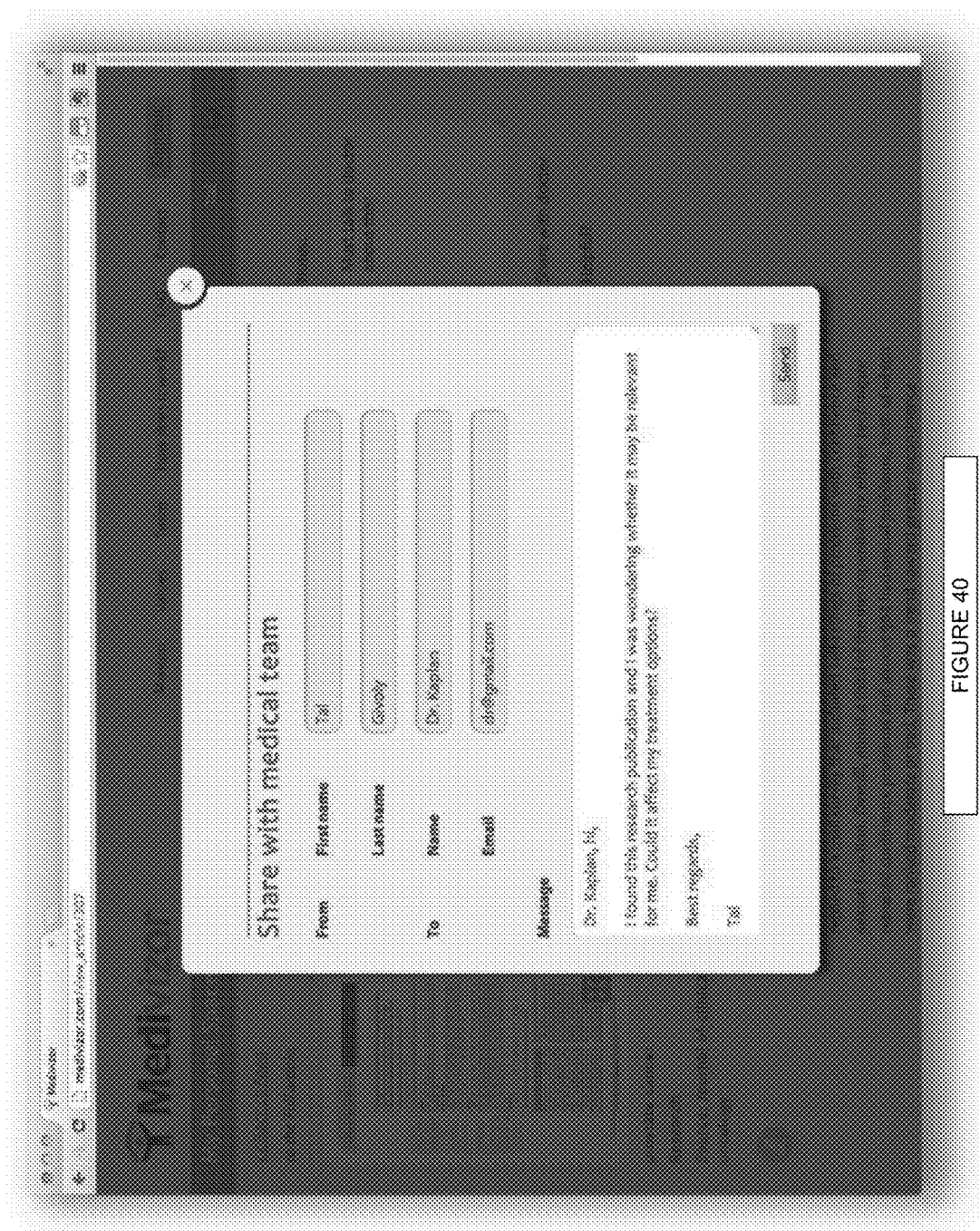
FIG. 40 illustrates features of some embodiments of the present invention.
Figure 41:
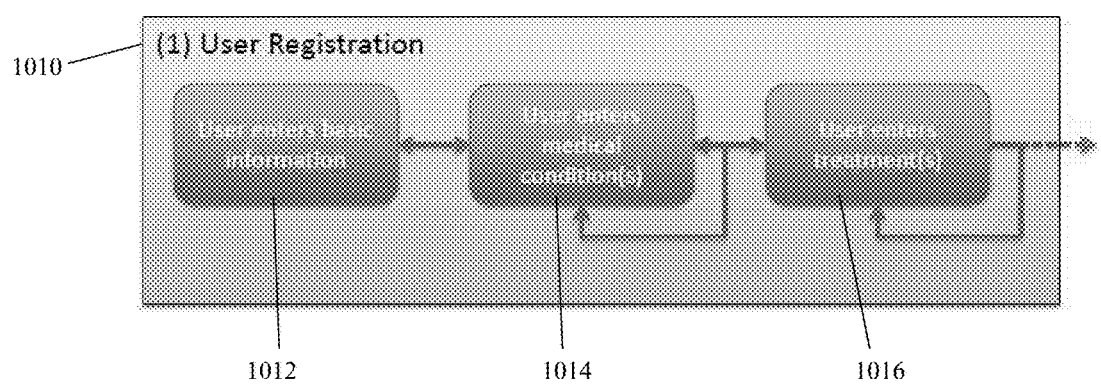
FIG. 41 illustrates features of some embodiments of the present invention.
Figure 42:
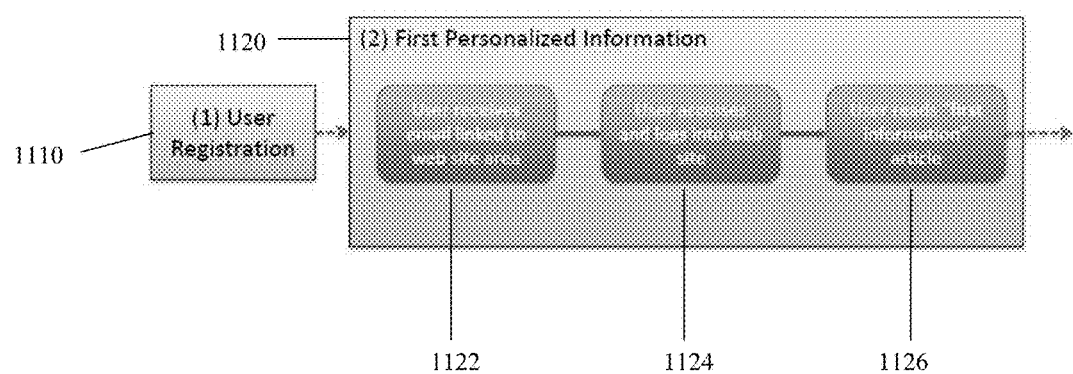
FIG. 42 illustrates features of some embodiments of the present invention.
Figure 43:
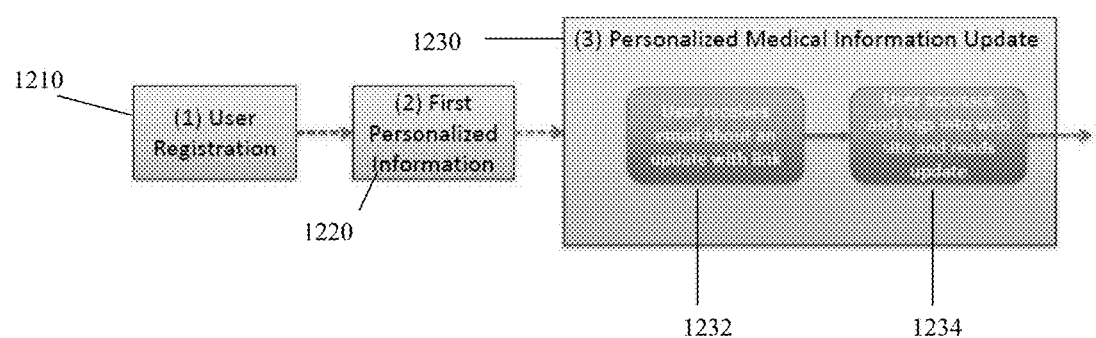
FIG. 43 illustrates features of some embodiments of the present invention.
Figure 44:
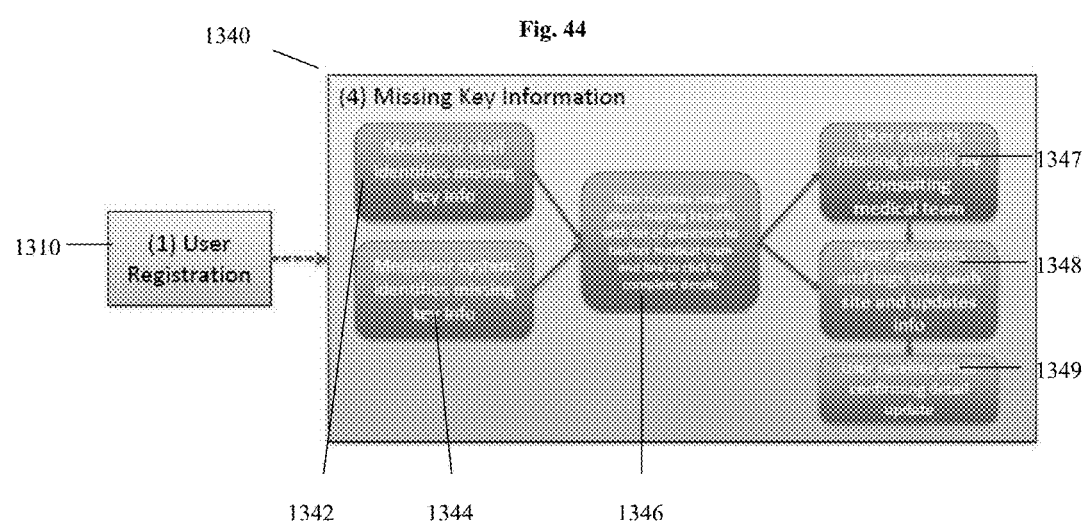
FIG. 44 illustrates features of some embodiments of the present invention.
Figure 45:
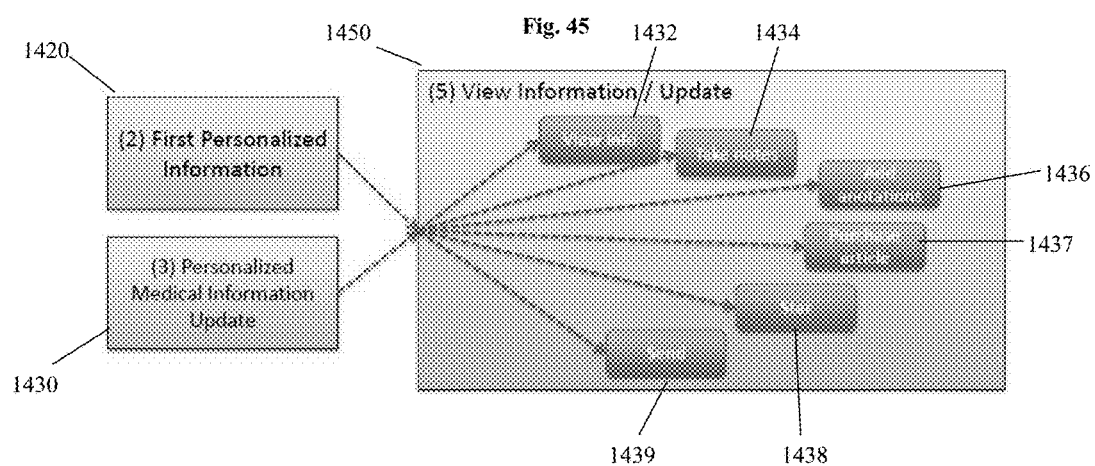
FIG. 45 illustrates features of some embodiments of the present invention.
Figure 46:
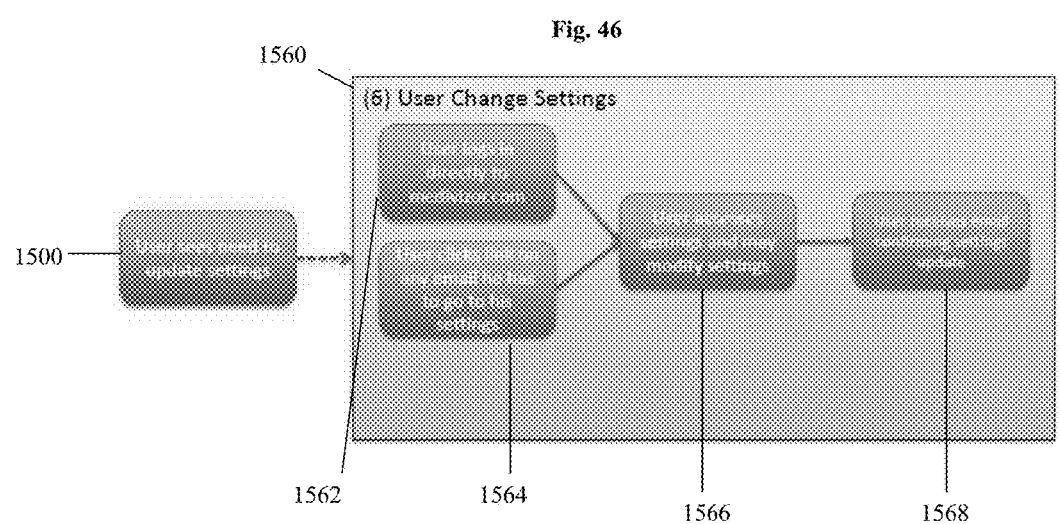
FIG. 46 illustrates features of some embodiments of the present invention.

The present invention will be further explained with reference to the attached drawings, wherein like structures are referred to by like numerals throughout the several views. The drawings shown are not necessarily to scale or aspect ratio, with emphasis instead generally being placed upon illustrating the principles of the present invention. Further, some features may be exaggerated to show details of particular components.

The figures constitute a part of this specification and include illustrative embodiments of the present invention and illustrate various objects and features thereof. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

DETAILED DESCRIPTION

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention which are intended to be illustrative, and not restrictive.

Throughout the specification and claims, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

In some embodiments, the term "information item" includes, but is not limited to, information about scientific research, medical research, news article, published thesis, draft thesis that becomes available, information about an event, a coverage of an event, a conference, a presentation, a poster, an abstract, a description of an event, information about a medical institution, information about a medical professional such as a doctor or surgeon or expert, a blog post, a comment in a blog post, a social media posting, a social network posting, an opinion, any information pertaining to one or more clinical trials, any information relating to healthcare or medical treatments, experimental treatments, new drugs, updated information about drugs, updated information about treatments, information about conventional or alternative medicine, medication, or ointment, a tip, a piece of advice, a warning, information from official or unofficial sources, lifestyle advice, health-related advice of any nature, nutrition information, physical activity or exercise information, sports information, information about psychology or psychiatry, information about generic or branded drugs, information about interactions between any of the above and/or other medical data.

In some embodiments, an "information item" may also include medical advice, personal advice, and/or self-help advice. In some embodiments, the term "advice" is defined as any tip, expert recommendation, peer recommendation, and/or a person's recommendation. In some embodiments, advice may be positive, negative, or neutral. In some embodiments, the advice may be positive, negative, or neutral as to any particular suggested or described course of action related to medical, health, and/or other topic.

In some embodiments, many forms of non-traditional advice may be considered, and may include words of wisdom, famous quotes, and/or concrete advice of treatment path for a particular user's related conditions. In some embodiments, an information item might be the original authorship of the information item, or any recounting of it by either the original author(s) or any others (person or entity)—such as an article covering it or reviewing it, summarizing it, explaining it or describing it. Both the original form and the coverage are considered information items.

In some embodiments, an information item may be in summary or in full form. In some embodiments, a summary may include, but is not limited to, a synopsis, abstract, summary, description, audio segment, video segment, a title, and/or a short text message. In some embodiments, full form or a more elaborate form may be the original form of the information item. In a non-limiting example, if the information item is published research, the information item may be the full text of the research. In a non-limiting example, if the source is a video interview, the information item may include the entire video of the interview.

In some embodiments, information items may include discrete or aggregate pieces of information. In some embodiments, a discrete information item may relate to, but is not limited to, specific event, a news item, an update item, an event, and/or a published article. In some embodiments, an aggregate information item may relate to more than one discrete information item. In some embodiments, an aggregate information item could include a description of several information items. In some embodiments, the information items may or may not be new. In some embodiments, the information item may be include a combination of new information and information that is not new. In some embodiments, the information items may be related or unrelated. In some embodiments, the information items may include different types of information items, including, but not limited to, aggregates, discrete, summary, full forms, original and/or coverage.

In some embodiments, an information item may be provided to the user in many ways and are synonymous for this purpose to providing information to the user of the system. In some embodiments, these equivalent methods include, but are not limited to, sending, bringing to the attention, notifying, emailing, sending text messages, sending instant messages, informing, alerting, paging, receiving, filtering, exposing, and/or presenting. In some embodiments, the information item may be entered, brought to the attention, provided, and/or emailed such that the user is notified and/or informed of the information item.

In some embodiments, information items can be provided to users in many different forms and either as individual information items or in various ways of grouping. In some embodiments, the information items can be described, for instance, as a list in one email or notification message or as individual information items.

In some embodiments, a user may be the person that is sick, injured, or healthy or a caregiver which may include, but is not limited to, a friend, family member, relative, paid help, a guardian, an advisor, or anybody caring for the individual. In some embodiments, a user may be any health care professional or any person involved in the activity of providing health care or any person that comes in contact with the system and/or any user of the system. In a non-limiting example, a healthcare professional would include, but not be limited to, a medical doctor, a nurse, an aid, a specialist, a technician, and/or an administrator. In some embodiments, a user may include any person involved in the health, medical, or well being of a person that is being cared for. In some embodiments, users may include, but are not limited to, indirect professionals, such as administrator, secretaries, employees of any company involved in the health care field, researchers, academics, and pharmaceutical company employees.

In some embodiments, "email" and/or "an email or a message" may include, but is not limited to, any form of message capable of conveying information in a similar way to a user and/or system. In some embodiments, this may include, but is not limited to, notification, instant message, SMS, text message, voice message, alarm, alert, warning, pop-up message, tip, email, fax, and/or physical mail.

In some embodiments, patients or one or more caregivers research the internet or other data sources for medical information. In some embodiments, medical professionals also research the internet or other data sources for medical information. In other embodiments, medical professionals are exposed to patients and/or one or more caregivers that research the internet for medical information.

In some embodiments, the present invention provides personalized medical information to a user. In some embodiments, a "user" may include, but is not limited to one or more patients, one or more care-givers, one or more medical personnel, and/or one or more relatives and/or friends of the one or more patients. In some embodiments, the information item is new or recently available. In some embodiments, the information item is relevant to the user. In some embodiments, the information item is provided in a manner so that it can be understood by the user. In some embodiments, the information item is provided in a manner so that the user can use the information for treatment or other medical purpose.

In some embodiments, the present invention provides personalized medical information to a user. In some embodiments, the information item includes information about the medical conditions and/or treatments relevant to the user.

In some embodiments, the present invention provides information items to a user based at least in part on the information provided by the user. In some embodiments, the present invention associates information items with the relevant users based on the information provided by the user. In some embodiments, invention associates information items with the relevant users based on the information provided in the Electronic Medical Record ("EMR"). In some embodiments, EMRs are referred to and used interchangeably with such terms as Electronic Health Record (EHR), Electronic Personal Record (EPR), or Personal Health Record (PHR). In some embodiments, invention associates information items with the relevant users based on the information provided by the user and in the EMR.

In some embodiments, the present invention is a dynamic, push system for providing information items. In some embodiments, the information item determined by the system of the present invention to be more relevant to the user is provided earlier.

In some embodiments, information items may be evaluated for the degree of relevance and/or classified into one or more levels. In some embodiments, the evaluation of the information item is conducted on a general basis. In some embodiments, the evaluation of the information item is conducted on an individual basis. In some embodiments, the information item may be classified into one of two or more degrees of relevance that may include irrelevant (and thus excluded) and/or relevant. In some embodiments, the information item is classified into one of four or more degrees of relevance that may include, but is not limited to, irrelevant, low, medium and/or high relevance. In some embodiments, this evaluation is conducted on an information item-by-information item basis. In some embodiments, this evaluation is conducted on a user-by-user basis.

In some embodiments, "relevance" is defined as the relation to the matter at hand. In some embodiments, the "relevance" may be used interchangeably with "degree of relevance". In some embodiments, an information item is ranked based on relevance or degree of relevance resulting in a relevance ranking.

In some embodiments, a degree of relevance may be associated with an information item. In some embodiments, the "degree of relevance" is the degree to which an information item or group of information items is relevant to a user and/or group of associated users. In some embodiments, the degree of relevance may be either dependent on or independent of parameters related to the user. In some embodiments, the degree of relevance is determined irrespective of the users. In some embodiments, the degree of relevance may be dependent, at least in part, on information related to the users.

In some embodiments, the degree of relevance is used interchangeably with relevance ranking. In some embodiments, relevance ranking may be used to rank, order, or prioritize the information items. In some embodiments, the degree of relevance or relevance ranking can be a parameter according to which information items are presented to the user.

In some embodiments, the degree of relevance may have one or more levels. In some embodiments, there may be one degree of relevance—either relevant or irrelevant. In some embodiments, there may be more than one degree of relevance, that may include, but is not limited to, relevant, partially/weakly relevant, irrelevant. In some embodiments, there may be more, such as a degree of relevance with any number of relevance. In some embodiments, relevance may be computed through a formula/equation based on association between the user's data/profile/medical record or account, and the information item. In some embodiments, information to guide this could include one or more parameters described herein.

In some embodiments, the degree of relevance may be used to determine which information items are provided or presented to the user and how they are provided or presented. In some embodiments, the degree of relevance may be used to order the information items are provided or presented. In some embodiments, the degree of relevance may be used to determine the way or method in which the information items are provided or presented. In some embodiments, the degree of relevance may be used to determine the frequency in which the information items are provided or presented. In some embodiments, the degree of relevance may be used to determine the prominence of each information item.

In some embodiments, the relevance of the information item is based on the individual. In some embodiments, the relevance of information item is based on information included in a user's profile. In some embodiments, the relevance of the information item is based on information in a user's profile such as the type of medical condition. In some embodiments, the relevance of the information item is based on a change in information in a user's profile. In some embodiments, the relevance of the information item is based on information in a user's profile such as gender, age, weight, height, BMI (Body Mass Index), smoking history, family history, medical history, general health, education level, reading level, IQ, current medical status, whether user is bedbound, or other information that may inform a decision regarding relevance of the information item. In some embodiments, the relevance of the information item is based on information in a user's profile such as location and/or demographic.

In some embodiments, the computer-implemented method includes receiving, by a computer system, current medical data from at least one electronic source; identifying, by the computer system, at least one medical-related filtering criterion related to an individual or a group of individuals; filtering, by the computer system, the current medical data based, at least in part, on at least one medical-related filtering criterion to identify current personalized medical data, where the current personalized medical data is related to the individual or the group of individuals; and presenting, by the computer system, the current personalized medical data to the individual or the group of individuals.

In some embodiments, the computer-implemented method further includes comparing, by the computer system, the current personalized medical data to past personalized medical data to identify that the past personalized medical data is obsolete in view of the current personalized medical data; and notifying, by the computer system, the individual or the group of individuals that the past personalized medical data is obsolete.

In some embodiments, the computer-implemented method further includes receiving, by the computer system, data associated with an individual or a group of individuals; and filtering, by the computer system, the current medical data based, at least in part, on the data associated with the individual or the group of individuals.

In some embodiments, the current medical data that includes health-related information relevant to at least one health condition of the individual or at least one health condition of the group of individuals.

In some embodiments, the current medical data includes at least one social media posting.

In some embodiments, the at least one medical-related filtering criterion is selected from the group of a demographic criterion, a health condition criterion, and a medical treatment criterion.

In some embodiments, the computer-implemented method further includes determining, by the computer system, a degree of relevance of discrete information within the current personalized medical data based on relevance to the individual or the group of individuals; and presenting, by the computer system, the discrete information within the current personalized medical data to the individual or the group of individuals according to the degree of relevance.

In some embodiments, the computer system includes at least one specially programmed computer module for receiving current medical data from at least one electronic source; identifying, by the computer system, at least one medical-related filtering criterion related to an individual or a group of individuals; filtering, by the computer system, the current medical data based, at least in part, on at least one medical-related filtering criterion to identify current personalized medical data, where the current personalized medical data is related to the individual or the group of individuals; and presenting the current personalized medical data to the individual or the group of individuals.

In some embodiments, the computer system further includes comparing the current personalized medical data to past personalized medical data to identify that the past personalized medical data is obsolete in view of the current personalized medical data; and notifying the individual or the group of individuals that the past personalized medical data is obsolete.

In some embodiments, the current medical data comprises health-related information relevant to at least one health condition of the individual or at least one health condition of the group of individuals.

In some embodiments, the current medical data comprises at least one social media posting.

In some embodiments, the at least one medical-related filtering criterion is selected from the group of a demographic criterion, a health condition criterion, and a medical treatment criterion.

In some embodiments, the computer system further includes determining a degree of relevance of discrete information within the current personalized medical data based on relevance to the individual or the group of individuals; and presenting the discrete information within the current personalized medical data to the individual or the group of individuals according to the degree of relevance.

In some embodiments, the computer program product embodied on a non-transitory computer readable medium includes computer code for receiving current medical data from at least one electronic source; identifying, by the computer system, at least one medical-related filtering criterion related to an individual or a group of individuals; filtering, by the computer system, the current medical data based, at least in part, on at least one medical-related filtering criterion to identify current personalized medical data, where the current personalized medical data is related to the individual or the group of individuals; and presenting the current personalized medical data to the individual or the group of individuals.

In some embodiments, the computer program product that includes the computer code for comparing the current personalized medical data to past personalized medical data to identify that the past personalized medical data is obsolete in view of the current personalized medical data; and notifying the individual or the group of individuals that the past personalized medical data is obsolete.

In some embodiments, the current medical data comprises health-related information relevant to at least one health condition of the individual or at least one health condition of the group of individuals.

In some embodiments, the at least one medical-related filtering criterion is selected from the group of a demographic criterion, a health condition criterion, and a medical treatment criterion.

In some embodiments, the computer program product further includes the computer code for determining a degree of relevance of discrete information within the current personalized medical data based on relevance to the individual or the group of individuals; and presenting the discrete information within the current personalized medical data to the individual or the group of individuals according to the degree of relevance.

In some embodiments, the system includes access to multiple medical data sources including, but not limited to, Twitter, Facebook, and/or other social media feed. In some embodiments, the system includes a subscription to RSS— Rich Site Summary providing access to various data sources, including, but not limited to, blogs, news, audio, video, and/or other social media feeds such as Twitter and/or Facebook. In some embodiments, the system includes receiving information through other means and sources including, but not limited to, email, application programming interfaces (APIs), Web Services, SOAP, REST, ebXML, and any other possible way to connect to other computer systems. In some embodiments, the present invention semantically classifies information items. In some embodiments, the present invention classifies, categorizes, tags and/or defines semantic association and/or classification. In some embodiments, the information may include, but is not limited to, information related to research, clinical trials, treatments, drugs, medicine, medication, or other information. In some embodiments, the information is classified by one or more medical experts, authors and/or publishers.

In some embodiments, the present invention may include, but is not limited to business development with publications, expert-powered in a Wikipedia model, crowd-powered by user's interactions with the system. In some embodiments, the user's interaction with the system of the present invention may include, but not limited to, reading, starring, highlighting, commenting, annotating, sharing, storing, saving, favoriting, ignoring, or other method of communication or action.

In some embodiments, the system filters the information based at least in part on the semantic classification and/or expert-sourced and/or crowd-sourced communications. In some embodiments, the present invention will include information items related to one or more medical conditions. In some embodiments, the present invention may include information items related to more than one medical condition.

In some embodiments, the system will include referrals related to clinical trials, treatments, experimental treatments, doctors, medical professionals, second opinions, drugs, procedures, surgery, operations, pharmaceuticals, and/or medical institutions. In some embodiments, the user may include, but is not limited to medical professionals. In some embodiments, the medical professionals will pay for access to the system. In some embodiments, the user will pay for a subscription to the system. In some embodiments, the user and/or medical professional will have free access to the system. In some embodiments, the user and/or medical professional will pay an amount per month for access to a predetermined number of information items per month. In some embodiments, the user and/or medical professional will pay $10 per month for access to three to five information items per month. In some embodiments, the user and/or medical professional will pay an amount per month for unlimited access to all information items. In some embodiments, the user and/or medical professionals will pay $30 per month for unlimited access to all information items. In some embodiments, the user and/or medical professionals can purchase individual information items.

In some embodiments, the system will include advertisements. In some embodiments, a commission will be paid for providing the information. In some embodiments, the system will be provided on a freemium basis. "Freemium" includes providing basics of the system free of charge while charging a premium for advanced features and/or functionality.

FIGS. 1-40 illustrate screen shots of some embodiments of the present invention. FIGS. 31-35 illustrate screen shots of metadata of some embodiments of the present invention.

FIGS. 41-48 illustrate methods of some embodiments of the present invention. Although the steps of the methods of the embodiments shown on FIGS. 41-48 are numbered, the steps may be performed in any order.

In some embodiments, the method of the present invention includes a user registration step 1010 that may include, but is not limited to, the substeps of user enters basic information 1012, user enters medical condition(s) 1014, and/or user enters treatment(s) 1016. The substeps may be performed in any order.

In some embodiments, the method of the present invention includes a personalized information step 1120 that may include, but is not limited to, the substeps of user receives email linked to web site area 1122, user accesses and logs into web site 1124, and user reads an information item 1126. The substeps may be performed in any order.

In some embodiments, the information item is generated by contributing medical experts or other qualified personnel to include, but not limited to, specifics related to medical conditions, treatment and/or basic information of the user. In some embodiments, the information item is personalized based on the information provided by the user during the user registration step and/or subsequent steps of the method. In some embodiments, information that is not relevant to the user is omitted.

In some embodiments, the method of the present invention includes a personalized medical information update step 1230 that may include, but is not limited to, the substeps of user receives an email about an update with a link 1232 and/or user accesses and logs into a website and reads an update 1230. The substeps may be performed in any order.

In some embodiments, information items are received from many sources including, but not limited to, medical journals, medical information databases, Twitter, RSS, WebMd®, Healthy Circles®, PubMed®, Patientslikeme®, clinicaltrials.gov, National Comprehensive Cancer Network ("NCCN"), National Institute of Health ("NIH"), cancer.net, National Cancer Institute, Society for Clinical Trials, Center for Disease Control ("CDC"), Sage®, NIH Clinical Trials Results via RSS or other means to obtain the information. In some embodiments, the information items are reviewed by medical experts to assess to which users it would be considered relevant. In some embodiments, information items considered relevant is determined factually based on the potential application to a user having an overall profile/medical condition. In some embodiments, the relevance of the information can be determined by the system based on inputs provided by the user, the reviewer, or any combination thereof based all or part on the users' profile, medical conditions, and/or treatments.

In some embodiments, the system of the present invention evaluates information items to determine relevance. In some embodiments, the system of the present invention is a computer system. In some embodiments, the users are notified via email or equivalent with the relevant, information items.

In some embodiments, the relevant, information items are presented to the user.

In some embodiments, the method of the present invention includes a missing key information step 1340 that may include, but is not limited to, the substeps of automatic or manual identifying missing key information 1342, 1344; user receives email about missing key information with list of questions to his/her medical team and link to click to complete details 1346; and user collects missing details by consulting medical team 1347 and/or user accesses and logs into web site and updates information 1348 and/or user receives email confirming the detail update 1349. The substeps may be performed in any order.

In some embodiments, the "key" information described above is information that that aids the system in distinguishing between relevant and irrelevant information. In an example, the present invention would request information related to a user's data feed and/or aid in determining the relevance of information. In some embodiments, the identification of "key" information can be based on an existing body of classified material.

In some embodiments, doctors and/or medical experts determine number and scope of questions to efficiently obtain the key information. In some embodiments, the number and scope of questions are based on historical system performance and/or historical classified information collected by the system.

In some embodiments, the missing key information step may be conducted independent of the user. In some embodiments, the missing key information step may be conducted to identify key missing details in the user's profile. In some embodiments, the missing key information step is conducted to allow for personalized updates.

In some embodiments, the method of the present invention includes a view information/update step 1450 that may include, but is not limited to, the substeps of viewing information 1320; taking notes 1434, adding annotations 1436, purchasing information items 1437, proposing changes to key information using a star or equivalent 1438, and sending proposed changes 1439. The substeps may be performed in any order.

In some embodiments, user actions or inactions may include, but are not limited to, ignore, skip, disregard, click, zoom in, star, send to another, save, print, make comments, annotation, highlights, note whether helpful or not, discuss, comment, share with others. Such user action or inaction represent clues to the system as to the relevance of an information item to people or users with some similarity. In some embodiments, the relevance of an information item is based on point/scoring system. In some embodiments, the relevance may be automatically applied to other similar users.

In some embodiments, the method of the present invention includes a user change setting step 1560 that may include, but is not limited to, the substeps of user logging into a website 1562 and/or the user clicking a link on an email 1564; and user accessing and/or modifying user settings 1566; and/or user receiving email confirmation settings have been updated 1568. The substeps may be performed in any order. In some embodiments, the user change setting step 1560 may include a step of user determining a need to update the settings 1500.

In some embodiments, the user determines the quantity and type of information provided by the system of the present invention.

In some embodiments, a user enters conditions, treatments, medical team, or other pertinent medical information and answers questions specific to the relevant conditions and/or treatments to further classify them. In some embodiments, new and/or recently published information is collected from public and private sources via a variety of feed collectors. In some embodiments, the source provider is prompted to classify the information items based on the potentially affected groups of potential users based on an ontology/data model. In some embodiments, the source provide is prompted to describe in basic terms the content of the information items.

In some embodiments, the classification of the information items is manually conducted by a human such as a medical expert. In some embodiments, the classification is automatically conducted by the system of the present invention. In some embodiments, the classification is automatically conducted by the system of the present invention using neuro-linguistic programming ("NLP") or equivalent.

A non-limiting example of a classification related to melanoma is shown below:

1. End User Syntax: Type of skin Cancer?
   1) Help Text: There are three different types of skin cancer: squamous cell carcinoma (SCC), basal cell carcinoma (BCC), and melanoma. The three types of cancer begin in the cells of the epidermis, the skin's upper layer. Which type were you diagnosed with?
   2) Condition: none
   3) End user association: no
   4) Question Type: top
   5) MD Syntax: same
   6) Top Answers: single
      i. Melanoma
      ii. Squamous cell carcinoma (SCC)
      iii. Basal cell carcinoma (BCC)
      iv. Merkel cell carcinoma
      v. I don't know
   7) Other Answers: none
2. End User Syntax: Localized [confined] or spread disease?
   1) Help Text: Early cancer is normally confined (localized) to the original tissue form which it developed. During later stages the cancer spreads outside its original site and may reach other tissues and even distant parts of the body.
   2) Condition: none
   3) End user association: no
   4) Question Type: top
   5) MD Syntax: Localized/Advanced
   6) Top Answers: single
      i. Confined [localized]
      ii. Spread [Advanced; Metastasized]
      iii. I don't know
   7) Other Answers: none
3. End User Syntax: Current stage?
   1) Help Text: A staging system is a standardized way for doctors to summarize information about how far a cancer has spread, and to adjust the appropriate treatment. Stage is usually expressed as a number on a scale of 0 through IV, with stage 0 describing non-invasive cancers that remain within their original location and stage IV describing invasive cancers that have spread to other parts of the body.
   2) Condition: none
   3) End user association: no
   4) Question Type: top
   5) MD Syntax: TNM Stage?
   6) Top Answers: single
      i. 0
      ii. I
         I
         IA
         IB
         Not sure re the sub-stage within I
      iii. II
         II
         IIA
         IIB
         IIC
         Not sure re the sub-stage within II
      iv. III
         III
         IIIA
         IIIB
         IIIC
         Not sure re the sub-stage within III
      v. IV
         IV
         IVA
         IVB
         Not sure re the sub-stage within IV
      vi. I don't know
   7) Other Answers: none
4. End User Syntax: Site/s of metastases?
   1) Help Text: Where do you currently have metastases?
   2) Condition: if "current stage"="IV"
   3) End user association: no
   4) Question Type: top
   5) MD Syntax: same
   6) Top Answers: multi-select
      i. I don't know
      ii. Single metastasis
      iii. Metastases to regional lymph nodes
      iv. Metastases to skin, subcutaneous, or distant lymph nodes
      v. Metastases to lung
      vi. Metastases to other visceral organs (e.g. liver) or distant sites (e.g. brain, bone)
   7) Other Answers: none
5. End User Syntax: Location?
   1) Help Text: Melanoma can occur anywhere on the skin, including the back and other hard-to-see areas that are not sun-exposed. It can also occur on the mucous membranes lining the mouth, nose, and genitals, or affect the eye (as in Ocular melanoma).
   2) Condition: if "Type of skin Cancer?"="Melanoma"
   3) End user association: no
   4) Question Type: required
   5) MD Syntax: Anatomic location
   6) Top Answers: single
      i. Skin melanoma
      ii. Mucosal melanoma (e.g. oral, gingival, digestive tract, urinary tract, genital)
      iii. Central nervous system [primary CNS, Spinal cord; meningeal; leptomeningeal; meningeal melanomatosis]
      iv. Ocular [Intraocular; eye; conjunctiva; Choroid; Ciliary body; uvea; iris; cornea; retinal]
      v. I don't know
   7) Other Answers: none
6. End User Syntax: BRAF molecular marker?
   1) Help Text: BRAF is a gene that makes a protein called B-RAF, which is involved in cancer cell growth. This gene may be mutated (changed) in different cancer cells, thereby increase their growth and spreading. Testing positive for the BRAF mutation means that your type of melanoma might be driven by a changed BRAF protein, which makes you eligible for BRAF targeted therapy.
   2) Condition: if "Type of skin Cancer?"="Melanoma"
   3) End user association: no
   4) Question Type: required
   5) MD Syntax: Mutated BRAF
   6) Top Answers: Single
      i. Positive
      ii. Negative
      iii. I don't know
   7) Other Answers: none
7. End User Syntax: Mitotic rate?
   1) Help Text: Your pathology report may contain information about the mitotic rate (MR). The MR is measured by simply examining the excised (surgically removed) tumor with a microscope and manually counting the number of dividing (mitotic) cells. The higher the mitotic count, the more likely the tumor is to have metastasized (spread). The logic is that the more cells are dividing, the more likely they will invade the blood or lymphatic vessels and thus spread around the body. What is the category or value of your MR?
2) Condition: if "Type of skin Cancer?"="Melanoma" and "tumor thickness?"="<1 mm"
3) End user association: no
4) Question Type: required
5) MD Syntax: same
6) Top Answers: single
   i. It wasn't tested
   ii. I don't know
   iii. <1/mm2
   iv. ≥1/mm2
7) Other Answers: none
8. End User Syntax: Performance status?
1) Help Text: The performance status is a measure of how well an individual suffering from cancer is. It takes into account the extent of symptoms of cancer, how comfortably an individual can perform daily activities, and how much help he or she requires for basic self-care. The performance status is measured by a performance score (scale of 0-4) that takes these factors into account.
2) Condition: none
3) End user association: yes
4) Question Type: required
5) MD Syntax: same
6) Top Answers: single
   i. 0—asymptomatic (Fully active, able to carry on all predisease activities without restriction)
   ii. 1—Symptomatic but completely ambulatory (Restricted in physically strenuous activity but ambulatory and able to carry out work of a light or sedentary nature. For example, light housework, office work)
   iii. 2—Symptomatic, <50% in bed during the day (Ambulatory and capable of all self care but unable to carry out any work activities. Up and about more than 50% of waking hours)
   iv. 3—Symptomatic, >50% in bed, but not bedbound (Capable of only limited self-care, confined to bed or chair 50% or more of waking hours
   v. 4—Bedbound (Completely disabled. Cannot carry on any self-care. Totally confined to bed or chair)
7) Other Answers: none
9. End User Syntax: Recurrent disease?
1) Help Text: A recurrent disease is a cancer that has been treated in the past, was cured partially or (seemingly) completely (referred to as 'remission'), and came back (relapsed).
2) Condition: none
3) End user association: no
4) Question Type: required
5) MD Syntax: Recurrences
6) Top Answers: Single
   i. No
   ii. Yes
7) Other Answers: none
10. End User Syntax: Tumor thickness? [Breslow thickness]
1) Help Text: This is defined as the total vertical height of the melanoma, from the very top to the area of deepest penetration into the skin. In general, the higher the Breslow thickness, the worse the prognosis (in terms of survival).
2) Condition: if "Type of skin Cancer?"="Melanoma"
3) End user association: no
4) Question Type: supplemental
5) MD Syntax: Breslow Thickness
6) Top Answers: Single
   i. It wasn't tested
   ii. I don't know
   iii. <1 mm
   iv. ≥1 mm
7) Other Answers: none
11. End User Syntax: Clark Level?
1) Help Text: The Clark level refers to how deep the tumor has penetrated into the layers of the skin.
2) Condition: if "Type of skin Cancer?"="Melanoma" and "tumor thickness?"="<1 mm"
3) End user association: no
4) Question Type: supplemental
5) MD Syntax: same
6) Top Answers: Single
   i. It wasn't tested
   ii. I don't know
   iii. Level I
   iv. Level II
   v. Level III
   vi. Level IV
   vii. Level V
7) Other Answers: none
12. End User Syntax: Ulceration?
1) Help Text: Ulceration is another prognostic parameter mentioned in the pathological report. It occurs when melanoma breaks through the overlying skin, meaning that blood vessels may come in touch with the melanoma cells, and the chances of tumor spread or re-occurrence are increased.
2) Condition: if "Type of skin Cancer?"="Melanoma" and "Subtype?"=("Superficial spreading" or "Lentigo maligna" or "Acral lentiginous (palmar/plantar and subungual)" or "Nodular" or "Desmoplastic" or "Verrucous" or "Nevoid" or "Solitary dermal")
3) End user association: no
4) Question Type: supplemental
5) MD Syntax: same
6) Top Answers: Single
   i. It wasn't tested
   ii. I don't know
   iii. Present
   iv. Not present
7) Other Answers: none
13. End User Syntax: Serum LDH level?
1) Help Text: LDH is a blood test that measures the amount of an enzyme in the blood called Lactate dehydrogenase (LDH). In general, the LDH level is measured in order to check for tissue damage, which elevates the normally low LDH level in the blood. For patients with melanoma, it is used to determine if the cancer has metastasized (spread) to organs beyond the skin or lymph nodes, usually to the liver or lungs. Although LDH is not specific for melanoma, it may be useful at diagnosis or to monitor post-surgery (adjuvant) treatment. The staging system for melanoma uses the LDH level to subdivide patients with stage IV disease.
2) Condition: if "Type of skin Cancer?"="Melanoma"
3) End user association: no
4) Question Type: supplemental
5) MD Syntax: tumor markers 6) Top Answers: multi-select
   i. It wasn't tested
   ii. I don't know
   iii. LDH levels
      Elevated
      Normal
      I don't know
7) Other Answers: none A non-limiting example of a classification related to lymphoma is shown below:

1. End User Syntax: Type of lymphoma?
   1) Help Text: Lymphoma is a type of cancer that begins in cells of the immune system. There are two basic categories of lymphomas. One kind is Hodgkin lymphoma, which is marked by the presence of a type of cell called the Reed-Sternberg cell. The other category is non-Hodgkin lymphomas, which includes a large, diverse group of cancers of immune system cells. Both Hodgkin and non-Hodgkin lymphomas can occur in children and adults. Which type of lymphoma have you been diagnosed with?
   2) Condition: none
   3) End user association: no
   4) Question Type: top
   5) MD Syntax: same
   6) Top Answers: single
      i. Hodgkin lymphoma (HL)
      ii. Non-Hodgkin lymphoma (NHL)
      iii. I don't know
   7) Other Answers: none
2. End User Syntax: Subtype of NHL?
   1) Help Text: The non-Hodgkin lymphomas (NHLs) are a diverse group of blood cancers that include any kind of lymphoma except Hodgkin's lymphomas.
   2) Condition: if "Type of lymphoma?"="Non-Hodgkin lymphoma (NHL)"
   3) End user association: no
   4) Question Type: top
   5) MD Syntax: same
   6) Top Answers: single
      i. Anaplastic large cell lymphoma
      ii. B-cell chronic lymphocytic leukemia (CLL)/Small lymphocytic lymphoma (SLL)
      iii. Diffuse large B-cell lymphoma (DLBCL)
      iv. Follicular lymphoma [nodular lymphoma]
      v. Follicular lymphoma (grade I and II)
      vi. Follicular lymphoma (grade III)
      vii. Mantle cell lymphoma
      viii. Marginal zone B-cell lymphoma
      ix. Mycosis fungoides
      x. Lymphoplasmacytic lymphoma
      xi. Peripheral T-cell lymphoma
      xii. Splenic marginal zone lymphoma
   7) Other Answers:
      i. Adult T-cell lymphoma/leukemia
      ii. Burkitt's lymphoma
      iii. Hairy cell leukemia
      iv. Natural killer cell large granular lymphocyte leukemia
      v. Plasma cell myeloma/plasmacytoma
      vi. Precursor B lymphoblastic leukemia/lymphoma
      vii. Precursor T lymphoblastic leukemia/lymphoma
      viii. T-cell large granular lymphocyte leukemia
      ix. T-cell prolymphocytic leukemia
      x. I don't know
3. End User Syntax: Does the lymphoma involve any of the following organs?
   1) Help Text: Lymphoma may arise in organs non related to the lymphatic system, such as the stomach, breast, nasal cavity etc.
   2) Condition: if "Type of lymphoma?"="Non-Hodgkin lymphoma (NHL)"
   3) End user association: no
   4) Question Type: top
   5) MD Syntax: same
   6) Top Answers: multi-select
      i. Stomach
      ii. Nasal cavity [nose]
      iii. Esophagus
      iv. Appendix
      v. Bladder
      vi. Trachea [windpipe]
      vii. Testicles
      viii. Sinuses
      ix. Small intestine
      x. Spinal cord
      xi. Ureters
      xii. Cecum [beginning of the large intestine]
      xiii. Colon [large intestine]
      xiv. Pancreas
      xv. Rectum
      xvi. Brain
      xvii. Liver
      xviii. Orbit [eye socket]
      xix. I don't know
   7) Other Answers: none
4. End User Syntax: Current stage?
   1) Help Text: Stage is usually expressed as a number on a scale of 1 through 4 (in Roman numerals). The lymphoma staging depends on both the place where the malignant tissue is located (as located with biopsy, CT scanning and positron emission tomography, PET) and on systemic symptoms due to the lymphoma ("B symptoms": night sweats, weight loss of >10% or fevers).
   2) Condition: none
   3) End user association: no
   4) Question Type: top
   5) MD Syntax: Ann Arbor staging
   6) Top Answers:
      i. I don't know
      ii. I—One lymph node or single organ
      iii. II—Two lymph nodes OR portion of tissue OR involves an organ and it's nearby lymph nodes
      iv. III—Upper & lower part: involves lymph nodes both above and below the diaphragm; OR one portion of tissue OR an organ near the lymph node groups OR in the spleen.
      v. IV—Extra nodular: Involves several portions of one or more organs and tissues
         0-1 organs
         2+
   7) Other Answers: none
5. End User Syntax: Confined or spread disease?
   1) Help Text: Early cancer is normally confined (localized) to the original tissue form which it developed. During later stages the cancer spreads outside its original site and may reach other tissues and even distant parts of the body.
   2) Condition: if "current stage"="I don't know"
   3) End user association: no
   4) Question Type: top
   5) MD Syntax: Localized/Advanced 6) Top Answers:
  i. Confined [localized]
  ii. Spread [Advanced; Metastasized]
  iii. I don't know
7) Other Answers: none
6. End User Syntax: Disease-related symptoms?
1) Help Text: The lymphoma staging depends on both the place where the malignant tissue is located (as located with biopsy, CT scanning and positron emission tomography, PET) and on systemic symptoms due to the lymphoma (such as night sweats, weight loss of >10% or fevers). Symptomatic staging is used by certain physicians only to denote if the disease causes symptoms directly.
2) Condition: none
3) End user association: no
4) Question Type: top
5) MD Syntax: symptomatic staging
6) Top Answers:
  i) I don't know
  ii) A=none of the lymphoma-related symptoms listed as 'B'
  iii) B=any one of:
    persistent fever >38° C. [100.4° F.] without other cause;
    unexplained loss of >10% of body weight over six months;
    the presence of drenching night sweats
  iv) E=the disease has spread from lymph nodes to adjacent tissues
  v) X=the largest deposit is >10 cm large ("bulky disease"), or the mediastinum is wider than ⅓ of the chest on a chest X-ray
  vi) S=the disease has spread to the spleen
7) Other Answers: none
7. End User Syntax: Current disease status?
1) Help Text: 'First-line' chemotherapy is the first regimen attempted in order to treat the lymphoma. Disease status is defined as either of four: (1) Opt for or currently undergoing first line therapy; (2) In remission—first-line therapy resulted in cure, meaning that there is no evidence of the lymphoma in imaging studies (usually CT or PET-CT); (3) Refractory disease—first-line therapy either failed to resolve the disease or produced intolerable side effects, and additional agents (second-line therapies) may be substituted or added to the treatment regimen; (4) In relapse—the lymphoma has been cured, and recently came back (re-appeared). How would you describe your current disease status?
2) Condition: if "Type of lymphoma?"="Non-Hodgkin lymphoma (NHL)"
3) End user association: no
4) Question Type: required
5) MD Syntax: same
6) Top Answers: single
  i) First line therapy
  ii) Remission
  iii) Refractory
  iv) Relapse
7) Other Answers: none
8. End User Syntax: Previously treated with bone marrow transplantation? [post transplant]
1) Help Text: Have you been previously treated by 'hematopoietic stem cell transplantation (HSCT)' or 'bone marrow transplantation' for your lymphoma?
2) Condition: treatment (past)
3) End user association: no
4) Question Type: required
5) MD Syntax: HSCT
6) Top Answers: Single
  i) No
  ii) Yes
  iii) I don't know
7) Other Answers: none
9. End User Syntax: Performance status?
1) Help Text: The performance status is a measure of how well an individual suffering from cancer is. It takes into account the extent of symptoms of cancer, how comfortably an individual can perform daily activities, and how much help he or she requires for basic self-care. The performance status is measured by a performance score (scale of 0-4) that takes these factors into account.
2) Condition: none
3) End user association: yes
4) Question Type: required
5) MD Syntax: same
6) Top Answers: single
  i. 0—asymptomatic (Fully active, able to carry on all predisease activities without restriction)
  ii. 1—Symptomatic but completely ambulatory (Restricted in physically strenuous activity but ambulatory and able to carry out work of a light or sedentary nature. For example, light housework, office work)
  iii. 2—Symptomatic, <50% in bed during the day (Ambulatory and capable of all self care but unable to carry out any work activities. Up and about more than 50% of waking hours)
  vi. 3—Symptomatic, >50% in bed, but not bedbound (Capable of only limited self-care, confined to bed or chair 50% or more of waking hours
  vii. 4—Bedbound (Completely disabled. Cannot carry on any self-care. Totally confined to bed or chair)
7) Other Answers: none
10. End User Syntax: Prognostic parameters?
1) Help Text: Both your age and LDH have prognostic significance in some subtypes of NHL. The serum lactate dehydrogenase (LDH) is an indicator of how much disease there is in the body. The more the disease, the more the value of LDH. Individuals with high levels of LDH in their blood do worse than those with normal levels. Younger age predicts better response to certain treatments for lymphoma.
2) Condition: if "Type of lymphoma?"="Non-Hodgkin lymphoma (NHL)"
3) End user association: no
4) Question Type: required
5) MD Syntax: IPI prognostic markers
6) Top Answers: multi-select
  i. LDH levels
    Elevated
    Normal
    I don't know
  ii. Age
    ≤60
    ≥60
7) Other Answers: none A non-limiting example of a classification related to breast cancer is shown below:
1. End User Syntax: Type of Breast Cancer?
1) Help Text: There are different types of breast cancer, including non-invasive (example: DCIS), and invasive (example: IDC). Which type were you diagnosed with? (Some of the following types are describes as 'subtype' in the pathology report)
2) Condition: none
3) End user association: no.
4) Question Type: top
5) MD Syntax: same
6) Top Answers: multi-select
   i. I don't know
   ii. Breast carcinoma [Adenocarcinoma]
   iii. Ductal carcinoma
      Ductal carcinoma in situ (DCIS) [Intraductal carcinoma]
      Infiltrating/invasive ductal carcinoma (IDC)
   iv. Lobular carcinoma
      Lobular Carcinoma in situ (LCIS) [Intralobular carcinoma]
      Invasive lobular carcinoma (ILC)
   v. Invasive ductal/lobular carcinoma
   vi. Atypical Ductal Hyperplasia (ADH)
   vii. Atypical Lobular Hyperplasia (ALH)
7) Other Answers:
   i. Fibroadenoma
   ii. Mucinuous [colloid]
   iii. Cribriform
   iv. Tubular
   v. Medullary
   vi. Papillary
   vii. Apocrine
   viii. Paget disease of breast (PDB)
   ix. Phyllodes tumor of breast
   x. Metaplastic
   xi. Invasive Micropapillary
   xii. Adenoid cystic
   xiii. Scirrhous
   xiv. Eccrine spiradenoma
   xv. Sarcoma
   xvi. Breast lymphoma
   xvii. Neuroendocrine
   xviii. Lipoma
   xix. Liposarcoma
   xx. Fibrosarcoma
   xxi. Squamous cell carcinoma
   xxii. Rhabdomyosarcoma
   xxiii. Angiosarcoma
   xxiv. Leiomyosarcoma
   xxv. Mucoepidermoid carcinoma
   xxvi. Signet ring cell adenocarcinoma
   xxvii. Secretory carcinoma
2. End User Syntax: Menopausal status?
1) Help Text: Early cancer is normally confined (localized) to the original tissue form which it developed. During later stages the cancer spreads outside its original site and may reach other tissues and even distant parts of the body.
2) Condition: none
3) End user association: no
4) Question Type: top
5) MD Syntax: same
6) Top Answers: single
   i. I don't know
   ii. Premenopausal
   iii. Menopausal
   iv. Postmenopausal
7) Other Answers: none 3. End User Syntax: Confined or spread disease?
1) Help Text: Early cancer is normally confined (localized) to the original tissue form which it developed. During later stages the cancer spreads outside its original site and may reach other tissues and even distant parts of the body.
2) Condition: none
3) End user association: no
4) Question Type: top
5) MD Syntax: Localized/Advanced [Involves lymph nodes or metastases]
6) Top Answers: single
   i. I don't know
   ii. Confined only to the breast [localized]
      Tumor size ≤2 cm
      Tumor size >2 cm but ≤5 cm
      Tumor size >5 cm
   iii. Tumor extends beyond the breast and into the skin or chest wall [Ulceration or skin nodules]
   iv. Spread into regional lymph nodes (around the breast or armpit)
      One involved lymph node (at the same side as the involved breast)
      More than 1 but less than 4 lymph nodes involved (at the same side as the involved breast)
      Four or more lymph nodes involved (at the same side as the involved breast)
   v. Spread to distant sites outside lymph nodes [Advanced; Metastasized]
7) Other Answers: none
4. End User Syntax: Current stage?
1) Help Text: A staging system is a standardized way for doctors to summarize information about how far a cancer has spread, and to adjust the appropriate treatment. Stage is usually expressed as a number on a scale of 0 through IV, with stage 0 describing non-invasive cancers that remain within their original location and stage IV describing invasive cancers that have spread to other parts of the body.
2) Condition: if "confined or spread disease"="I don't know"
3) End user association: no
4) Question Type: top
5) MD Syntax: TNM Stage?
6) Top Answers: single
   i. 0
      0
      Tis (DCIS)
      Tis (LCIS)
      Tis (Paget's)
      Not sure re the sub-stage within 0
   ii. I
      I
      IA
      IB
      Not sure re the sub-stage within I
   iii. II
      II
      IIA
      IIB
      Not sure re the sub-stage within II
   iv. III
      III
      IIIA
      IIIB
      IIIC
      Not sure re the sub-stage within III v. Inflammatory breast cancer
vi. IV
vii. I don't know
7) Other Answers: none
5. End User Syntax: Site/s of metastases?
1) Help Text: Where do you currently have metastases?
2) Condition: if "current stage"="IV"
3) End user association: no
4) Question Type: top
5) MD Syntax: same
6) Top Answers: multi-select
   i. I don't know
   ii. Single site
   iii. Metastases to soft tissues (e.g. chest wall)
   iv. Metastases to liver
   v. Metastases to lung
   vi. Bone metastases
   vii. Brain metastases
   viii. Metastases to endocrine organs (e.g. adrenal or pituitary gland)
   ix. Distant lymph nodes
7) Other Answers: none
6. End User Syntax: Hormone receptor status?
1) Help Text: Your pathology report will include the results of a hormone receptor assay, a test that tells you whether or not the breast cancer cells have receptors for the hormones estrogen and progesterone. Hormone receptors are proteins—found in and on breast cells—that pick up hormone signals telling the cells to grow. A cancer is called estrogen-receptor-positive (or ER+) if it has receptors for estrogen. Breast cancer cells that are ER+ depend on estrogen to grow, which makes them target for anti-estrogen hormonal therapy. Similarly, a cancer is called progesterone-receptor-positive (or PR+) if it has receptors for progesterone. The hormone receptor status is used for treatment decisions as well as for follow-ups.
2) Condition: none
3) End user association: no
4) Question Type: top
5) MD Syntax: same
6) Top Answers: single
   i. Positive (ER/PR+)
   ii. Negative (ER/PR)
   iii. I don't know
7) Other Answers: none
7. End User Syntax: HER2 status?
1) Help Text: HER2 (human epidermal growth factor receptor 2) is a protein that plays a role in the development of breast cancer. Your pathology report should include information about HER2 status, which tells you whether or not the breast cancer cells have the HER2. Breast cancers with HER2 gene amplification or HER2 protein overexpression are called HER2-positive in the pathology report. HER2-positive breast cancers tend to grow faster and are more likely to spread and come back compared to HER2-negative breast cancers, but there are medicines specifically for HER2-positive breast cancers.
2) Condition: none
3) End user association: no
4) Question Type: top
5) MD Syntax: same
6) Top Answers: single
   i. Positive
   ii. Negative
   iii. I don't know
7) Other Answers: none
8. End User Syntax: Current treatment status?
1) Help Text: Many women diagnosed with breast cancer are treated surgically. Surgery may be preceded or followed by other, systemic (body-wide), treatments, such as chemotherapy, hormonal therapy or radiation. A patient is considered in 'remission' if therapy resulted in cure, meaning that there is no evidence of the cancer in imaging studies (MRI, US, mammograms); a patient is 'refractory' if therapy either failed to resolve the disease or produced intolerable side effects, and additional agents may be substituted or added to the treatment regimen. A recurrent disease is a cancer that has been treated in the past, was cured (in remission), and came back (relapsed). In relation to the abovementioned options, what is your current treatment status?
2) Condition: none
3) End user association: no
4) Question Type: top
5) MD Syntax: same
6) Top Answers: multi-select
   i. I don't know
   ii. Pre-operative (before surgery)
   iii. Post-operative (after surgery)
   iv. In remission
   v. Refractory
   vi. In relapse [recurrent disease]
7) Other Answers: none
9. End User Syntax: Current treatment status?
1) Help Text: Women diagnosed with breast cancer are offered one of the following treatments: (1) Neoadjuvant therapy—a systemic (body-wide) treatment sometimes given as a step to shrink a tumor before surgery. Examples of neoadjuvant therapy include chemotherapy, and hormone therapy; (2) Surgery—many patients with breast cancer have surgery to remove the cancer from the breast. 'Lumpectomy' is a surgery to remove a tumor (lump) and a small amount of normal tissue around it. 'Total mastectomy' means surgery to remove the entire breast that has cancer. 'Radical mastectomy' (or 'modified radical mastectomy') involves the removal of both breast tissue and lymph nodes. Mastectomy procedures can be done with or without reconstruction; (3) Adjuvant therapy—systemic anti-cancer treatment that is given after surgery. Adjuvant therapy may include chemotherapy, radiation therapy, hormone therapy, targeted therapy, or biological therapy. Which of the abovementioned treatments are now being considered?
2) Condition: none
3) End user association: no
4) Question Type: top
5) MD Syntax: same
6) Top Answers: multi-select
   i. I don't know
   ii. Lumpectomy [wide excision, quadrantectomy, partial mastectomy, segmental mastectomy]
   iii. Total mastectomy
   iv. Radical mastectomy
   v. Breast reconstruction
   vi. Chemotherapy
   vii. Radiation
   viii. Hormonal therapy (e.g. Aromasin, Arimidex, Tamoxifen)
   ix. Biological therapy (Herceptin)
7) Other Answers: none 10. End User Syntax: Performance status?
1) Help Text: The performance status is a measure of how well an individual suffering from cancer is. It takes into account the extent of symptoms of cancer, how comfortably an individual can perform daily activities, and how much help he or she requires for basic self-care. The performance status is measured by a performance score (scale of 0-4) that takes these factors into account.
2) Condition: If "current stage"="IV" or "confined or spread disease"="Spread to distant sites outside lymph nodes"
3) End user association: yes
4) Question Type: required
5) MD Syntax: same
6) Top Answers: single
   i. 0—asymptomatic (Fully active, able to carry on all predisease activities without restriction)
   ii. 1—Symptomatic but completely ambulatory (Restricted in physically strenuous activity but ambulatory and able to carry out work of a light or sedentary nature. For example, light housework, office work)
   iii. 2—Symptomatic, <50% in bed during the day (Ambulatory and capable of all self care but unable to carry out any work activities. Up and about more than 50% of waking hours)
   iv. 3—Symptomatic, >50% in bed, but not bedbound (Capable of only limited self-care, confined to bed or chair 50% or more of waking hours
   v. 4—Bedbound (Completely disabled. Cannot carry on any self-care. Totally confined to bed or chair)
7) Other Answers: none
11. End User Syntax: Grade?
1) Help Text: Grade is a 'score' that tells you how different the cancer cells' appearance and growth patterns are from those of normal, healthy breast cells. Your pathology report will rate the cancer on a scale from 1 to 3.
2) Condition: none
3) End user association: no
4) Question Type: supplemental
5) MD Syntax: same
6) Top Answers: single
   i. It wasn't tested
   ii. I don't know
   iii. 1 [Low]
   iv. 2 [Intermediate]
   v. 3 [High]
7) Other Answers: none
12. End User Syntax: Blood marker tests?
1) Help Text: Your doctor may order blood tests for tumor markers to detect cancer activity in the body. A cancer tumor often produces a specific protein in the blood that serves as a marker for that cancer, and can be measured with simple blood tests. Markers that may be tested include urokinase plasminogen activator (uPA), and plasminogen activator inhibitor 1 (PAI-1). uPA and PAI-1 are prognostic markers that help determine the risk for recurrence and choice of treatment.
2) Condition: none
3) End user association: no
4) Question Type: supplemental
5) MD Syntax: uPA and PAI-1 marker test
6) Top Answers: single
   i. It wasn't tested
   ii. I don't know
   iii. Low levels of both markers
   iv. High levels of both markers
7) Other Answers: none
13. End User Syntax: Rate of cell growth (Ki-67)?
1) Help Text: Your pathology report may include information about the rate of cell growth—what proportion of the cancer cells within the tumor are growing and dividing to form new cancer cells. A higher percentage suggests a faster-growing, more aggressive cancer, rather than a slower, "laid back" one. A test that can measure the rate of growth include the Ki-67. Ki-67 is a protein in cells that increases as they prepare to divide into new cells. A staining process can measure the percentage of tumor cells that are positive for Ki-67. The more positive cells there are, the more quickly they are dividing and forming new cells. In breast cancer, a result of less than 10% is considered low, 10-20% borderline, and high if over 20%.
2) Condition: none
3) End user association: no
4) Question Type: supplemental
5) MD Syntax: Ki-67 blood levels
6) Top Answers: Single
   i. It wasn't tested
   ii. I don't know
   iii. Low (<10%)
   iv. Borderline (10-20%)
   v. High (>20%)
7) Other Answers: none
14. End User Syntax: High risk profile?
1) Help Text: Certain genetic risk factors and other conditions increase your chances of getting breast cancer, thereby put you in a 'high risk' group. Do you have any of the following risk factors?
2) Condition: none
3) End user association: no
4) Question Type: required
5) MD Syntax: same
6) Top Answers: multi-select
   i. I don't know
   ii. Carrier of BRCA1 or BRCA2 inherited mutation
   iii. Hereditary cancerous syndromes (Li-Fraumeni syndrome, Ataxia Telangiectasia, Peutz-Jeghers syndrome, Cowden syndrome)
   iv. Family history of breast or ovarian cancer (at least one first-degree relative with cancer before the age of 50)
   v. Personal history of breast or ovarian cancer
   vi. Previous chest radiation
   vii. Hormone replacement therapy (before or during menopause)
7) Other Answers: none
15. End User Syntax: Genomic Assays (Oncotype DX and MammaPrint)?
1) Help Text: A genomic assay is a type of test that uses a sample of the breast cancer tissue to analyze the activity of a group of genes, rather than just a single gene. Knowing whether certain genes are present or absent, overly active or not active enough, can help doctors predict the risk of the breast cancer returning later. This can be helpful in making treatment decisions, such as whether or not chemotherapy should be part of the treatment plan. Two genomic assays are currently in use for breast cancer: Oncotype DX and MammaPrint. These tests are reserved for a selective group of patients that fulfill certain criteria.
2) Condition: if "Type of Breast Cancer?" !=("Ductal carcinoma in situ (DCIS)" or "Lobular Carcinoma in situ (LCIS)") and ("Current stage?"="I" or "II") and ("Confined or spread disease?"="Spread into regional lymph nodes (around the breast or armpit)")
3) End user association: no
4) Question Type: supplemental
5) MD Syntax: Gene expression profile (GEP)
6) Top Answers: multi-select
  i. It wasn't tested
  ii. I don't know
  iii. Oncotype DX (21-gene recurrence score)
  iv. MammaPrint (Amsterdam 70-gene prognostic profile)
7) Other Answers: none
16. End User Syntax: Current pregnancy or lactation?
1) Help Text: Are you currently pregnant or breastfeeding (while being treated for breast cancer)?
2) Condition: none
3) End user association: no
4) Question Type: supplemental
5) MD Syntax: same
6) Top Answers: multi-select
  i. I don't know
  ii. I'm pregnant
  iii. I'm breastfeeding
  iv. Neither
7) Other Answers: none A non-limiting example of a classification related to prostate cancer is shown below:

1. End User Syntax: Type of prostate cancer?
1) Help Text: Several types of cells are found in the prostate, but many prostate cancers develop from the gland cells, and referred to as adenocarcinoma. However, there are other rare types of prostate cancer. Which type of prostate cancer have you been diagnosed with?
2) Condition: none
3) End user association: no
4) Question Type: top
5) MD Syntax: same
6) Top Answers: single
  i. I don't know
  ii. Adenocarcinoma
7) Other answers:
  i. Sarcoma
  ii. Small cell carcinoma
  iii. Transitional cell carcinoma
  iv. Squamous cell carcinoma
  v. Malignant phyllodes tumor
  vi. Neuroendocrine tumor
  vii. Acinar cell carcinoma
  viii. Embryonal rhabdomyosarcoma
  ix. Transitional cell carcinoma
  x. Sarcoma
  xi. Angiosarcoma
  xii. Adenoid cystic carcinoma
  xiii. Leiomyosarcoma
  xiv. Small cell carcinoma
  xv. Stromal sarcoma
2. End User Syntax: Confined or spread disease?
1) Help Text: Early cancer is normally confined (localized) to the original tissue form which it developed. During later stages the cancer spreads outside its original site and may reach other tissues and even distant parts of the body.
2) Condition: none
3) End user association: no
4) Question Type: top
5) MD Syntax: Localized/Advanced 6) Top Answers: single
  i. Confined to the prostate gland [localized]
  ii. Spread to regional lymph nodes (near the prostate)
  iii. Spread to distant sites [Advanced; Metastasized]
  iv. I don't know
7) Other Answers: none
3. End User Syntax: Current stage?
1) Help Text: A staging system is a standardized way for doctors to summarize information about how far a cancer has spread, and to adjust the appropriate treatment. Stage is usually expressed as a number on a scale of 0 through IV, with stage 0 describing non-invasive cancers that remain within their original location and stage IV describing invasive cancers that have spread to other parts of the body.
2) Condition: none
3) End user association: no
4) Question Type: top
5) MD Syntax: TNM Stage?
6) Top Answers: single
  i. I don't know
  ii. I
  iii. II
    IIA
    IIB
    Not sure re the sub-stage within II
  iv. III
  v. IV
7) Other Answers: none
4. End User Syntax: Highest Gleason grade at time of diagnosis?
1) Help Text: Pathologists grade prostate cancers according to the Gleason system. This system assigns a Gleason grade, using numbers from 1 to 5 based on how much the cells in the cancerous tissue look like normal prostate tissue. The higher the Gleason grade, the more likely the tumor is to behave aggressively (grow faster). Please provide the maximal Gleason grade from the pathology report.
2) Condition: if "Type of prostate cancer?"="Adenocarcinoma"
3) End user association: no
4) Question Type: required
5) MD Syntax: same
6) Top Answers:
  i. I don't know
  ii. 1
  iii. 2
  iv. 3
  v. 4
  vi. 5
7) Other answers: none
5. End User Syntax: Gleason score at time of diagnosis?
1) Help Text: Pathologists grade prostate cancers according to the Gleason system. This system assigns a Gleason grade, using numbers from 1 to 5 based on how much the cells in the cancerous tissue look like normal prostate tissue. The higher the Gleason grade, the more likely the tumor is to behave aggressively (grow faster). The Gleason score is the cumulative score from all samples taken. Please provide the total Gleason score from the pathology report.
2) Condition: if "Type of prostate cancer?"="Adenocarcinoma"
3) End user association: no
4) Question Type: required
5) MD Syntax: same 6) Top Answers:
   I don't know
   ≤6=well-differentiated [low-grade]
   7=moderately differentiated [intermediate-grade]
   8-10=poorly differentiated [high-grade]
7) Other answers: none
6. End User Syntax: PSA level?
1) Help Text: Prostate-specific antigen (PSA) is a substance made by cells in the prostate gland (both normal cells and cancer cells). PSA is often found in semen, but a small amount is also found in the blood. Many healthy men have levels under 4 nanograms per milliliter (ng/mL) of blood. The chance of having prostate cancer goes up as the PSA level goes up.
2) Condition: if "Type of prostate cancer?"="Adenocarcinoma"
3) End user association: no
4) Question Type: required
5) MD Syntax: same
6) Top Answers:
   i) I don't know
   ii) <4 ng/ml
   iii) 4≥PSA<10 ng/ml
   iv) 10≥PSA<20
   v) ≥20 ng/ml
7) Other answers: none
7. End User Syntax: Performance status?
1) Help Text: The performance status is a measure of how well an individual suffering from cancer is. It takes into account the extent of symptoms of cancer, how comfortably an individual can perform daily activities, and how much help he or she requires for basic self-care. The performance status is measured by a performance score (scale of 0-4) that takes these factors into account.
2) Condition: none
3) End user association: yes
4) Question Type: required
5) MD Syntax: same
6) Top Answers: single
   i. 0—asymptomatic (Fully active, able to carry on all predisease activities without restriction)
   ii. 1—Symptomatic but completely ambulatory (Restricted in physically strenuous activity but ambulatory and able to carry out work of a light or sedentary nature. For example, light housework, office work)
   iii. 2—Symptomatic, <50% in bed during the day (Ambulatory and capable of all self care but unable to carry out any work activities. Up and about more than 50% of waking hours)
   iv. 3—Symptomatic, >50% in bed, but not bedbound (Capable of only limited self-care, confined to bed or chair 50% or more of waking hours
   v. 4—Bedbound (Completely disabled. Cannot carry on any self-care. Totally confined to bed or chair)
7) Other Answers: none
8. End User Syntax: Recurrent disease?
1) Help Text: A recurrent disease is a cancer that has been treated in the past, was cured partially or (seemingly) completely (referred to as 'remission'), and came back (relapsed).
2) Condition: none
3) End user association: no
4) Question Type: required
5) MD Syntax: Recurrences
6) Top Answers: Single
   i. No
   ii. Yes
   iii. Yes, once
   iv. Yes, more than once
7) Other Answers: none
9. End User Syntax: Current treatment status?
1) Help Text: Men diagnosed with prostate cancer may be offered one or more of the following treatments: (1) Surgery to remove the prostate gland (radical prostatectomy); (2) Radiation therapy, including brachytherapy (where a source of radiation is directly inserted into the prostate gland) and proton therapy (uses a beam of protons instead of x-rays, to destroy cancer cells); (3) Surveillance—if you are older, or your cancer detected at a very early stage, your doctor may delay treatment and only monitor the cancer with PSA tests and biopsies; (4) If the prostate cancer has spread, treatment may include hormone therapy (medicines to reduce testosterone levels), surgery, or chemotherapy (cancer-killing drugs). Which of the abovementioned therapies are you opt for, or currently undergoing?
2) Condition: none
3) End user association: no
4) Question Type: required
5) MD Syntax: Recurrences
6) Top Answers: multi-select
   i. Surveillance
   ii. Radical prostatectomy
   iii. External beam radiation
   iv. Brachytherapy
   v. Proton therapy
   vi. Surgery for metastatic (spread) disease
   vii. Chemotherapy
   viii. Hormonal therapy (including Abiraterone)
   ix. Immunotherapy
   x. Supportive (palliative) care (for symptom relief)
   xi. Biological therapy (e.g. Avastin)
   xii. Steroids
7) Other Answers: none A non-limiting example of a classification related to diabetes mellitus is shown below:
1. End User Syntax: Type of diabetes, or 'prediabetes'?
1) Help Text: There are three main types of Diabetes: type 1, type II and gestational (onset during pregnancy). Prediabetes is the state in which some but not all of the diagnostic criteria for diabetes are met. Prediabetes is defined as either impaired fasting glucose (IFG), 100≤fasting glucose≥125 mg/dl; impaired glucose tolerance (IGT), two-hour glucose levels of 140-199 mg/dL; or as 5.7%≤HbA1C≥6.4% in a person NOT previously diagnosed with diabetes.
2) Condition: none
3) End user association: no
4) Question Type: top
5) MD Syntax: same
6) Top Answers: multi-select
   i. Prediabetes
   ii. Type I [insulin-dependent diabetes; juvenile diabetes]
      Immune-mediated
      Idiopathic [type 1B]
   iii. Type II [adult-onset diabetes]
      Non-insulin dependent
      Insulin dependent
   iv. Gestational diabetes
   v. Drug related (induced) diabetes (e.g. steroids, diuretics, etc)
   vi. Genetic forms of diabetes (e.g. MODY)

vii. Endocrine disease-related (e.g. Cushing's, Acromegaly, etc)
viii. Pancreatic disease-related (e.g. pancreatitis, CF, pancreas resection, etc)
7) Other answers: none
2. End User Syntax: Recent HbA1C value?
1) Help Text: Hemoglobin A1C (HbA1C) is a blood test that shows what your average blood sugar level has been for the past 2 to 3 months. This test may be used to diagnose diabetes or to see whether diabetes treatment is effective.
2) Condition: "type of diabetes"="type I" or "type II" or "Drug induced diabetes" or "Idiopathic or type 1B".
3) End user association: no
4) Question Type: top
5) MD Syntax: HbA1C
6) Top Answers: single
   i. I don't know
   ii. HbA1C<5.7%
   iii. 5.7%≤HbA1C≥6.4%
   iv. 6.5%≤HbA1C≥7%
   v. HbA1C>7%
7) Other answers: none
3. End User Syntax: Controlled (balanced) or uncontrolled diabetes?
1) Help Text: Diabetes is regarded as controlled if glycemic control is achieved by either target Hemoglobin A1C (HbA1C) maintained below 7%, or fasting plasma glucose below 126 mg/dl or random plasma glucose below 200 mg/dl. Otherwise, the condition is defined as uncontrolled.
2) Condition: if "Recent HbA1C value"="I don't know"
3) End user association: no
4) Question Type: required
5) MD Syntax: same
6) Top Answers: single
   i. I don't know
   ii. Controlled
   iii. Uncontrolled
7) Other answers: none
4. End User Syntax: Diabetes-related complications?
1) Help Text: Long term Diabetes may damage the nerves (neuropathy), eyes (retinopaty), and kidneys (nephropathy), and may also result in some well-known cardiovascular complications such as heart attacks or strokes.
2) Condition: none
3) End user association: yes
4) Question Type: required
5) MD Syntax: micro- and macrovascular complications
6) Top Answers: multi-select
   i. I don't know
   ii. Ischemic heart disease (previous heart attacks, coronary stents, angina)
   iii. Stroke (TIA or CVA)
   iv. Diabetic Neuropathy
      Diabetic foot (loss of feeling leading to severe foot injuries)
      Urinary incontinence (loss of bladder control)
      Erectile dysfunction
      Abnormal sensation to a body part
      Numbness and tingling of extremities
      Burning or electric pain
      Difficulty swallowing
   v. Diabetic nephropathy
      Edema: swelling, around the eyes, legs, or general body swelling
      Foamy appearance or excessive frothing of the urine (proteinuria)
      Chronic kidney disease (elevated levels of creatinine)
      End stage kidney disease requiring dialysis
   vi. Diabetic Retinopathy
      Macular edema
      Myopia (nearsightedness)
      Blindness
   vii. Diabetic vasculopathy [angiopathy]
      Yes
      No
      I don't know
7) Other answers: none
5. End User Syntax: Anti-diabetes medication?
1) Help Text: Unbalanced blood sugar, as well as certain hypoglycemic drugs may cause episodes of hypoglycemia. Have you suffered episodes of hypoglycemia more than once?
2) Condition: none
3) End user association: no
4) Question Type: required
5) MD Syntax: hypoglycemics
6) Top Answers: multi-select
   i) I don't know
   ii) Insulin
      Aspart (Novolong, Novorapid, Penfill)
      Glulisine (Apidra)
      Lispro (Humalog)
      Regular (Humulin R, Novolin R, Novolin R Innolet, Novolin R PenFill, ReliOn/Novolin R)
      Detemir (Levemir)
      Glargine (Lantus, Solostar)
      NPH (Humulin N, Novolin N, Novolin NPH, NPH Iletin II, isophane insulin)
   iii) Oral hypoglycemics
      Acetohexamide (Dymelor)
      Chlorpropamide (Diabinese)
      Tolazamide (Tolinase)
      Tolbutamide (Orinase)
      Glyburide
      Glyburide micronized (Glynase)
      Glyburide-diabeta (Diabeta)
      Glipizide (Glucotrol, Glucotrol XR)
      Glimepiride (Amaryl)
      Repaglinide (Prandin)
      Nateglinide (Starlix)
      Metformin (Glucophage)
      Metformin extended-release (Fortamet, Glucophage XR, Glumetza, Riomet)
      Pioglitazone (Actos)
      Rosiglitazone (Avandia)
      Acarbose (Precose)
      Miglitol (Glycet)
      glimepiride/pioglitazone (Duetact)
      glimepiride/rosiglitazone (Avandaryl)
      glipizide/metformin (Metaglip)
      glyburide/metformin (Glucovance)
      linagliptin/metformin (Jentadueto)
      pioglitazone/metformin (Actoplus Met)
      pioglitazone/metformin extended-release (Actoplus Met XR)
      repaglinide/metformin (Prandimet)
      rosiglitazone/metformin (Avandamet)
      saxagliptin/metformin extended-release (Kombiglyze XR)
      sitagliptin/metformin (Janumet)

sitagliptin/metformin extended-release (Janumet XR)
sitagliptin/simvastatin (Juvisync)
linagliptin (Tradjenta)
saxagliptin (Onglyza)
sitagliptin (Januvia)
Vildagliptin (Zomelis, Galvus)
Colesevelam (Welchol)
   iv) Hypoglycemics given by injection
      Exenatide (Byetta, Bydureon)
      Liraglutide (Victoza)
      Pramlintide (Symlin)
   7) Other answers: none
6. End User Syntax: Recurrent episodes of hypoglycemia?
   8) Help Text: Incorrect use of Insulin, as well as certain hypoglycemic drugs may cause episodes of hypoglycemia. Have you suffered episodes of hypoglycemia more than once?
   9) Condition: none
   10) End user association: no
   11) Question Type: required
   12) MD Syntax: recurrent hypoglycemia
   13) Top Answers: multi-select
      i. I don't know
      ii. No
      iii. Yes, more than once
      iv. Yes, many times
   14) Other answers: none
7. End User Syntax: Diabetes-related adverse events?
   1) Help Text: Unbalanced blood sugar may cause some serious adverse events, such as Diabetic Ketoacidosis (more common in type 1) or Hyperosmolar hyperglycemic state (in type 2). Have you ever suffered any of these events?
   2) Condition: none
   3) End user association: no
   4) Question Type: required
   5) MD Syntax: major complications
   6) Top Answers: multi-select
      i. I don't know
      ii. Diabetic Ketoacidosis (DKA)
         Yes
         No
         I don't know
      iii. Hyperosmolar hyperglycemic state (HHS)
         Yes
         No
         I don't know
   7) Other answers: none
8. End User Syntax: Other concurrent medical conditions?
   1) Help Text: none
   2) Condition: "type of diabetes"="type I" or "type II" or "Drug induced diabetes" or "Idiopathic or type 1B" or "gestational diabetes".
   3) End user association: yes
   4) Question Type: required
   5) MD Syntax: Co-morbidities
   6) Top Answers: multi-select
      i. Obesity (BMI ≥25 kg/m2)
      ii. Dyslipidemia (HDL ≤35 mg/dL and/or a triglyceride ≥250 mg/dL)
      iii. Hypertension
      iv. Smoking
      v. Polycystic ovary syndrome
      vi. History of vascular disease
      vii. Pregnancy
   7) Other answers: none
9. End User Syntax: Bariatric (weight-loss) surgery?
   1) Help Text: Bariatric surgery (weight-loss surgery) includes a variety of procedures performed on people who are obese. Weight loss is achieved by reducing the size of the stomach with an implanted medical device or through removal of a portion of the stomach or by resecting and re-routing the small intestines to a small stomach pouch (gastric bypass surgery).
   2) Condition: If "Other concurrent medical conditions"="Obesity (BMI ≥25 kg/m2)"
   3) End user association: yes
   4) Question Type: required
   5) MD Syntax: Co-morbidities
   6) Top Answers: multi-select
      i. Obesity (BMI ≥25 kg/m2)
      ii. Dyslipidemia (HDL ≤35 mg/dL and/or a triglyceride ≥250 mg/dL)
      iii. Hypertension
      iv. Smoking
      v. Polycystic ovary syndrome
      vi. History of vascular disease
      vii. Pregnancy
   7) Other answers: none
10. End User Syntax: Familial diabetic syndrome?
   1) Help Text: Refers to any of several hereditary forms of diabetes caused by mutations which are monogenic.
   2) Condition: none
   3) End user association: yes
   4) Question Type: supplemental
   5) MD Syntax: same
   6) Top Answers: multi-select
      i. I don't know
      ii. Maturity onset diabetes of the young (MODY)
         Yes
         No
         I don't know
      iii. Maternally inherited diabetes and deafness (MIDD)
         Yes
         No
         I don't know
      iv. Wolfram's syndrome
         Yes
         No
         I don't know
      v. Type A insulin resistance
         Yes
         No
         I don't know
      vi. Leprechaunism
         Yes
         No
         I don't know
      vii. Rabson-Mendenhall syndrome
         Yes
         No
         I don't know
      viii. Lipodystrophy syndromes
         Yes
         No
         I don't know
   7) Other answers: none
11. End User Syntax: Is your diabetes related to any of the following conditions?
   1) Help Text: Certain medical conditions may cause secondary diabetes. For example, pancreatic damage, removal or disease, as well as certain endocrine diseases. Do you have (or previously had) any of those conditions?
2) Condition: none
3) End user association: yes
4) Question Type: supplemental
5) MD Syntax: secondary diabetes
6) Top Answers: multi-select
   i. I don't know
   ii. Cystic fibrosis
      Yes
      No
      I don't know
   iii. Hemochromatosis
      Yes
      No
      I don't know
   iv. Chronic pancreatitis
      Yes
      No
      I don't know
   v. Cushing's syndrome
      Yes
      No
      I don't know
   vi. Acromegaly
      Yes
      No
      I don't know
   vii. Pheochromocytoma
      Yes
      No
      I don't know
   viii. Pancreatectomy
      Yes
      No
      I don't know
   ix. Fibrocalculous pancreatopathy
      Yes
      No
      I don't know
   x. Glucagonoma
      Yes
      No
      I don't know
   xi. Hyperthyroidism
      Yes
      No
      I don't know
   xii. Somatostatinoma
      Yes
      No
      I don't know
   xiii. Aldosteronoma
      Yes
      No
      I don't know
7) Other answers: none In some embodiments, the present invention includes the step of a user entering his/her profile that may include, but is not limited to, basic information such as age, date of birth, gender, ethnicity, and/or geographic home location, and/or one or more medical condition(s) from which he or she is suffering. In some embodiments, for each of the medical conditions the user is asked specific questions to further define when the medical condition started, whether the medical condition is diagnosed or suspected, who is treating them, where, and/or one or more questions specific to each medical condition. In some embodiments, the user is asked additional questions regarding the treatment the user is receiving such as whether the use had received the treatment in the past, currently, or planning to receive in the near or distant future. In some embodiments, treatments may include additional, more specific questions. In some embodiments, a "generalized medical condition" or "medical profile" is developed based on the information described above. The user's profile then guides the determination how the present invention matches information items with the user.

In some embodiments, the relevance of the information items is based on a pre-determined set of medical advice rules. In some embodiments, the system of the present invention identifies the relevance of the information items based, at least in part, on the medical advice rules. In some embodiments, the medical advice rules are based, at least in part, on information provided by medical experts.

In some embodiments, the medical advice rules that guide the classification of various information items are established at least in part by doctors and/or medical institutions. In some embodiments, the medical advice rules may be based, at least in part, on types of medical tests, treatment costs, status of clinical trials, types of alternative treatments available, potential side effects, or other pertinent medical information.

In some embodiments, the number of information items and the timing of the information items provided to a user may be limited based, at least in part, on the user's profile. In some embodiments, the number of information items and timing of the information items provided to a user may be limited based, at least in part, on the mobility status of the user such as whether the user is bedridden, the current mental capacity of the user such as the reading level of the user or whether the user has diminished mental capacity, and/or the user's current medical condition.

In some embodiments, the method of providing information items may be based, at least in part, on a user's profile including such information as current mobility and/or mental capacity. In some embodiments, the method of alerting the user regarding information items is based, at least in part, on the user's profile.

In some embodiments, a medical professional expert network associated with the medical field classifies and/or confirms the description of the information items. In some embodiments, the medical professional expert network also documents the relationship of the information items to other information items and/or identifies any differences contained in the information items.

In some embodiments, the users of the system of the present invention associated with the medical condition, treatment, and/or other situation for which the information item has been classified, are notified of the new information item. In some embodiments, the notification is conducted with an email, an item in the user's inbox, and/or a notification bubble on a dashboard and/or the calendar.

In some embodiments, users can view the information item and/or mark the item as favorite/like/tag/save, annotate, post a note and/or comment, or otherwise communicate the user's view of the information item.

In some embodiments, the activities of the users in relation to the information item ranks the information item for other users resulting in additional crowdsourcing.

In some embodiments, the relevance of the information item is crowdsourced for each user based on user mark ups, favorites, and any other user gesture including, but not limited to, ignoring, failure to read or other response that may indicate the relevance of the information item to other users.

In some embodiments, relevance of the information item to one or more users is determined using a set of condition-specific distinguishing characteristics.

In some embodiments, a mechanical turk is used to read information items and match the information items with one or more users. In some embodiments, the mechanical turk may include a person with little or no medical knowledge and/or a subject matter expert. In some embodiments, a "mechanical turk" is used to describe the human powering the machine. In some embodiments, a "mechanical turk" is used to describe a system where computer programmers co-ordinate the use of human intelligence and human power to perform tasks. In some embodiments, such tasks are not performed by the computer for any number of reasons including, but not limited to, tasks that computers are currently unable to complete, are ineffective or inefficient at performing, or are, for any other reason, not fully automated.

In some embodiments, information items are reviewed by humans to determine relevance to a user. In some embodiments, the system of the present invention reviews the information items to determine relevance or degree of relevance to a user. In some embodiments, the information items are reviewed by both the system of the present invention and humans to determine relevance to a user.

In some embodiments, the present invention may include scheduling appointments and/or other forms of referrals to communicate potentially relevant information items to one or more users. In some embodiments, the present invention may include, but is not limited to, selling full text of relevant information items. In some embodiments, the present invention may include, but is not limited to, selling full or partial text of one or more information items.

In some embodiments, the present invention may provide alerts regarding information item for medical professionals having one or more patients. In some embodiments, the alerts may include, but are not limited to, an avatar/profile pictures with notification bubbles indicating information items. In some embodiments, the alerts may be in the form of a dashboard.

In some embodiments, the notification of medical professionals is conducted based, at least in part, on the patients' medical conditions and/or medical records. In some embodiments, a user may provide approval for a second user such as a medical professional to receive and/or provide information items related to the user's medical condition.

In some embodiments, the system of the present invention removes relevant identification information from a profile. In some embodiments, the system of the present invention notifies a care taker and/or medical professional about an information item relevant to a user without identifying the user. In some embodiments, the system of the present invention notifies a care taker and/or medical professional about an information item relevant to a group of users without identifying the users. In some embodiments, the users may be group by age, weight, height, medical condition, mobility status, mental capacity, geographic location or other pertinent factor.

In some embodiments, the alerts may be associated with a meeting calendar. In some embodiments, the medical professionals may have an indicator of a new information item. In some embodiments, the medical professionals may receive updates regarding vitals. In some embodiments, the updates may be provided automatically and/or manually entered by patient, caregivers, and/or medical team. In some embodiments, the notification and/or alerts may be shown in color and/or symbol specific for the different types of updates.

In some embodiments, the present invention includes advice related to traditional and non-traditional medicine. In some embodiments, the present invention may include, but is not limited to, advice related to non-traditional medicine such as alternative medicine, less researched areas of medicine, and/or non-traditional areas of medicine. In some embodiments, the non-traditional medicine may include, but is not limited to, medical techniques and/or medicine not currently approved by a regulatory authority in a user's geographic area. In some embodiments, the non-traditional may include, but is not limited to, medical techniques and/or medicine currently in a clinical trials and/or under development. In some embodiments, the non-traditional medicine may include, but is not limited to, acupuncture, chiropractor-related medicine, or other non-traditional medicine.

In some embodiments, the present invention may also include suggestions for new tests and diagnostics that may or may not be relevant to further sub-distinguish condition. In some embodiments, the present invention may also include recommendation for a second opinion by an expert. In some embodiments, the recommendation by the expert may include, but is not limited to, effectively recommending the right doctor and/or medical institution for treatment of a medical condition and/or associating the recommendation with each user having that condition using each user's profile.

In some embodiments, experts crowdsource the differences between the information items to assess the scope of the new information. In some embodiments, the new information is explained by the delta between the new information and the previously described and/or annotated material. In some embodiments, the present invention allows for the creation and visualization of a map of relationships between information items.

In some embodiments, the present invention includes matching individuals to clinical trials. In some embodiments, the matching of individuals to clinical trials is based on relationship between the individual's condition to the clinical trial, geography and/or mobility.

In some embodiments, the present invention may include a "Healthy Keychain" solution for a patient to share medical information across a number of sites and/or aggregate the benefit from the various sites. In some embodiments, the "Healthy Keychain" may include, but is not limited to, a user having appropriate login/authentication credentials access to one or more other sources of medical data about an individual. In some embodiments, a system would allow another to access the system on behalf of the user to conduct activities that may include retrieving data, updating data, synchronizing data, etc. In some embodiments, the system would populate one or more other systems. In an example, a user that updated one or more aspects of his or her medical profile such as weight, medical condition, etc. in one system would automatically populate/synchronize with other systems. In some embodiments, new updates in a system such as lab test results could be retrieved from other systems and synchronized with still other systems.

In some embodiments, the patient and/or caregiver is responsible for providing medical information and associated data. In some embodiments, this is not practical for multiple services. In some embodiments, the present invention allows a one-time information gathering step. In some embodiments, the gathered information is spread across the sites that are potentially relevant for the user and/or personal agent.

In some embodiments, the present invention includes one or more referrals and/or feedback. In some embodiments, the present invention may include, but is not limited to a scheduling module and/or a priority in list/search.

In some embodiments, the present invention may include, but is not limited to automatic checking of symptoms and/or distinguishing between the side-effects of medication and/or treatment and the core illness and/or condition In some embodiments, the present invention may include filtering the information items by filtering the users to determine the relevance of the information items to the users. In some embodiments, the invention may include providing an information update to the users that may be conditionally constructed to be personalized for each user based on factors that may include, but are not limited to, specific demographic, medical conditions, and/or treatments.

In some embodiments, the present invention includes deprecating and/or rendering obsolete an information item. In some embodiments, the information item may be superseded by newer more accurate information. In some embodiments, the relevant users are notified that the superseded information required revision. In some embodiments, the obsolete and/or deprecated information will be stored.

In some embodiments, the present invention notifies any users that viewed the now obsolete or deprecated information regarding the status of the information. In some embodiments, new or more accurate information is distributed to any users that viewed the now obsolete or deprecated information. In some embodiments, the system automatically evaluates the new or more accurate information and notifies the pertinent users. In some embodiments, a human evaluates the new or more accurate information and manually notifies the pertinent users. In some embodiments, the notification is issued via electronic mail.

In some embodiments, information may become obsolete and/or deprecated due to a change in a user's profile. In some embodiments, information may become obsolete and/or deprecated due to a change in a user's profile such as change in medical condition, change in mobility, change in mental condition/reading ability, or other related change.

Illustrative Operating Environments

Figure 47:
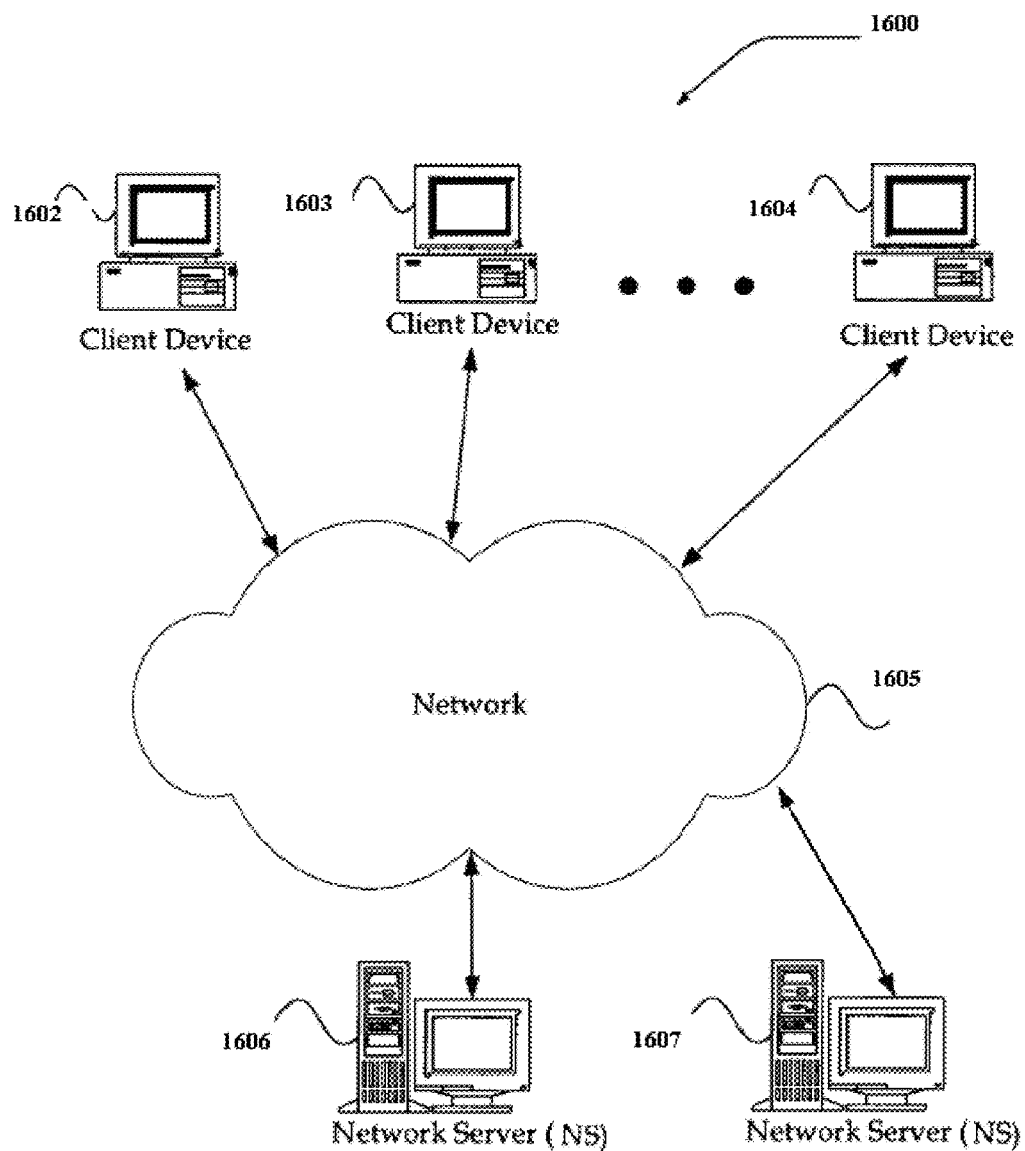
FIG. 47 illustrates features of some embodiments of the present invention.

FIG. 47 illustrates one embodiment of an environment in which the present invention may operate. However, not all of these components may be required to practice the invention, and variations in the arrangement and type of the components may be made without departing from the spirit or scope of the invention. In some embodiments, the inventive system and method may include a large number of members and/or concurrent transactions. In other embodiments, the inventive system and method are based on a scalable computer and network architecture that incorporates various strategies for assessing the data, caching, searching, and database connection pooling. An example of the scalable architecture is an architecture that is capable of operating multiple servers.

In embodiments, members of the inventive computer system 1602-1604 include virtually any computing device capable of receiving and sending a message over a network, such as network 1605, to and from another computing device, such as servers 1606 and 1607, each other, and the like. In embodiments, the set of such devices includes devices that typically connect using a wired communications medium such as personal computers, multiprocessor systems, microprocessor-based or programmable consumer electronics, network PCs, and the like. In embodiments, the set of such devices also includes devices that typically connect using a wireless communications medium such as cell phones, smart phones, pagers, walkie talkies, radio frequency (RF) devices, infrared (IR) devices, CBs, integrated devices combining one or more of the preceding devices, or virtually any mobile device, and the like. Similarly, in embodiments, client devices 1602-1604 are any device that is capable of connecting using a wired or wireless communication medium such as a PDA, POCKET PC, wearable computer, laptop, tablet, smartphone, netbook, desktop computer, and any other device that is equipped to communicate over a wired and/or wireless communication medium.

In embodiments, each member device within member devices 1602-1604 may include a browser application that is configured to receive and to send web pages, and the like. In embodiments, the browser application may be configured to receive and display graphics, text, multimedia, and the like, employing virtually any web based language, including, but not limited to Standard Generalized Markup Language (SGML), such as HyperText Markup Language (HTML), a wireless application protocol (WAP), a Handheld Device Markup Language (HDML), such as Wireless Markup Language (WML), WMLScript, XML, JavaScript, and the like. In embodiments, the invention is programmed in either Java, .Net, QT, C, C++, CSS, JavaScript, Ruby on Rails or other suitable programming language.

In embodiments, member devices 1602-1604 may be further configured to receive a message from another computing device employing another mechanism, including, but not limited to email, Short Message Service (SMS), Multimedia Message Service (MMS), instant messaging (IM), internet relay chat (IRC), mIRC, Jabber, Twitter, Facebook messages, a mobile application and the like or a Proprietary protocol.

In embodiments, network 1605 may be configured to couple one computing device to another computing device to enable them to communicate. In some embodiments, network 1605 may be enabled to employ any form of computer readable media for communicating information from one electronic device to another. Also, in embodiments, network 1605 may include a wireless interface, and/or a wired interface, such as the Internet, in addition to local area networks (LANs), wide area networks (WANs), direct connections, such as through a universal serial bus (USB) port, other forms of computer-readable media, or any combination thereof. In embodiments, on an interconnected set of LANs, including those based on differing architectures and protocols, a router may act as a link between LANs, enabling messages to be sent from one to another.

Also, in some embodiments, communication links within LANs typically include twisted wire pair or coaxial cable, while communication links between networks may utilize analog telephone lines, full or fractional dedicated digital lines including T1, T2, T3, and T4, Integrated Services Digital Networks (ISDNs), Digital Subscriber Lines (DSLs), wireless links including satellite links, or other communications links known to those skilled in the art. Furthermore, in some embodiments, remote computers and other related electronic devices could be remotely connected to either LANs or WANs via a modem and temporary telephone link. In essence, in some embodiments, network 1605 includes any communication method by which information may travel between client devices 1602-1604, and servers 1606 and 1607.

Figure 48:
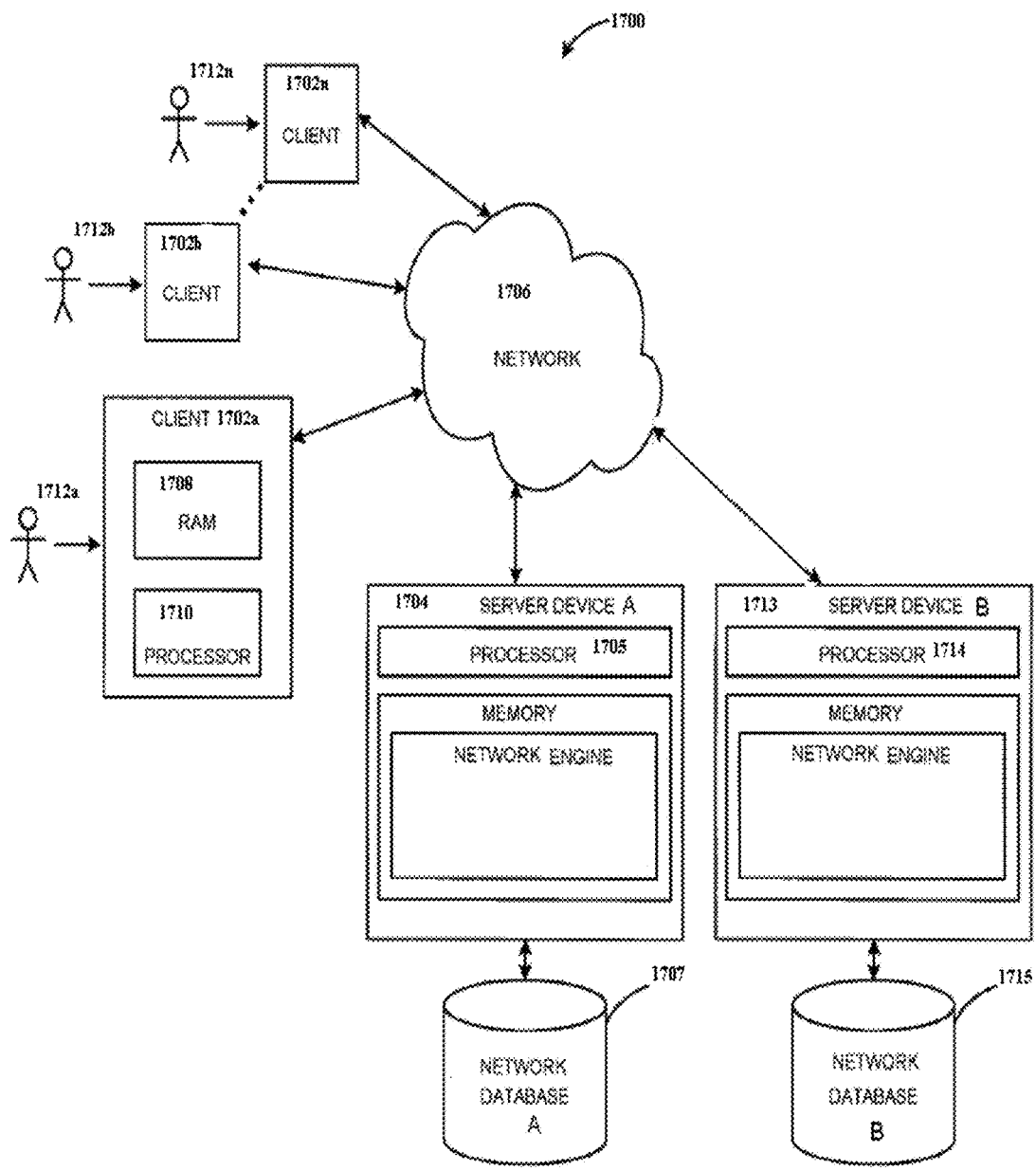
FIG. 48 illustrates features of some embodiments of the present invention.

FIG. 48 shows another exemplary embodiment of the computer and network architecture that supports the inventive method and system. The member devices 1702a, 1702b thru 1702n shown each at least includes a computer-readable medium, such as a random access memory (RAM) 1708 coupled to a processor 1710 or FLASH memory. The processor 1710 may execute computer-executable program instructions stored in memory 1708. Such processors comprise a microprocessor, an ASIC, and state machines. Such processors comprise, or may be in communication with, media, for example computer-readable media, which stores instructions that, when executed by the processor, cause the processor to perform the steps described herein. Embodiments of computer-readable media may include, but are not limited to, an electronic, optical, magnetic, or other storage or transmission device capable of providing a processor, such as the processor 1710 of client 1702a, with computer-readable instructions. Other examples of suitable media may include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. The instructions may comprise code from any computer-programming language, including, for example, C, C++, C#, Visual Basic, Java, Python, Perl, CSS, Ruby on Rails, and JavaScript.

Member devices 1702a-n may also comprise a number of external or internal devices such as a mouse, a CD-ROM, DVD, a keyboard, a display, or other input or output devices. Examples of client devices 1702a-n may be personal computers, digital assistants, personal digital assistants, cellular phones, mobile phones, smart phones, pagers, digital tablets, laptop computers, Internet appliances, and other processor-based devices. In general, a client device 1702a are be any type of processor-based platform that is connected to a network 1706 and that interacts with one or more application programs. Client devices 1702a-n may operate on any operating system capable of supporting a browser or browser-enabled application, such as Microsoft™, Windows™, Mac, Android, Apple iOS, or Linux. The client devices 1702a-n shown may include, for example, personal computers executing a browser application program such as Microsoft Corporation's Internet Explorer™, Apple Computer, Inc.'s Safari™, Google Chrome, Mozilla Firefox, and Opera. Through the client devices 1702a-n, users (e.g. players, agents, etc.) 1712a-n communicate over the network 1706 with each other and with other systems and devices coupled to the network 1706. As shown in FIG. 48, server devices 1704 and 1713 may be also coupled to the network 1706.

In some embodiments, the term "mobile device" or "mobile electronic device" may refer to any portable electronic device that may or may not be enabled with location tracking functionality. For example, a mobile electronic device can include, but is not limited to, a mobile phone, Personal Digital Assistant (PDA), Blackberry™, Pager, Smartphone, or any other reasonable mobile electronic device. For ease, at times the above variations are not listed or are only partially listed, this is in no way meant to be a limitation.

In some embodiments, the terms "proximity detection," "locating," "location data," "location information," and "location tracking" as used herein may refer to any form of location tracking technology or locating method that can be used to provide a location of a mobile electronic device, such as, but not limited to, at least one of location information manually input by a user, such as, but not limited to entering the city, town, municipality, zip code, area code, cross streets, or by any other reasonable entry to determine a geographical area; Global Positions Systems (GPS); GPS accessed using Bluetooth™; GPS accessed using any reasonable form of wireless and/or non-wireless communication; WiFi™ server location data; Bluetooth™ based location data; triangulation such as, but not limited to, network based triangulation, WiFi™ server information based triangulation, Bluetooth™ server information based triangulation; Cell Identification based triangulation, Enhanced Cell Identification based triangulation, Uplink-Time difference of arrival (U-TDOA) based triangulation, Time of arrival (TOA) based triangulation, Angle of arrival (AOA) based triangulation; techniques and systems using a geographic coordinate system such as, but not limited to, longitudinal and latitudinal based, geodesic height based, cartesian coordinates based; Radio Frequency Identification such as, but not limited to, Long range RFID, Short range RFID; using any form of RFID tag such as, but not limited to active RFID tags, passive RFID tags, battery assisted passive RFID tags; or any other reasonable way to determine location. For ease, at times the above variations are not listed or are only partially listed, this is in no way meant to be a limitation.

In some embodiments, near-field wireless communication (NFC) can represent a short-range wireless communications technology in which NFC-enabled devices are "swiped," "bumped," "tap" or otherwise moved in close proximity to communicate. In some embodiments, NFC could include a set of short-range wireless technologies, typically requiring a distance of 10 cm or less.

In some embodiments, NFC may operate at 13.56 MHz on ISO/IEC 18000-3 air interface and at rates ranging from 106 kbit/s to 424 kbit/s. In some embodiments, NFC can involve an initiator and a target; the initiator actively generates an RF field that can power a passive target. In some embodiment, this can enable NFC targets to take very simple form factors such as tags, stickers, key fobs, or cards that do not require batteries. In some embodiments, NFC peer-to-peer communication can be conducted when a plurality of NFC-enable devices within close proximity of each other.

Illustrative Examples of the System and Method of the Present Invention

Non-limiting examples of the system and method of the present invention are shown below:

In some embodiments, the system is composed of a number of CSCIs (computer software configuration items). Each CSCI may be further elaborated either in its own separate document or a section within this document. The interfaces among the CSCIs and between them and external components will also be specified.

In some embodiments, the user interface of the system—which is the primary interface to the End Users via a web browser or a web app on a smartphone or tablet, will be given its own section to describe its details. The functionality can be further inferred (beyond the description in this document) from the user interface (i.e. artifacts existing in the user interface would have to have appropriate implementation in software).

Description of a few of the technologies considered and/or chosen for the implementation of the various CSCIs.

In some embodiments, the term CSCI abbreviates "Computer Software Configuration Item", the term DB abbreviates "Database", the term "ME" abbreviates "medical expert", the term "MBS" abbreviates "medical board secretary", the term SLA abbreviates "service level agreement", the term UI abbreviates "user interface", and the term UX abbreviates "user experience".

Figure 49:
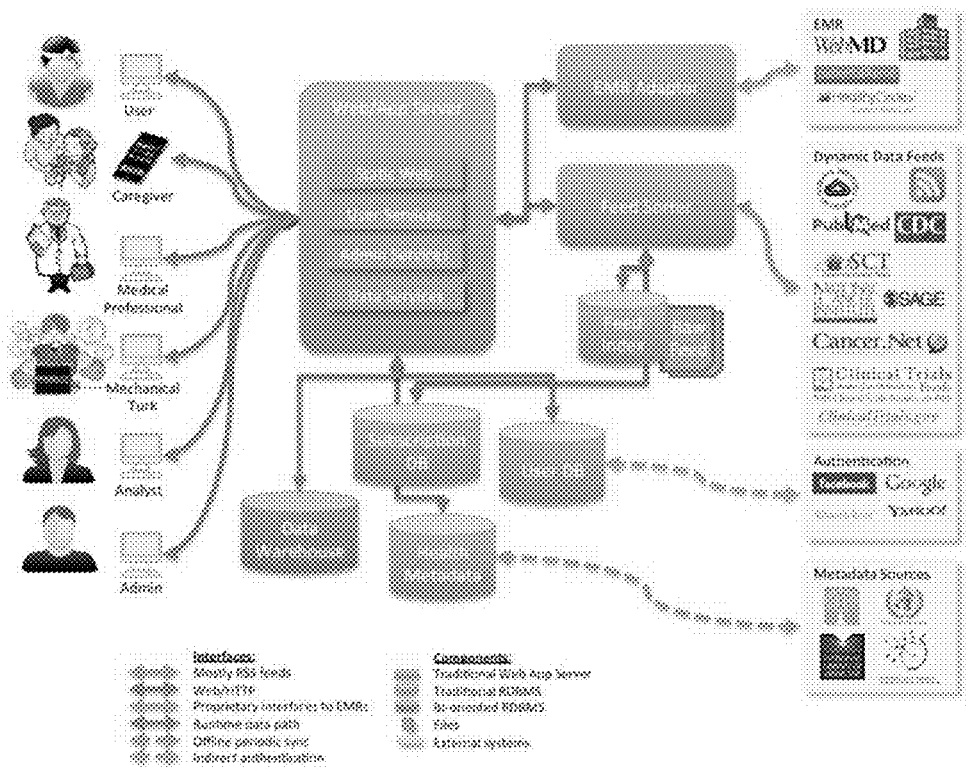
FIG. 49 illustrates features of some embodiments of the present invention.

FIG. 49 depicts the high level architecture of some embodiments of the invention. Some of these components and elements will be discussed individually in the following paragraphs.

In some embodiments, the system will have different types of users. A brief description of each type of user of some embodiments and their main uses of the system followed by some discussion about the interrelationship among them is provided below.

In some embodiments, the "End User" is a type of user—one who benefits from the service. The End User may include a person that has a medical/health condition that would primarily benefit from help regarding this medical condition. The benefit of filtering pertinent information regarding the medical condition and related information is intended for this User.

This user might herself sign up for the service and perform her own research.

In some embodiments, the use of the invention by the End User would be to provide basic and medical information about herself and then receive notifications/alerts/messages that contain highly filtered and pertinent information that could be applied by them or the medical professionals dealing with End Users to improve their quality of life, life expectancy, and/or other characteristic.

In some embodiments, End Users could collaborate with others in the system (such as their associated Caregiver(s) and/or Medical Professional(s)) regarding any of the information in their subscriptions including, but not limited to complete information items or specific highlighted/bookmarked sections of these. In some embodiments, general purpose messaging would also be supported that includes, but is not limited to individual and group messaging/discussions.

In some embodiments, the person suffering from a medical condition (End User) cannot themselves perform their health-related research because they might be too young, too old, technically illiterate or too unhealthy. In this case, someone that cares for them—a relative, friend, colleague and/or hired person may be the user performing these tasks on their behalf. Even if the End User is able to use the service herself, one or more additional people might be interested in conducting their own research and behave much like the End User in terms of their system requirements.

In some embodiments, a Medical Professional including, but not limited to, a primary or secondary care physician/medical doctor of the End User. A Medical Professional may be associated with one or more End Users. In some embodiments, the system could allow sharing of information, highlighting of information items between the End User, their Caregivers, and the Medical Professional. In some embodiments, the information flows can be individual bi-directional messages or "group messages"/discussions. The Medical Professional would use the present invention to receive up-to-date information identified by the system and/or the user that are potentially relevant to the End User's medical condition so they could offer better treatment for the End User.

In some embodiments, the End User, Caregiver, or Medical Professional could receive information about their condition, highlight the information, and share the information with any, all, and/or part of the others in this group.

In some embodiments, the system will rely on a combination of technology and professional human power to sift through the potentially relevant material regarding the End User's medical condition to find new and relevant information. In some embodiments, the human element of this would be conducted via Medical Expert (in a method similar to Amazon's approach called "mechanical turk"—the human powering the machine). In some embodiments, the people that support this function can be hired full time, part time, and/or on a per assignment basis. In some embodiments, they may have other motivations or incentives to perform the functions required. In some embodiments, the system to support them would include functions to test/verify the individual users' credentials and abilities to sift through information items and/or the ability to assign specific tasks to them and/or to receive the results of these tasks. One task would be to read information and map it to a set of conditions from which one or more End Users are suffering. Other tasks may include, but are not limited to verification of an assignment already performed by another Medical Expert.

In some embodiments, Medical Expert, to some extent, is considered an "internal user". They could, therefore, have their own discrete identities in the system and may or may not be shared with the public user base. In some embodiments, the Medical Experts are actually medical professionals with varying degrees of professional experience and expertise. Their interface may be tailor-fit so that they can efficiently perform their contribution. In some embodiments, they regard the system as a 3rd party to which they contribute/help so, aside from some exceptions, from their perspective, they do not consider themselves "internal users".

In some embodiments, insight can be gained by the data available within the system. The insight could take some careful attention to identify such data—whether for the operational support for the system, learning of new features/capabilities required and/or even to gain insight of medical nature. In some embodiments, the data analyst would require access to such information. This capability could be semi-manual. Except that A-B testing and optimization and validation of individual UX options would likely be one of the functions that benefit from much data analysis.

In some embodiments, a manager is in charge of processes (automated and manual) associated with Medical Experts (MEs) and any processes regarding the data feeds and new material being ingested into the system. The manager may or may not be paid by the operator of the system. The Manager, via a dashboard like view, may receive notifications and alerts and needs to act upon them (e.g. an SLA breach with an ME).

In some embodiments, the manager may include additional definitions of views, notifications, alarms, and actions.

In some embodiments, admins maintain the proper operation and evolution of the system. The functions range from availability and analysis of usage patterns of the deployed system/web/app to software and hardware upgrades. In some embodiments, in a cloud-based deployment, such systems may undergo some need for software and environment maintenance. Also, backup, disaster recovery, and other administrative functions would be handled. End User management as well as resolving various data or system issues may also be required. Initially, generating logs that could help identify/isolate problems and performance issues would be the basic support provided for such functions.

These would, obviously, evolve over time to more elaborate facilities—from dedicated user interfaces to guides and scripts/tools.

In some embodiments, the system shall allow connecting a End User and Caregiver. In other embodiments, the benefit to allowing to connect the identities such that redundant information is not entered and that the different people that are dealing with the End User are "on the same page". However, in some embodiments, there are situations where there it is unlikely or unnecessary that such connections are made (for instance, notifications might be personal—to individual end users—either Caregivers or End Users, or shared). Also, at times, the End User herself may not be connected to the system—so it's possible to have a Caregiver that is not connected to End User.

In some embodiments, a Caregiver could also be associated with more than one End User. Also, a Caregiver could be an End User as well. Similarly, an End User could be a Medical Professional. In fact, an individual person might have more than one "role" in the system. In some embodiments, only End User, Caregiver, and Medical Professional can have more than one role. In some embodiments, the other user types will not be intermixed with these.

In some embodiments, such connections between End Users, Caregivers, and Medical Professionals can be created and severed (removed). In some embodiments, severing these connections could be by either party. In a non-limiting example, an End User may not want others associated with their medical/health details. Also, a Caregiver or Medical Professional may no longer be associated with the End User. In some embodiments, connecting the End User and Caregiver is allowed along with allowing no such connection and/or severing a connection.

In some embodiments, the system would have to integrate with numerous external parties. In other embodiments, over time, more may be added to the list below and others are already anticipated:

In some embodiments, due to a growing use of EMRs, it would benefit the users to avoid entering redundant information—getting access to the End User's EMRs based on their authorization would allow dynamic update to this data as well as more timely and effortless data exchange. In some embodiments, there are also EMR aggregators that may serve as potential partners/integration points.

In some embodiments, the prime source of information would be RSS feeds from a variety of site that produce original content or aggregate it from other sources. Non-RSS feeds including, but not limited to, email, application programming interfaces (APIs), Web Services, SOAP, REST, ebXML, and any other possible way to connect to other computer systems. In some embodiments, the incoming feeds of information to the system would be facilitated, in part, by off-the-shelf components to integrate within the software and/or Yahoo Pipes and equivalents. In some embodiments, the number of data feed sources may be in the hundreds or even more.

In some embodiments, hundreds of information items are expected each day. An information item might exist more than once in any particular feed or across feeds—in fact, it might not look "the same" but it would be about the same raw information item.

In some embodiments, social log-in widget would be used to allow authenticating by using any credible social Open ID or other common/popular authentication service. The system could still ask for an email address to allow recovery of credentials of a user in case something happens to their other identity. The interfaces can be governed by the standard for external authentication of the social authentication service. A 3rd party library could be used to facilitate these actions.

In some embodiments, medical conditions, symptoms, drugs, treatments, and many other types of data are very complex. In fact, there are many standards in various levels of maturity, breadth, depth, completeness, and acceptability available. The medical metadata is relatively static—in that it doesn't often change every day. However, it does change over time. New information is added and changes are made. In some embodiments, the method of populating the data and keeping it up to date would include a periodic ad-hoc process. In some embodiments, this will be conducted based on Unified Medical Language System ("UMLS") and associated tools, as they contain both semantic foundations and a metathesaurus that calls out the rest of the sources explicitly and is not strict. In some embodiments, the system will add its own metadata to define key distinctions of the primary medical conditions for which the system is designed to handle. In some embodiments, this will be selected by an expert or equivalent and then codified in metadata. In some embodiments, this information is not coming from the metadata sources directly.

In some embodiments, the functions of the system components are described below:

In some embodiments, the application logic and user experience are handled by the Web/App Server. In some embodiments, it is composed of the following services:

Static Web—much of what the user sees is visual elements that are static—in that they change infrequently (but they do change). The data is updated using a content management system ("CMS") front end or files directly on a file system.

End User Services—the user experience could be built into a set of services that are performed as invoked by user action on the web site. There would be many user services to perform each of the actions expected by the end user experience.

Admin Services—some services could be defined for administration functions and reporting.

Data Services—data services could be to invoke action not initiated by user—perhaps scheduled, or triggered by data. Also, services may be for maintenance of the various databases and other data structures.

In some embodiments, specific adaptors for maintenance and exchanging of the EMRs are developed for each category of such integration points that are desired.

In some embodiments, the primary dynamic data entering the system would be handled by the Feed Sorter. In some embodiments, the Feed Sorter would have a list of configured feeds (the feeds themselves could be configured by an Admin). These feeds could either be direct feed Feed Sorter or they could be intermediated (e.g. by Yahoo Pipes or a similar cloud-based solution) or a combination of both. In some embodiments, the primary interface is RSS. In other embodiments, the primary feed sorter may not be RSS. In some embodiments, hundreds, or even thousands of sources could be feeding the system and overall there would be hundreds of new items per day. In some embodiments, these could include duplicates both on individual feeds as well as across feeds. Furthermore, not all the raw publication/data may be accessible—so, for instance, news of a new research publication might come in, but the research publication itself may not be accessible.

In some embodiments, if access to the full information items from the publications is present, the Feed Sorter could determine how to automatically access the full information item and bring it over.

In some embodiments, the data would be indexed and sorted and the index would be maintained in the Feed Index. In some embodiments, the raw data feeds and information items would be stored also in the Raw Feed. In some embodiments, the final function of the Feed Sorter would be to sort the data to Medical Experts to review the material. This would be based on data available from the medical conditions tracked by the system (on behalf of its users).

In some embodiments, an End User Email Interaction Manager is an interaction manager that uses form-based emails to interact with End Users. Templates are designed and conditions by which emails are sent.

In some embodiments, a Review Process Manager is a process manager that manages the entire review process of new information performed, primarily, by Medical Experts (MEs). It handles sending automated emails based on state transitions—both automated and manually initiated by a Manager. It also has a front end exposed to a Manager (MBS) to manage the process. There are two methods of interactions with ME—email and web.

In some embodiments, skill Set Matcher component produces a list of several Medical Expert (ME) candidates to review the information item (configurable amount of ME candidates). It may rely on the Medical Expert DB that will contain a list of skills or domains of expertise of the Medical Experts.

In some embodiments, one or more databases would be employed by the system. In some embodiments, the data quantity and user base are expected to be manageable by traditional database architectures and amenable to SQL-manipulation. In some embodiments, a triple store and semantics will be used for the system. In some embodiments, a cluster of MySQL would be used as the primary technology for database storage. In some embodiments, a small Semantic DB might also be used to complement it.

In some embodiments, the databases identified below may be a single instance or spread across multiple instances.

In some embodiments, the End User DB contains the information about the users of the system, their basic information, medical conditions, subscription settings, relationships between them, and more. In some embodiments, for security reasons, this DB will be separate on two different machines. One will contain the personally identifiable information (PII) and user credentials and the other will contain information about their medical conditions and other medical data or relationship data. In some embodiments, there will be a primary key (likely a GUID) that would be used to connect between the two. The personally identifiable information (PII) will be stored in an encrypted fashion, with methods to encrypt/decrypt and possibly change the encryption periodically. In some embodiments, this separation should make the system less prone to breach vulnerability.

In some embodiments, the Subscription DBs database contains the "messages" within the system. The subscriptions are actually messages sent to the user—in a variety of means. In some embodiments, the status of such messaging is in this database. To some degree, this is like a mail system, but it has some specific functionality and annotation of data. It also records more specific statuses of messages as well as annotations of the raw messages, in particular information items. In some embodiments, it looks very much like a custom mail-like front end.

In some embodiments, the Medical Expert DB contains the Medical Experts (MEs) in the system. In some embodiments, for privacy/security reasons it should be separated into personally identifying information that may be sensitive and information not personally identifiable. The DB may contain the profile information of the ME as well as their skills/expertise. It will also contain information about their work queue as well as any reward program data.

In some embodiments, transaction data and aggregate data would be stored in a data warehouse—transactions and user flows as well as information about data flows and subscriptions.

In some embodiments, the Health Metadata database contains the raw and digested semi-static information about the medical field of knowledge. It is populated manually periodically using tools and custom scripts.

In some embodiments, the technology choices may include a tech blog such as Ruby on Rails server side running on a LAMP stack, and host in the cloud such as Amazon. In some embodiments, CSS/Javascript in the client. In some embodiments, HTML5 will be used.

In some embodiments, the system uses a "Big Data" architecture (with, for example, Hadoop/Cassandra). In some embodiments, as the ME review process is not very different than a Wiki (e.g. Wikipedia) that is updated by many experts concurrently, a Wiki foundation may be used for various aspects of the system. In some embodiments, discussion boards are commonplace within Wiki—and in particular, such discussions associated with particular information items. Also dispute resolution mechanisms could be adopted from such wikis.

In some embodiments, the Web Site and Application User Interface section will be based on wireframes for key UI screens/pages visible via the web site. In some embodiments, renderings for mobile devices will be added, and/or include native apps.

In some embodiments, the present invention will include an End User Interface with a Web Front End. In some embodiments, the Web Front End main user interface is facing the external users, that is End User, Caregiver, or Medical Professional. In some embodiments, the UI has clean and modern consumer oriented graphics and animated/active visual interactions.

Figure 50:
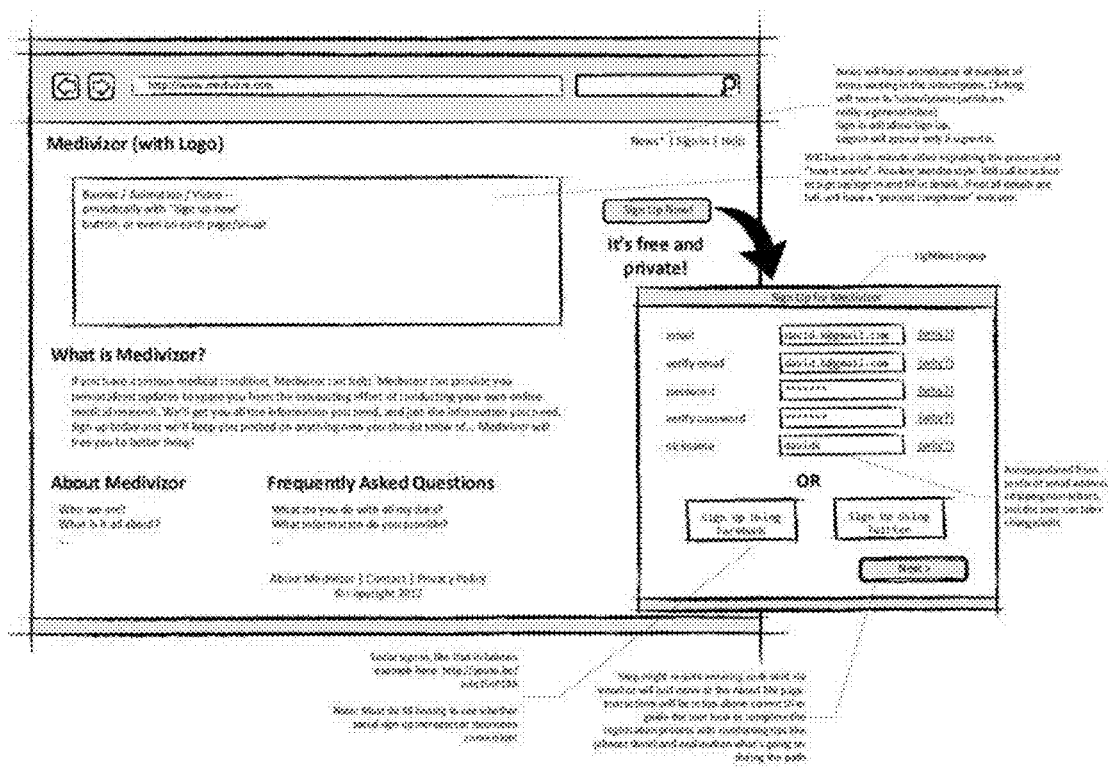
FIG. 50 illustrates features of some embodiments of the present invention.

In some embodiments, the present invention includes a Web Home Page and Sign-up/Sign-in. FIG. 50 shows an non-limiting example of the web home page and sign up/sign-in of one embodiment of the present invention. (non-signed-in user clicking "Sign Up Now!" or any "sign up" link). In some embodiments, there would be a totally different view (though same "look and feel"/skin) when a user is signed in and not signed in. In some embodiments, when the user is not signed in, it is assumed that the user could be either a non-user (someone not yet registered on the site) or a user. If a user, it is designed to guide them to sign in and use the app. If a non-user, it is designed to help them learn about the system, whether it is suitable for them, and if suitable for them, to help convince them to sign up for the service.

In some embodiments, the system may include various public information that would entice the user to read more, and for more information, it would encourage them to sign-up. In some embodiments, the system includes a basic launch page for anyone that isn't signed in. Cookies could keep people that are already registered signed in—much like many other services with the "Keep me signed in" check box turned on by default at log in screens.

In some embodiments, the main feature of the initial page is a ~1 minute video that is a sketch art with voice and text explaining the solution and steps to using it. It ends with a clear call to action "Sign Up Now!". In some embodiments, a FAQ link+data is also available on this page. In other embodiments, information about the provider and service is easily accessible from this page—though the video and call to action should be prominently displayed.

Figure 51:
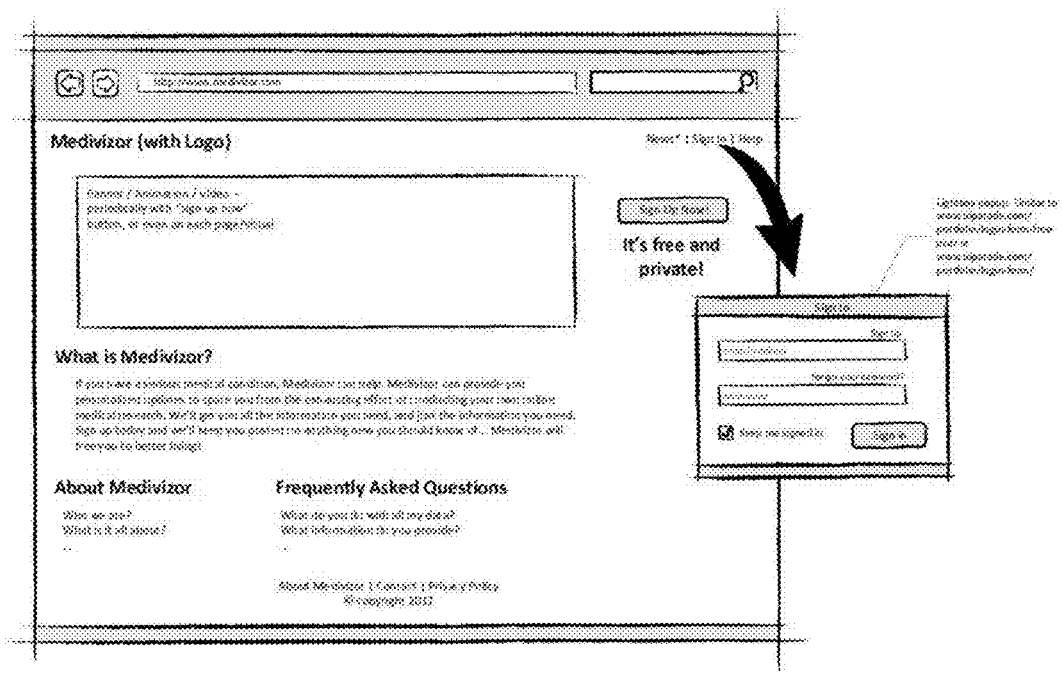
FIG. 51 illustrates features of some embodiments of the present invention.

FIG. 51 shows more features of some embodiments of the present invention. In some embodiments, sign up would allow either native sign up to the service without any credentials from other sources or a social sign up—as available on many other sites these days. In some embodiments, additional details such as an email address (to retain the service in case of failure in the other services) as well as a nickname will be requested by the system. In some embodiments, the system would then guide the user to enter the rest of the pertinent information.

In some embodiments, users are End Users rather than Caregivers or Medical Professionals. In other embodiments, these roles will be added and different stages to address those different user types.

Figure 52:
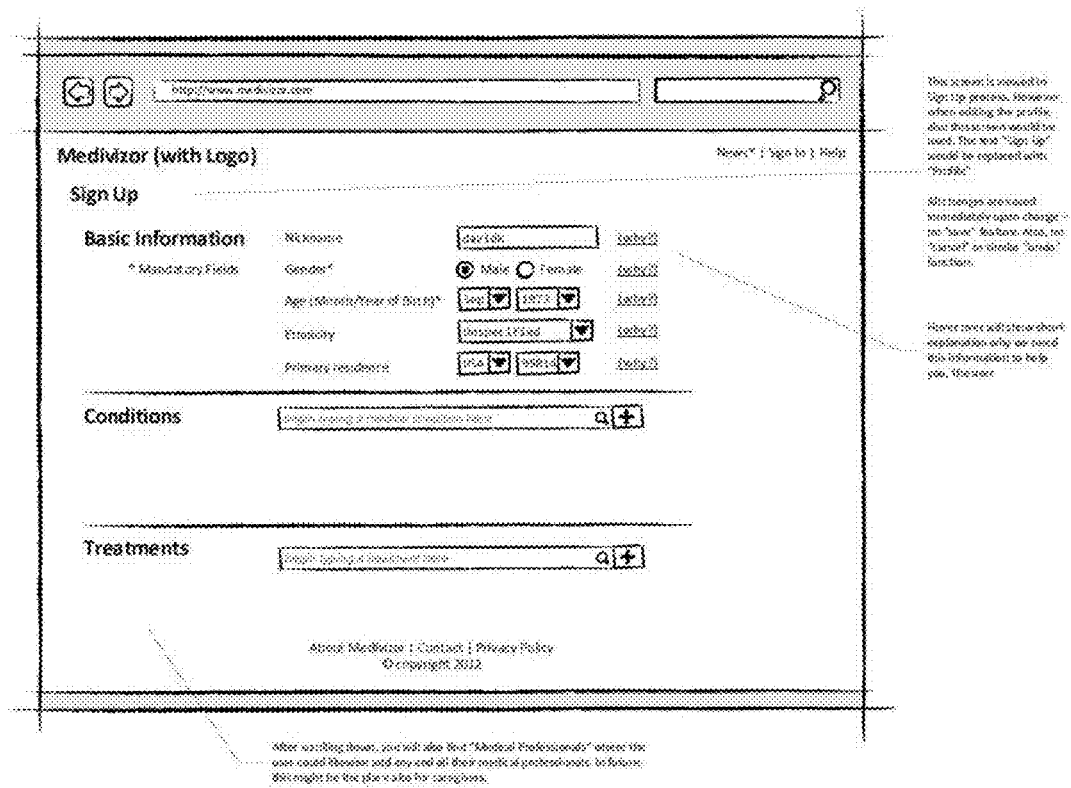
FIG. 52 illustrates features of some embodiments of the present invention.

FIG. 52 shows an non-limiting example of the web sign-up interview of one embodiment of the present invention. The general structure of the screen and navigation of one embodiment is shown on FIG. 52. In some embodiments, clear tooltips and explanations upon mouse over to explain the fields and the rationale for asking for particular information.

In some embodiments, in this Sign Up page, explanatory text would clarify that the information entered should be about the person that suffers from a serious medical condition even if the Caregiver does it on another's behalf. In one embodiments, one data entry of the sign-up/registration process will allow the End User to specify as part of the sign-up process whether they are filling this for themselves or on behalf of someone else. In some embodiments, this will be include in the "Basic Information". In some embodiments, the present invention inquires as to the nature of the relationship between the person entering the information and the person suffering from the medical condition.

In some embodiments, Notifications, information items or, later, signed in user name could exist in a variety of sections. In some embodiments, the number of notices or their severity could be visually indicated. In some embodiments, basic information and medical information would be collected using this one form. In some embodiments, conditions, treatments, and medical professionals would be collected. A prompt would immediately suggest adding the next one after each is entered.

In some embodiments, an overlay "guide" would guide the user to complete the process, tracking the percentage complete so the user would know what's missing and what he needs to do to complete it. In some embodiments, clicking on the guide could take the user to where the continuation would be required. In some embodiments, this would be the basic information required. The next step would be to provide information about the medical condition which the End User has. The examples below describe "Medical Condition". The same interface would, essentially, be used with Treatments and Caregivers. Here the word "Caregiver" is not necessarily intended to be the users identified as Caregiver but rather the medical professional.

Figure 53:
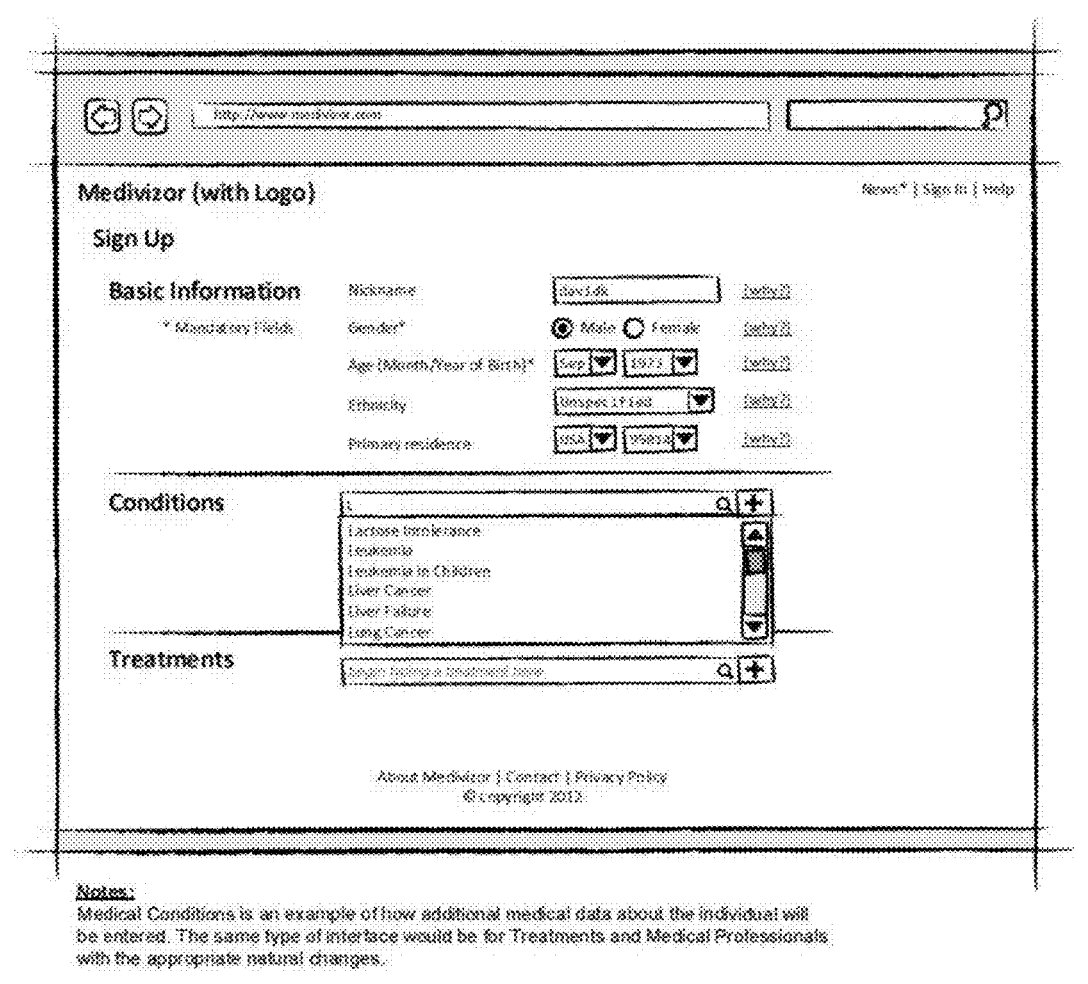

FIG. 53 shows more features of some embodiments of the present invention. In some embodiments, the prime interface is anticipated to be search-based rather than the typical "symptom checker". The expectation is that the user has already undergone diagnosis and is either diagnosed with or suspected to be with a particular medical condition. Notice that the searcher within field should not just look for prefix, but any string occurrence and even in synonyms of the same condition.

Figure 54:
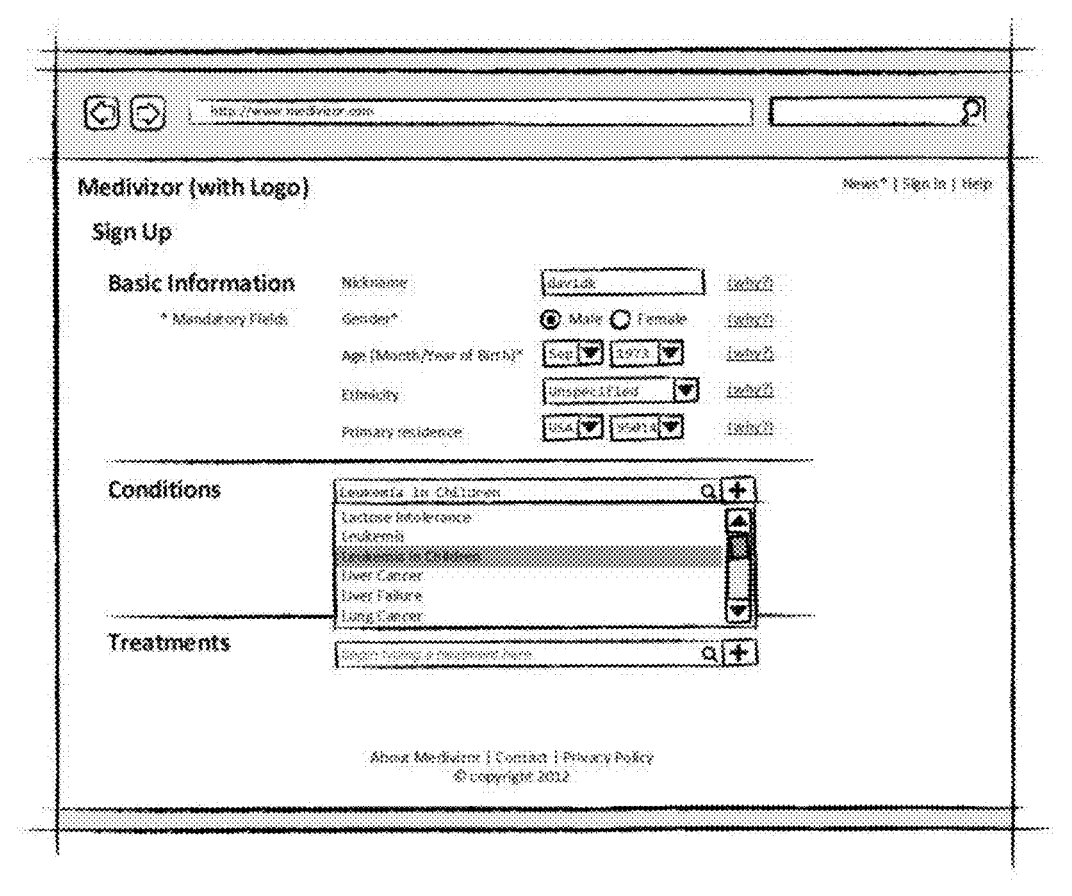
Figure 55:
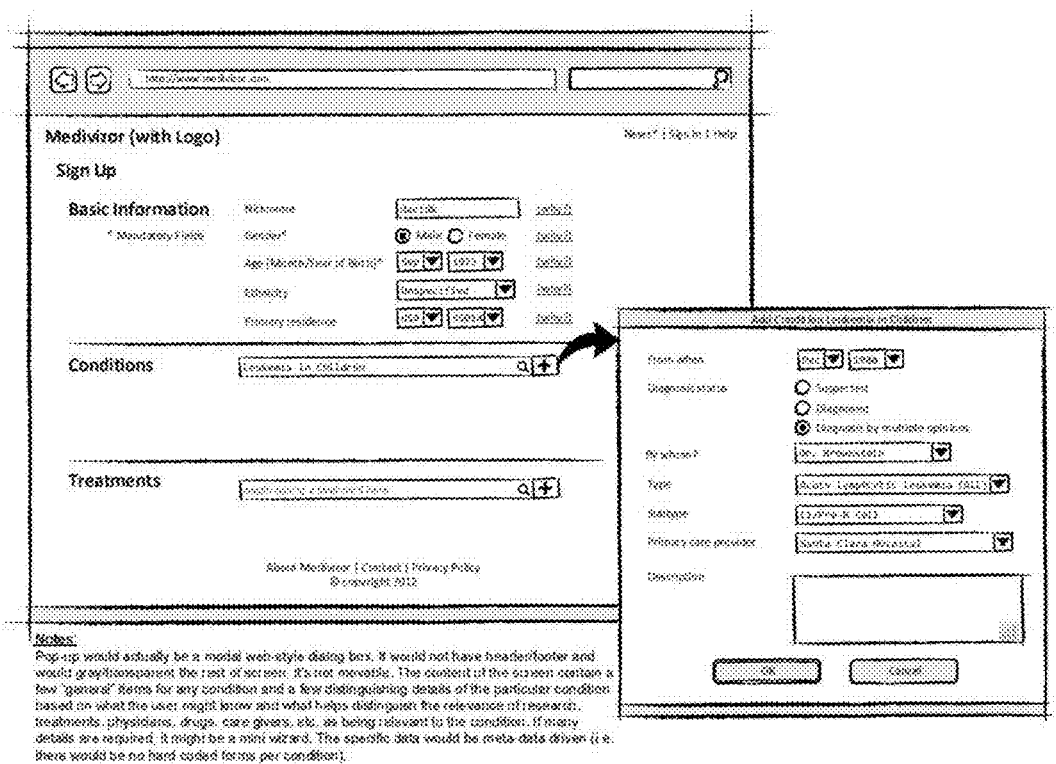
FIG. 55 illustrates features of some embodiments of the present invention.

FIGS. 54 and 55 show more features of some embodiments of the present invention. In some embodiments, once the condition is entered, the user would be prompted to enter additional conditions, however, the previous condition would be added to the list of conditions and there would be a textual summary of the condition.

Figure 56:
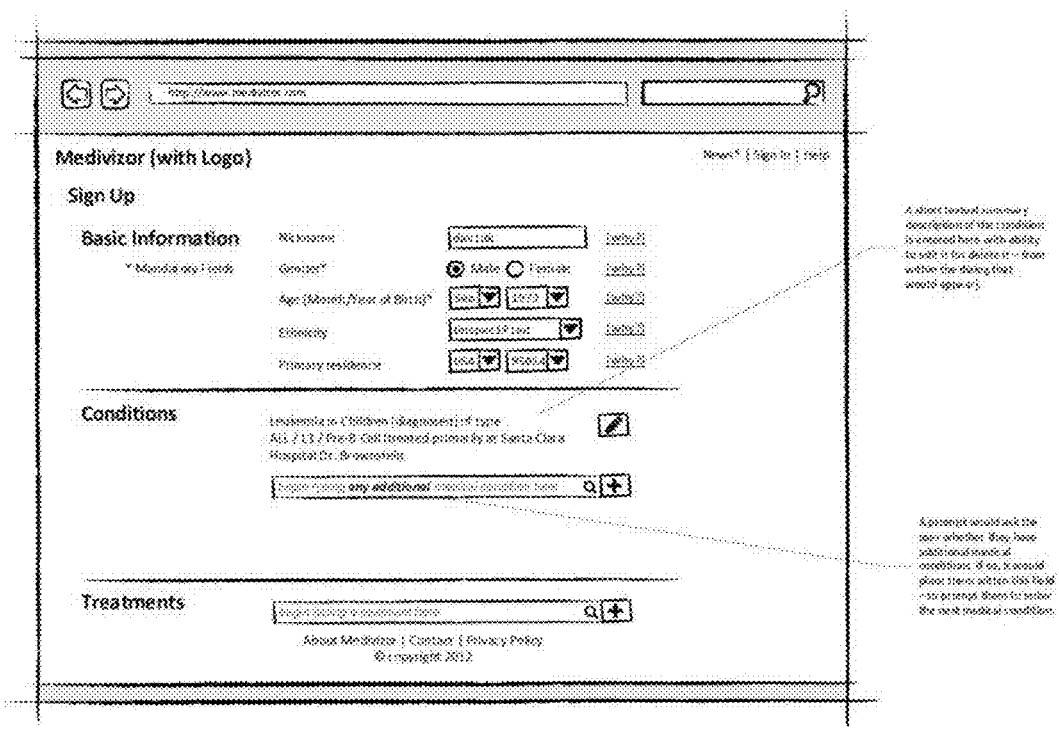
FIG. 56 illustrates features of some embodiments of the present invention.

FIG. 56 shows more features of some embodiments of the present invention. In some embodiments, the entry of this sort of data is for "first time setup" of the system. In some embodiments, much of the use of the system would be to read data feeds created by the system. Nevertheless, the user would be able to edit their Profile later and the same interface would be used.

In some embodiments, upon sign-up, the system will send the user basic information about the conditions he/she has as a message. In some embodiments, it will also send him recent data relevant to their particular condition. In some embodiments, the data will be from the past month or so. The basic data about the condition is primarily for those users that are newly diagnosed people would like to be able to learn more about their condition.

Figure 57:
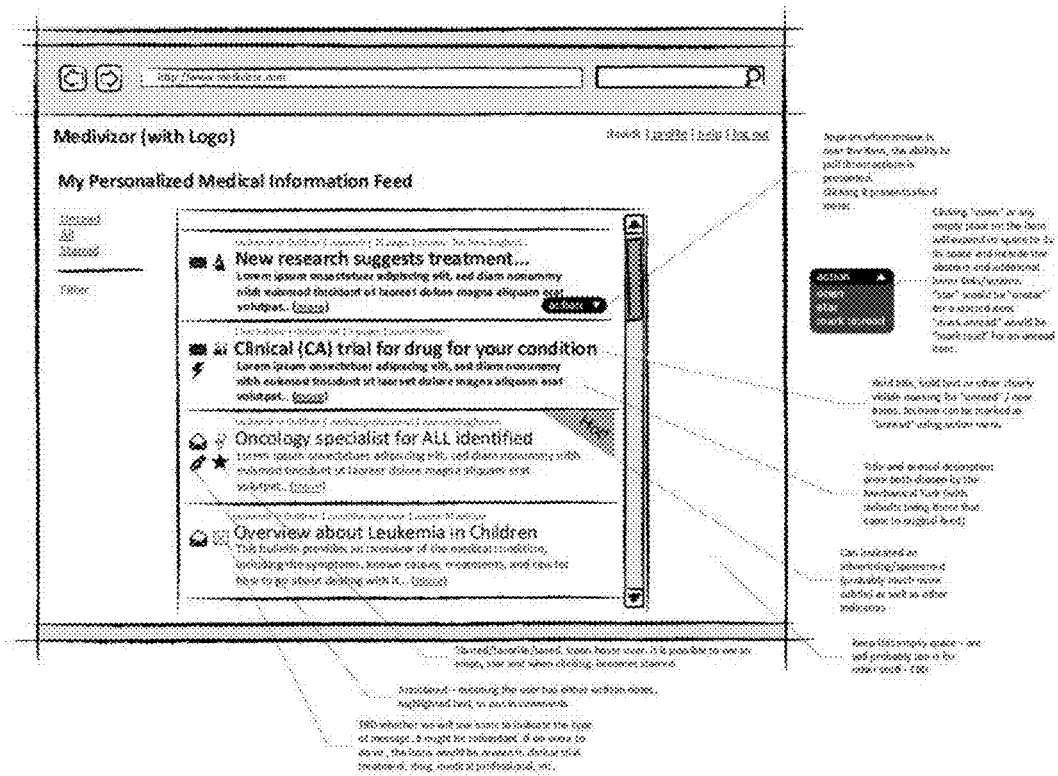
FIG. 57 illustrates features of some embodiments of the present invention.

In some embodiments, the system includes a Web Subscription/Feed as shown on FIG. 57. In some embodiments, this is the main page that contains the key value of the solution—providing a highlighted and filtered feed of "highly relevant" information for the End User. In some embodiments, this list is filtered and prioritized based on a combination of automation, Medical Experts, and crowd sourcing. The data is presented in a visually compelling way that allows easy navigation and further reading and annotating. This is the main screen the user sees upon being signed into the web app.

Figure 58:
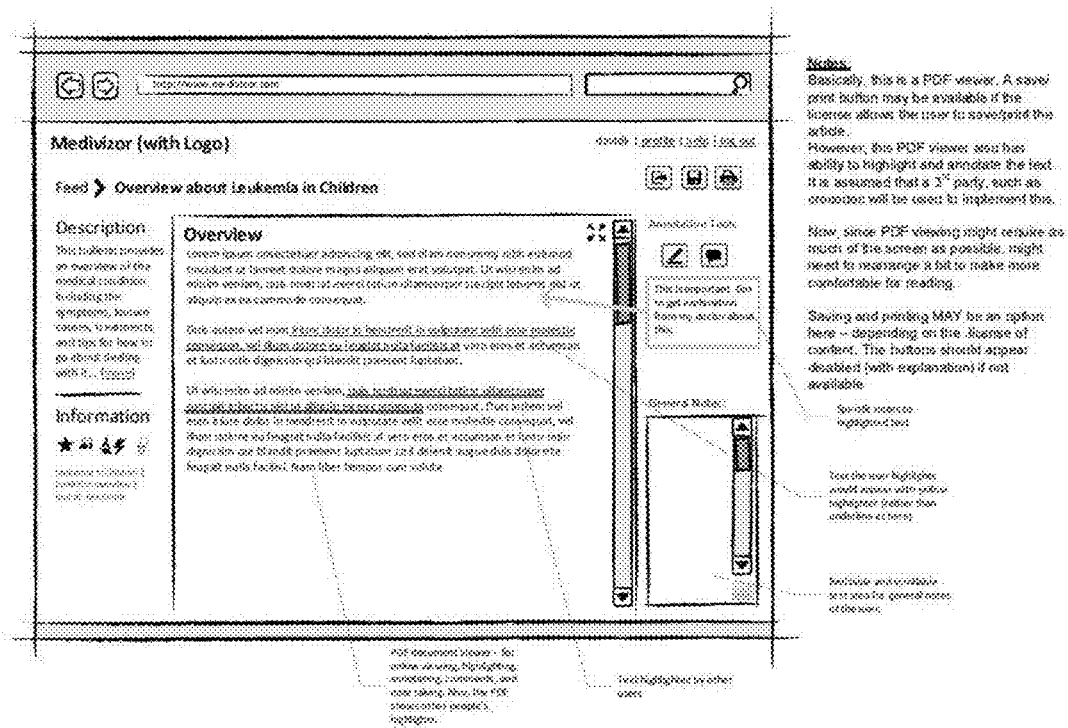
FIG. 58 illustrates features of some embodiments of the present invention.

In some embodiments, the system includes a Web New Information Detailed View. In some embodiments, clicking any item, enlarges it enough so that the all or part of the abstract can be viewed. In some embodiments, the user can then click to open the item in full detailed view as shown in FIG. 58. In some embodiments, the detailed view shall consists of, but is not limited to the following: Ability to see much of the screen real estate dedicated to the information item itself; ability to perform the basic actions that were available in the drop down also from that page with dedicated buttons; ability to navigate back to the list view; ability to move to the next information item; ability to annotate a section; and/or the information item should open within the browser in the appropriate environment and thus the system would convert a variety of formats to fit the same screen for readability/usability.

Figure 59:
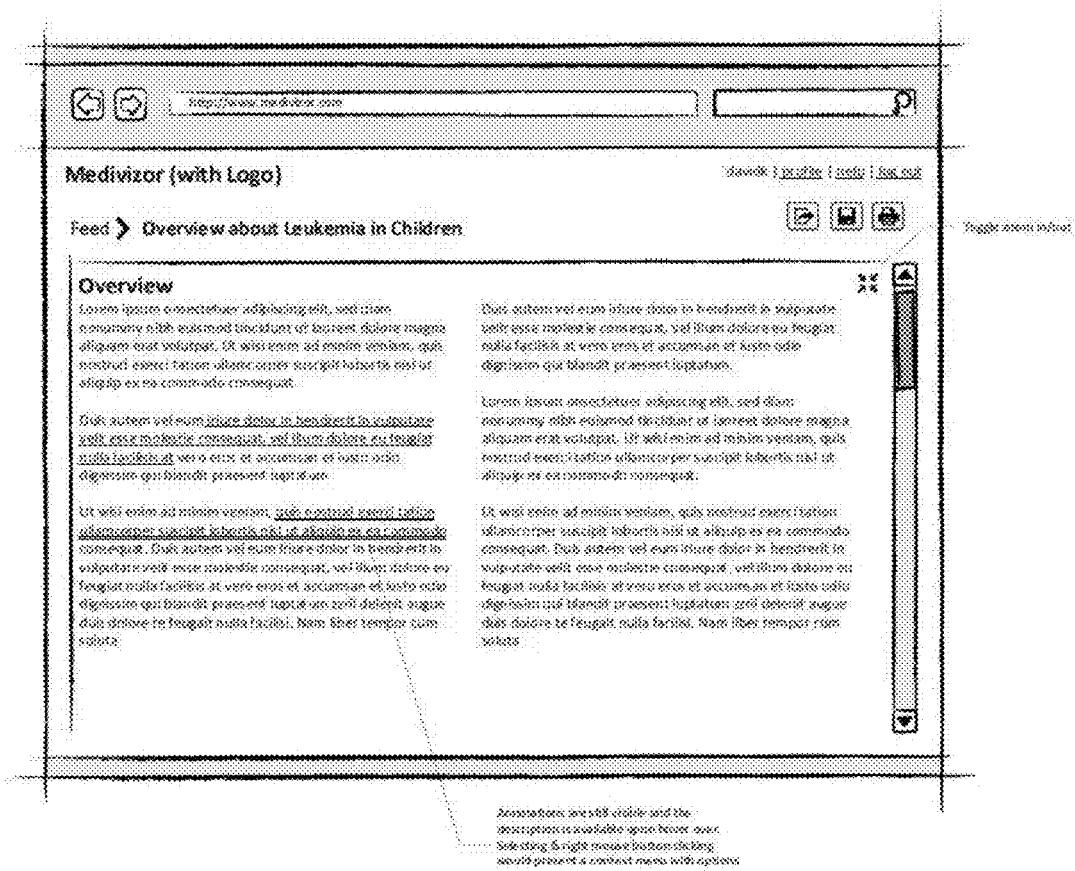
FIG. 59 illustrates features of some embodiments of the present invention.

In some embodiments, reading the PDF file may require more screen real estate and thus it is possible to zoom in and zoom out of the view. This view is shown on FIG. 59. In some embodiments, while information items can be viewed at least on screen, there would be some that would be unable to present to the user so that they would need to buy them or provide information about them to their medical team that would acquire them separately. In some embodiments, the status for the information items may include, but are not limited to: Full rights to present to the user and allow him to print/share/save; Partial rights to present to the user, but not print/save; Reseller rights to sell to the user the information item; No rights—no secured any right to present or resell the information item.

Figure 60:
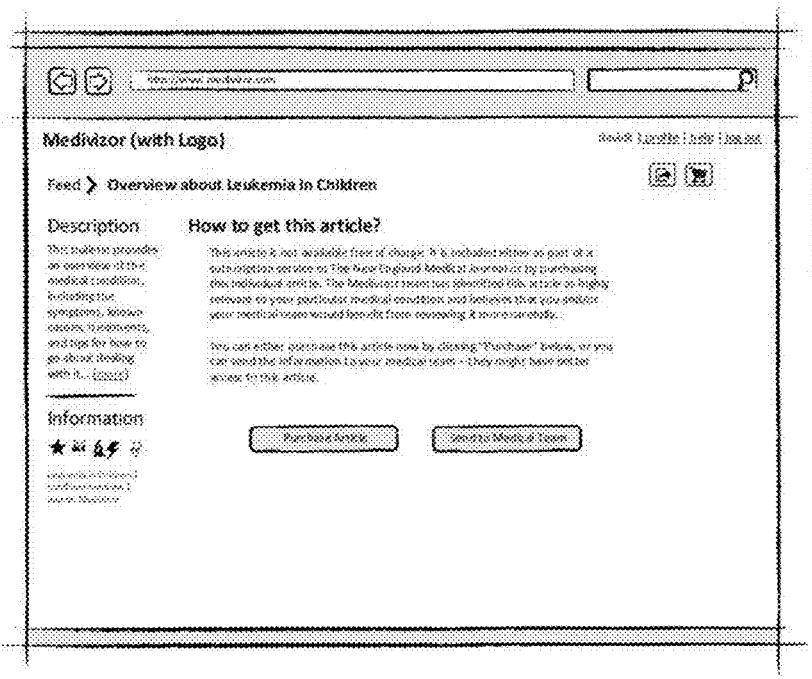
FIG. 60 illustrates features of some embodiments of the present invention.

In some embodiments, in the Web Buy Information item View shown on FIG. 60, reseller rights or no rights are the statuses of the information items.

Figure 61:
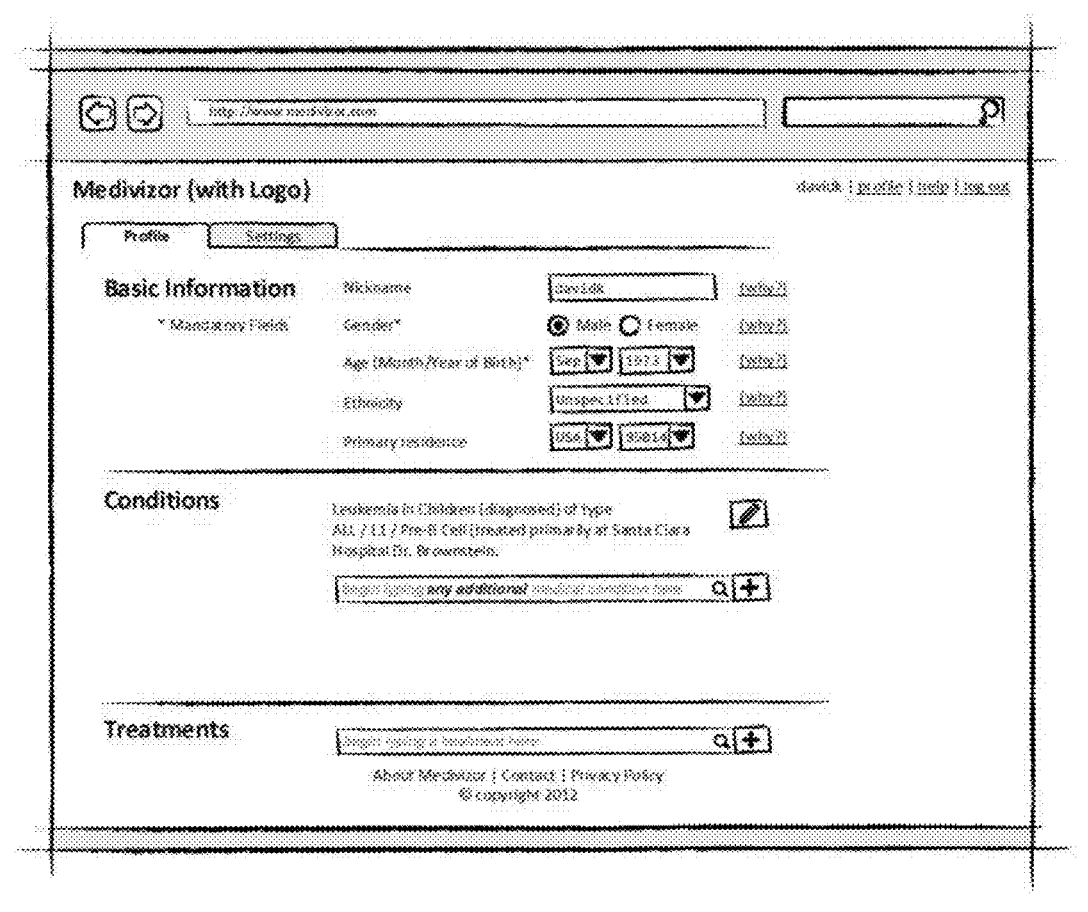

In some embodiments, in the Web Profile Settings View shown on FIG. 61, the user would be able to return to their profile and modify profile information.

Figure 62:
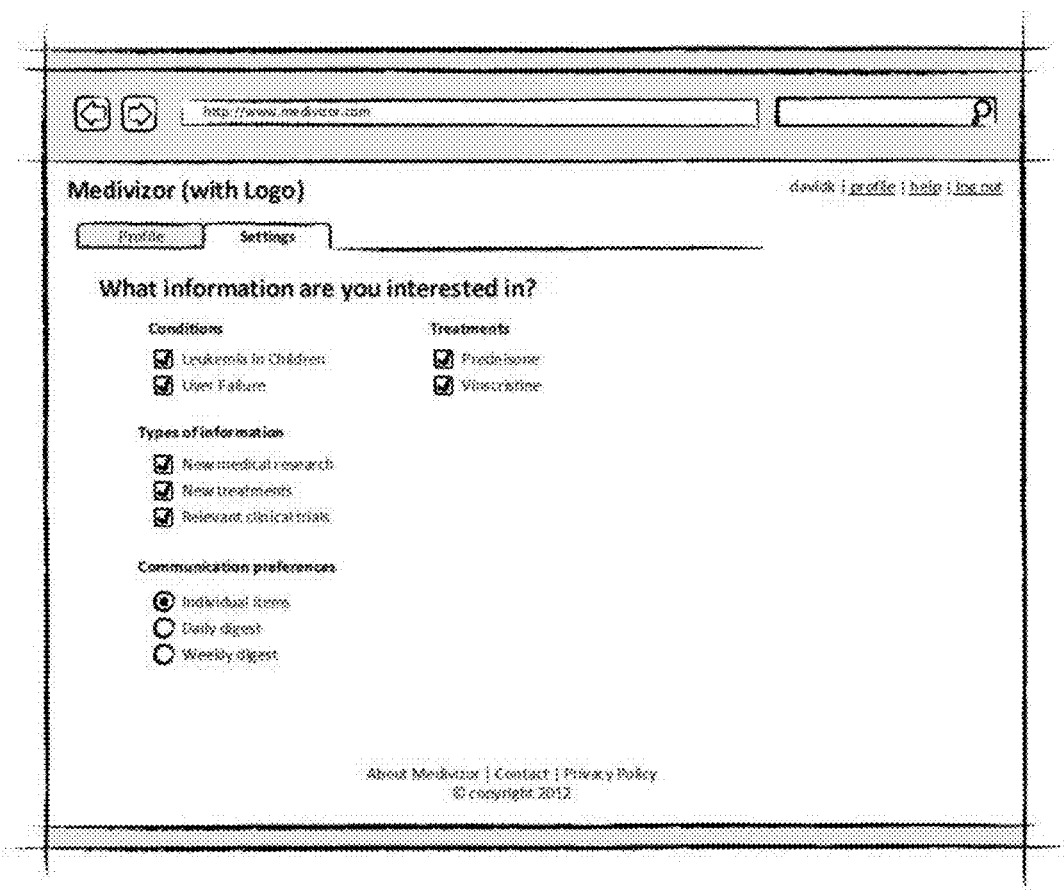
FIG. 62 illustrates features of some embodiments of the present invention.

In some embodiments, the user would also be able to modify his profile and to adjust settings as shown on FIG. 62. This page may include, but is not limited to: the user would be able to select which types of information they are subscribed to out of a list of types of feeds, including, but not limited to, new research, clinical trials, new treatments, new drugs, new medical professionals, etc. They would be able to do this for each different condition they have entered as well as for the treatments they are receiving (for instance, new information about the drug they are taking); the user would be able to set which emails they receive (in addition to the online subscriptions). They would be able to request daily/weekly digest or individual messages. They would be able to opt out of the system announcements and information or 3rd party information. All or some would be turned on by default; and/or important information from the system that may include, but is not limited to personal messages, etc. that are in their subscription inbox.

In some embodiments, the present invention includes an End User Email Front End. In some embodiments, aside from the web front end, which will be the main interactive interface, the user will be interacted with via emails. In some embodiments, emails would be the prime trigger to the End User that new information exists awaiting them on the system web site and would prompt them to click links in the email in order to learn about the new information. In some embodiments, the emails provide just enough information to make users take action by going to the web site as interactions with emails are not easy to trace.

In some embodiments, the list of emails sent by the system may include, but is not limited to:

In some embodiments, confirm sign-up—upon sign-up, the system will send a welcome email that will ask the user to verify that they have access to this email address. This email address will also be used for password recovery.

In some embodiments, welcome and intro—after confirmation, the system will send an email introducing users to the system process—reaffirming things they may have already seen on the web site. Including describing the next steps. It will also point to where they can update their profile and how they can modify their email and subscription preferences.

In some embodiments, complete missing details—if the system confirms that insufficient details were entered in order to provide specific enough data subscription feed, the system will point out exactly what fields need to be filled in, how one could ask the medical team that handles their case to provide the missing details (a set of questions to be asked), and a link to directly access the web site in order to complete the missing details. Additional details might include specific sub-condition questions that were not answered (were answered with "I don't know"), missing treatments, missing co-morbidities, missing key demographic data, etc.

In some embodiments, thanks for completing missing details—When the user completes missing details, they will get a thank you email. It will now tell them whether their profile is complete enough or there are additional missing details that need to be completed, again, pointing them to complete them.

In some embodiments, the information item—the email from the system with actual data pertaining to the medical condition, treatments, etc. The email itself will just be a "enough info" to entice the user to click the link and access the information online in the subscriptions/feed page of the web site. So, information would be accessed online rather than in an email to the client. This email would be a "current state of the art" email that summarizes the information known about the medical condition—as specific enough as possible/feasible with the information available about the user. In some embodiments, it might point to 3rd party resources as well—so the system will refer the End User to the more pertinent information. For example, the system may point out a great web site where there's a user forum. The system may point to the NCCN patient guide. The system could create a sort of check-list and present it to the user of things they would benefit from reading/doing at this stage. It would also summarize the current approach to treatment.

In some embodiments, for each information item the user receives, the user may provide feedback such as marking the information item as "not helpful" or irrelevant using any method described above. In some embodiments, the user feedback can be used by the system of the present invention to automatically improve the logic and/or to prompt rechecking of the classification of an information item.

In some embodiments, the system of the present invention can automatically update and/or review classification of an information item based at least in part on historical user feedback. In some embodiments, the system of the present invention may identify a subset of the users with a particular common denominator in terms of their user profile that are more likely than others to mark an item as relevant or irrelevant. In some embodiments, the system may identify a subset of the users with a particular common denominator in terms of their user profile that are more likely than others to mark an item as relevant or irrelevant and thus identify users that may consider the information item relevant or irrelevant. In some embodiments, this can also highlight the area in which the classification may be incorrect.

In some embodiments, new information—Based on the preferences of the user (individual emails or digests), the End User would be sent an email indicating there is new information that meets their specific medical condition/profile. The name and type of the material as well as the possible relevance to the End User would be highlighted with a link to the material on the web site. This may be a common email the user would receive. Each email may include one or more information items.

In some embodiments, specific texts and visual layouts would need to be designed for the emails.

In some embodiments, the system includes a Medical Expert User Interface. In some embodiments, the Medical Experts are an integral part of the solution, yet they are assumed to be busy professionals in the medical field. In some embodiments, the main interface used by Medical Expert and their main use cases are defined below.

In some embodiments, the system includes Medical Expert (ME) Use Cases to reduce the overheads required from MEs to the bare minimum. Therefore, the system, in some embodiments, shall rely primarily on automated email communication protocol between they system and the MEs accompanied with a minimal need from the MEs to go online and work via the system online tools. This allows for some of the work of MEs to be done offline (perhaps when disconnected/on a plane) and only minimal work online to complete their activities. In some embodiments, the automated email communication protocol assumes that emails are at times read on smart phones. In some embodiments, this serves as a guideline to the email UX design as after getting acquainted with the system, MEs would need the ability to quickly respond to the automated emails, hence the relevant information and links/buttons would appear at the beginning of the email. In some embodiments, after piloting with the initial automated email text, emails sent to veteran and active MEs might be much shorter and focused.

In some embodiments, the system would utilize a 'follow up & reminder' component to communicate with MEs. In some embodiments, whenever an ME commits to an activity, the system would automatically generate a reminder prior to the agreed due date (configurable duration per case). The system could also monitor replies—assuming a 'call for action' is sent to a group of MEs and no reply is provided within a certain time period (configurable duration per case), the system would activate a handling protocol (per case— e.g. a 'call for action' to an additional set of MEs). In some embodiments, the roles used in this section include, but are not limited to, ME Reviewer—the Medical Expert chartered with reviewing an information item, classifying it and summarizing it.

ME Auditor—the Medical Expert charted with conducting a peer review (based on the ME Reviewer's work).

ME Editor—the Senior Medical Expert charted with dispute resolution in case required (between the ME Reviewer and the ME Auditor).

Medical Board Secretary (MBS)—the Medical Board Secretary serves in a managerial role, supervising the ME related process (automated and manual). The Medical Board Secretary has equivalent role of the Manager mentioned earlier.

In some embodiments, the following section describes the flow of enhancing the system repository with new information items (once the Feed Sorter has identified candidate information items). This may include, but is not limited to, the following sub flows:
1. The process of reviewing the new information item
2. The process of auditing the new information item (peer review) and/or
3. The process of dispute resolution (between the ME reviewer and the ME auditor)

In some embodiments, one of the possible methods to incentivize MEs would be a reward program that can be used to access valuable benefits for the ME. In some embodiments, reviewing, auditing or editing an information item entitles the ME to gain credit/points and redeem them later on. In some embodiments, the Reward Program is similar in nature to a Frequent Flyer Club.

In some embodiments, the system includes a Feed Sorter Input to this process that originates from the Feed Sorter component which produces a candidate information item (i.e. an information item that has not yet been reviewed [or is in the process of being reviewed] and included in the system repository). In some embodiments, the objective of the system is to have the original author of the information item to conduct the work of the ME Reviewer. In an embodiment where the author is not part of the system/ME community, the following procedures may be implemented:
1. The Medical Board Secretary (MBS) receives a notification in the form of an email or other acceptable means of communication.
2. The MBS then decides whether to approach one or more of the authors (or the institute the author might be part of).
3. Assuming so, the MBS then attempts to 'enlist' the author and add him to the system ME community (this is according to the manual procedure of enlisting MEs).
4. Assuming successful, the process continues as described hereunder excluding the need to find an ME Reviewer as the author becomes one (i.e. assumes responsibility according to the guidelines described below).

Figure 63:
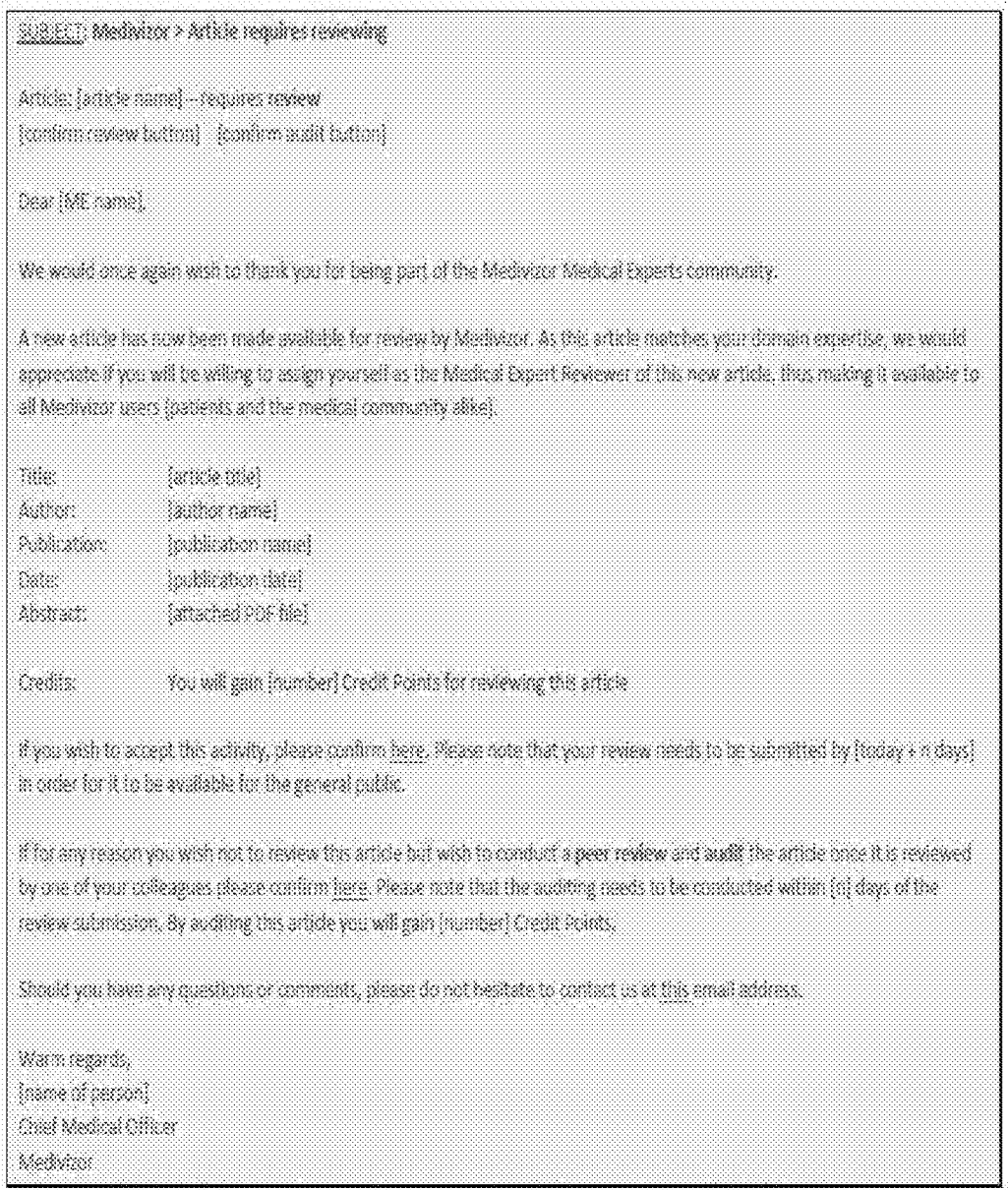
FIG. 63 illustrates features of some embodiments of the present invention.

In some embodiments, the system includes Reviewing New Information. In some embodiments, an information can which can include, but is not limited to, new information that may or may not be an information item. In some embodiments, the candidate information item (or any new information) is associated with a list of (potential) Conditions. As each ME is associated with a defined skill set, the Skill Set Matcher component produces a list of several ME candidates to review the information item (configurable amount of ME candidates). In some embodiments, the system contacts candidates with an email such as the one shown in FIG. 63.

Figure 64:
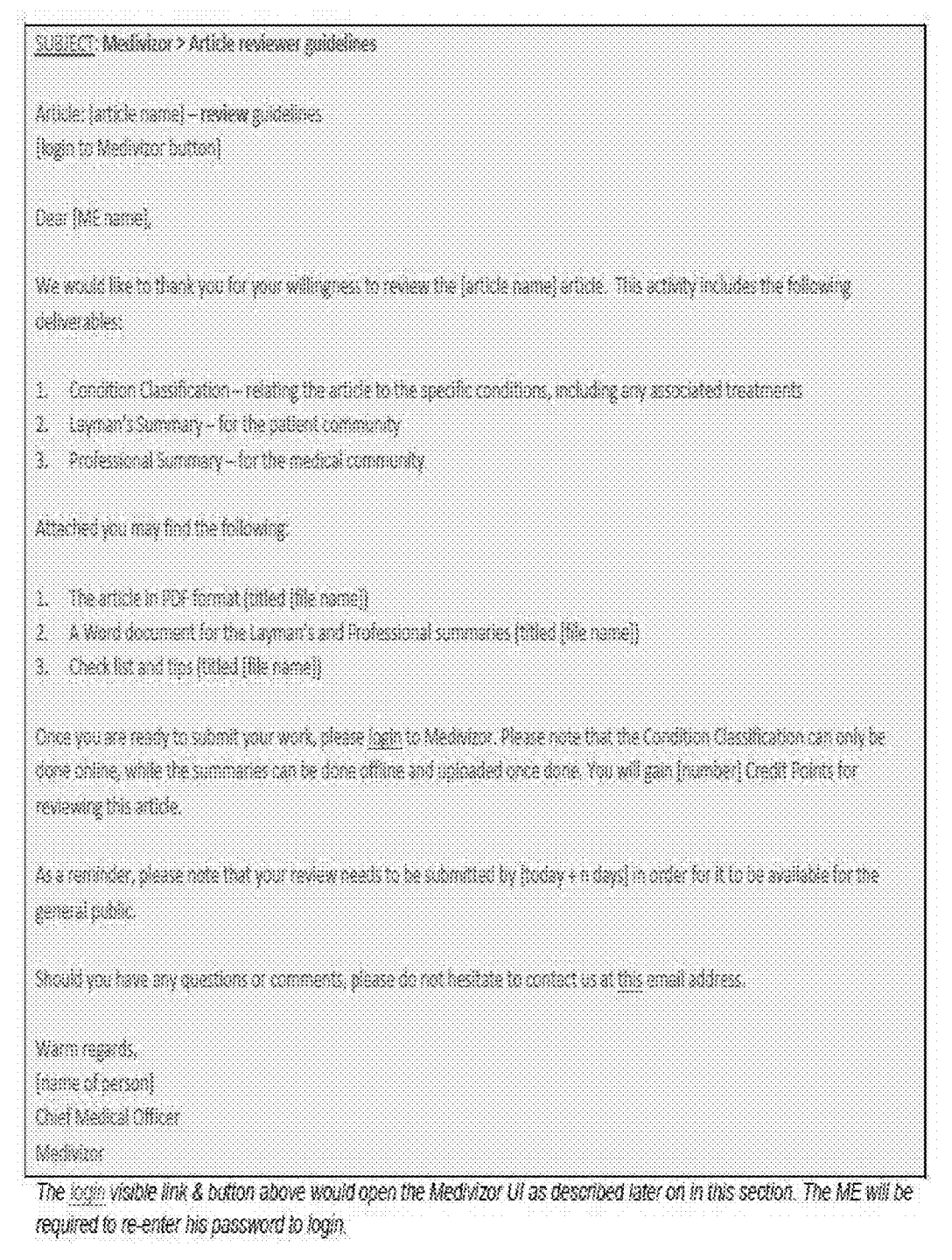

Additional email templates may include different layout and sample text as wireframes. The key specifics include the process flow, automation required, dynamic data that needs to be put into the template, the need to generate automatic emails, the specific links and activities to be supported by the MEs and the system. In some embodiments, an ME candidate that accepts the reviewer activity selects the link as demonstrated above. In some embodiments, assuming it was the ME to acknowledge the task, a reviewer guidelines email is sent to him by the system with the information such as the one shown on FIG. 64.

In some embodiments, if no ME candidate responses within a configurable duration, the Skill Set Matcher is once again utilized and an email is sent to another set of ME candidates. In some embodiments, this might be monitored manually and/or automated.

Figure 65:
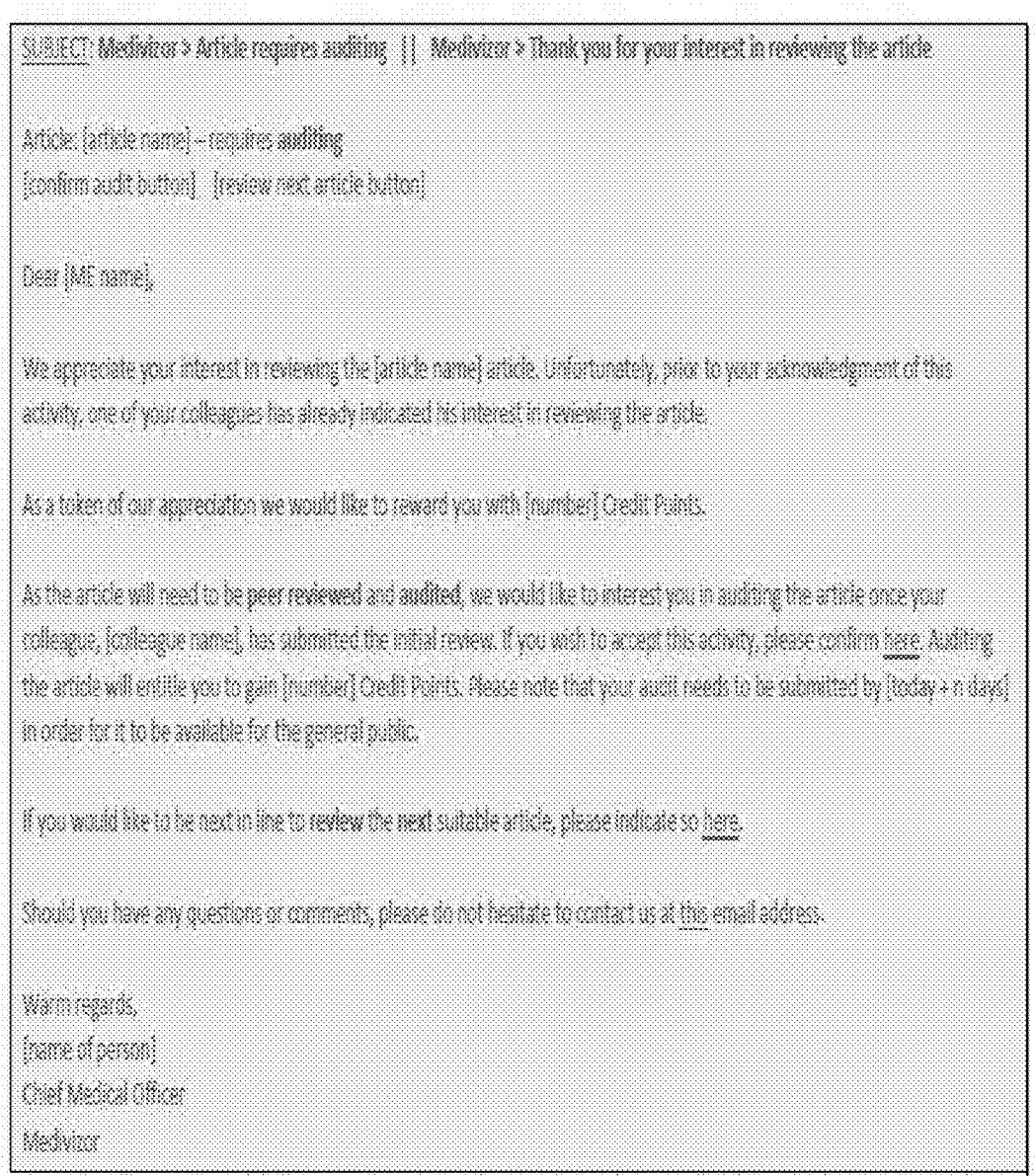
FIG. 65 illustrates features of some embodiments of the present invention.

In some embodiments, if an ME candidate wishes to review the information item but the reviewer activity has already been assigned to another ME, then they system sends an email such as the one shown on FIG. 65.

In some embodiments, as per the guidelines received in the reviewer guidelines email, the ME Reviewer has one or more of the following tasks to perform:

Condition Classification—the prime method by which the system will identify which End Users and Medical Professionals will be notified of the new information.

Layman's Summary—a way to describe to the lay person (the End User) what this new information is about and potentially what action might they be able to take in light of it (e.g. discuss with their doctor).

In some embodiments, information that may include, but is not limited to, information items and/or layman's summar(ies) of an information item are evaluated for readability using an automated tool and/or metric such as Flesch-Kinkaid Reading Grade Level. In some embodiments, the measurement of readability is automated to determine the grade level of the information such as the layman's summary. In some embodiments, based, at least in part, on the automatic grade level determination, the system determines whether the reading level is appropriate for a user or group of users. In some embodiments, based, at least in part, on the automatic grade level determination, the information may be reviewed, edited, or otherwise modified to accommodate one or more users with varying reading levels. In some embodiments, based, at least in part, on the automatic grade level determination, the one or more versions of the information may be created to accommodate one or more users with varying reading levels.

In some embodiments, the method uses the Flesch-Kinkaid grade level evaluation to automatically assesses the readability of a written text. In some embodiments, the readability of a given text is determined independent of the group of people reading a text. In some embodiments, the Flesch-Kinkaid grade level provides a sufficient approximation of the grade level readability of a written text.

In some embodiments, the Flesch-Kinkaid grade level is a function of the average number of syllables per word and the average number of words per sentence as shown in the following formula:

0.39 (total words/total sentences)+11.8 (total syllables/total words)−15.59

In a non-limiting example, the Flesch-Kincaid Grade Level is calculated in Table 1 below.

TABLE 1

Readability Statistics

| Counts | |
|---|---|
| Words | 870 |
| Characters | 4315 |
| Paragraphs | 30 |
| Sentences | 47 |

| Average | |
|---|---|
| Sentences per Paragraph | 4.7 |
| Words per Sentence | 16.9 |
| Characters per Word | 4.8 |

| Readability | |
|---|---|
| Passive Sentences | 6% |
| Flesch Reading Ease | 51.5 |
| Flesch-Kincaid Grade Level | 10.2 |

In some embodiments, word processing programs such as Microsoft Word include a tool that can assess the Flesch-Kinkaid grade level of text in a Word document.

In some embodiments, other methods to determine the reading level are used in the present invention. In some embodiments, readability depends on other factors that may include, but is not limited to, visual layout and content.

In some embodiments, the automatic reading level determination using the Flesch-Kinkaid method or equivalent allows evaluation and modification, if required, of complex information such as medical and scientific material for users. In some embodiments, the readability level of the information items are grade 15 to 16. In some embodiments, based at least in part by the grade level determination, the information item and/or layman's summary is amended to readability level of grade 10 to 12. In some embodiments, information may be presented below a 10th grade readability levels.

In some embodiments, the information such as information items or layman's summary are amended based, at least in part, on the Flesch-Kinkaid formula. In some embodiments, the information is amended by reducing the number of syllables in words and the number of words in sentences to result in lower Flesch-Kinkaid grade levels that are easier to read and understand than those with higher grade levels.

Professional Summary—a brief summary for medical professionals intended to spare them the time of reading the full information item by explaining briefly what's new about this and how does it relate to other published material they might have read or has been published about this topic.

In some embodiments, the Layman's Summary and the Professional Summary can be done offline utilizing the Word Template provided in the reviewer guidelines email. In some embodiments, the Condition Classification needs to be done online and/or offline.

In some embodiments, the system includes a MS-Word Template for Review. In some embodiments, the use of an MS-Word template is to allow for both instructions and capturing draft and final inputs/analysis of the information items by the reviewer that can be done offline using MS-Word, or equivalent. In some embodiments, the Word Template may include includes 2 sections—one for the Layman's Summary and one for the Professional Summary; each editable summary is capped to a configurable amount of characters; the ME can only insert his text in the specified location; and/or each section includes a short & focused 'check list & tips' explaining how to fill in the document and some general tips (e.g. encouraging the ME to use specific formatting, to summarize at the end in short bullets etc.).

In some embodiments, the specific (per Condition) tips were provided with the reviewer guidelines email. For convenience (as the ME might work offline), these could be added as well as an embedded object within the Word Document.

Figure 66:
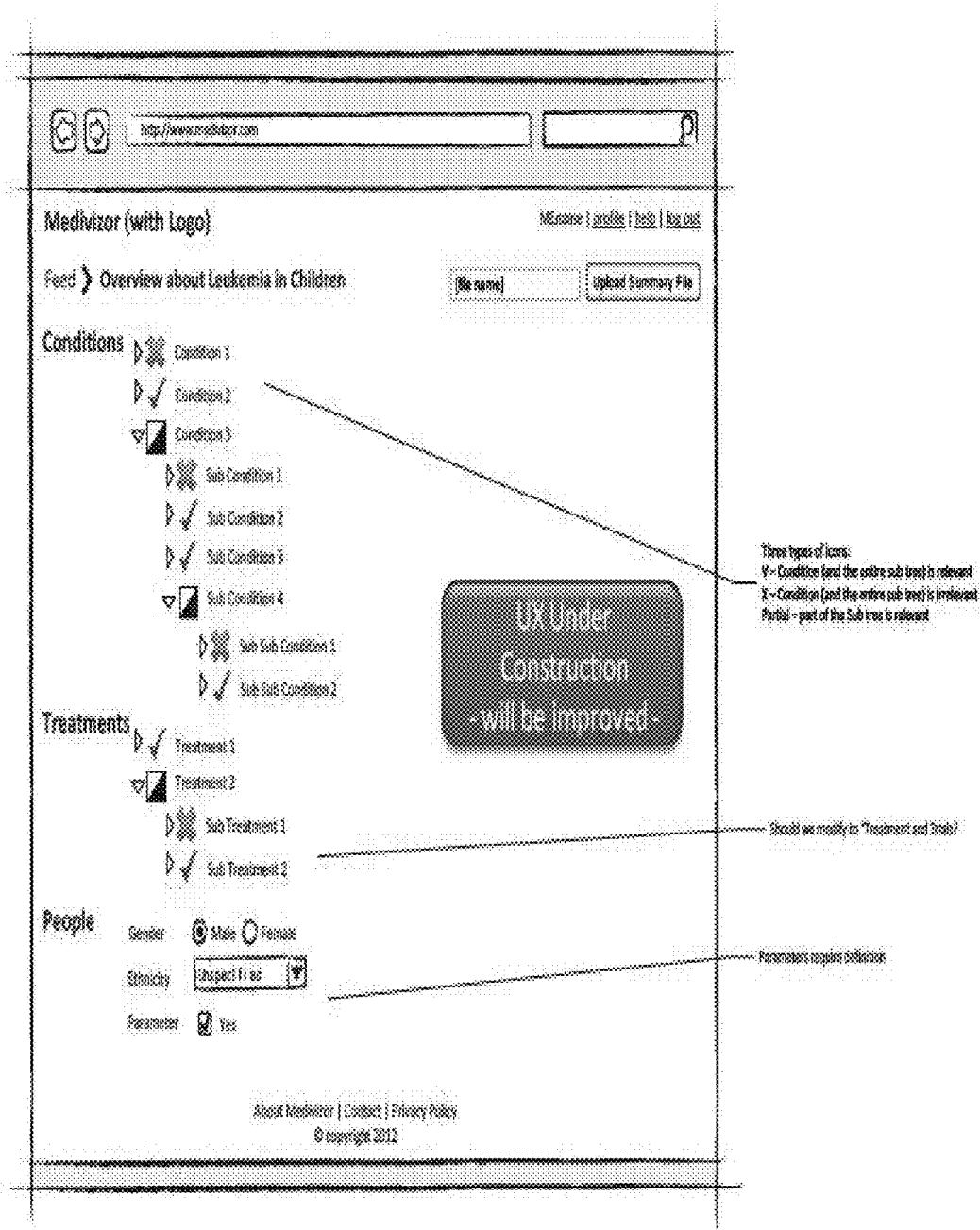
FIG. 66 illustrates features of some embodiments of the present invention.

In some embodiments, the system includes an Online Tool for Submitting Review. In some embodiments, once the ME Reviewer is ready to deliver his work, he needs to open the activity in the system (online, either via his account and/or using the link provided in the reviewer guidelines email) and feed the relevant information. In some embodiments, the UI used in the process includes that shown on FIG. 66.

In some embodiments, the system includes Auditing a New Information item. In some embodiments, the quest to find an ME Auditor begins immediately when an ME Reviewer is identified (i.e. when the ME acknowledges the reviewer activity as described above). The Skill Set Matcher is utilized and an email is sent to a set of ME candidates. The ME candidates for auditing might be those that were initially identified as candidates for the reviewer activity (besides the one that actually became the reviewer). In some embodiments, the system approaches the candidates with an email such as the one shown in FIG. 67.

In some embodiments, an ME Auditor may be identified before the ME Reviewer. This happens when searching for an ME to review an information item, and one of the candidates replies that he wishes to audit the information item. In this case, there is no need for the Skill Set Matcher to search for an ME Auditor as described above.

In the case of no ME candidate responses within a configurable duration, the Skill Set Matcher is once again utilized and an email is sent to another set of ME candidates. In some embodiments, this may be monitored manually and/or automated.

In some embodiments, an ME candidate that accepts the auditor activity selects the link as demonstrated above. In some embodiments, assuming it was the ME to acknowledge the task, an auditor confirmation email is sent by they system with information shown on FIG. 68, for example.

Figure 69:
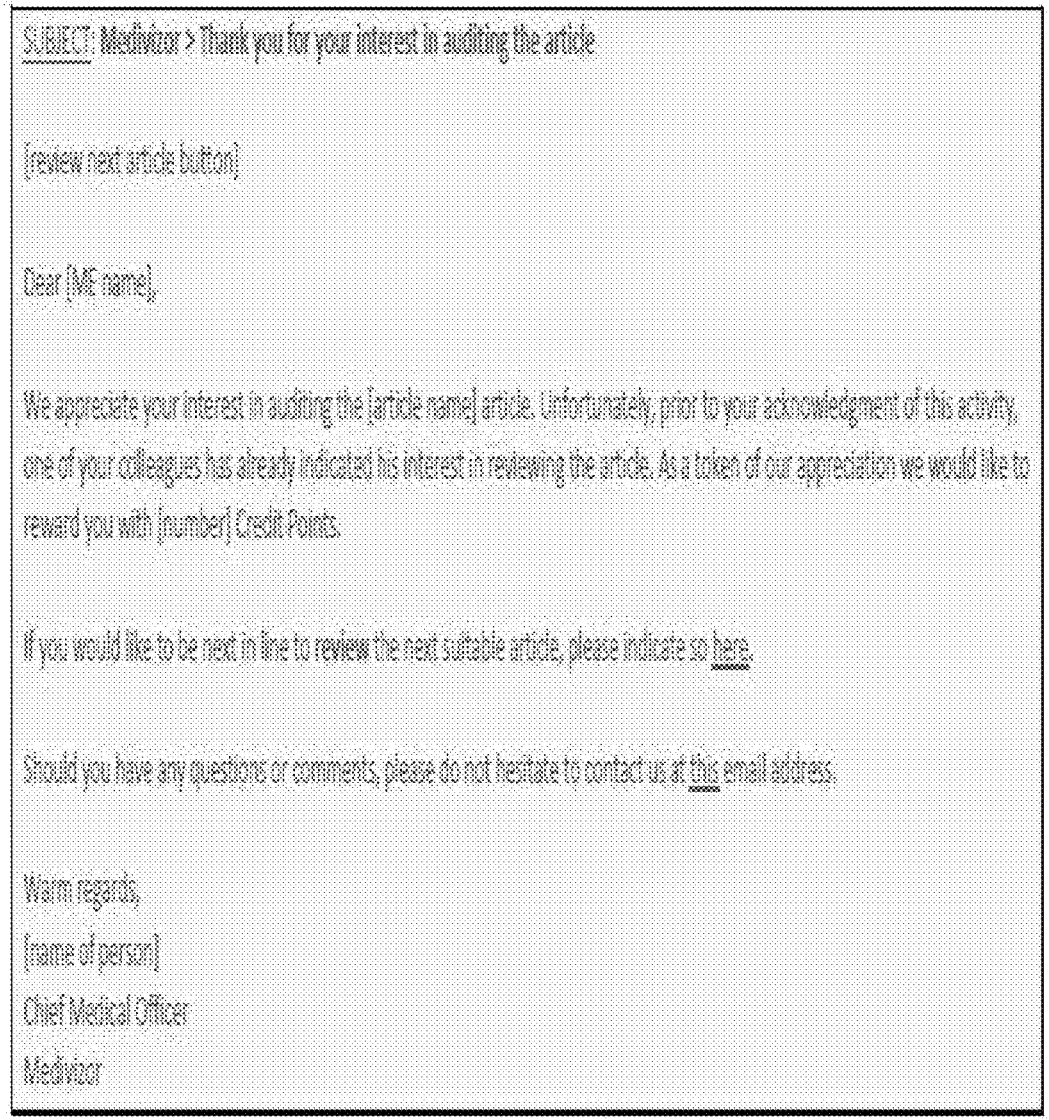
FIG. 69 illustrates features of some embodiments of the present invention.

In some embodiments, in case the audit activity has already been assigned to another ME, then the system sends an email such as the one shown on FIG. 69.

In some embodiments, once the ME Reviewer has completed and submitted his work, the system sends the following auditor guidelines email to the nominated ME Auditor as shown on FIG. 70, for example.

In some embodiments, as per the guidelines received in the auditor guidelines email, the ME Reviewer has three main tasks to perform that may include, but is not limited to:

Peer review the Condition Classification (by the ME Reviewer)

Peer review the Layman's Summary (by the ME Reviewer)

Peer review the Professional Summary (by the ME Reviewer)

In some embodiments, the Layman's Summary and the Professional Summary are peer reviewed using the Word Template. In some embodiments, the Word Template includes, but is not limited to, similar in nature to the reviewer template; 2 sections—one for the Layman's Summary and one for the Professional Summary; each editable summary is capped to a configurable amount of characters; the ME can only insert his text in the specified location; each section contain two areas—top "read only" area displays the original reviewer text and the lower area displays an exact copy of the original reviewer text but is editable, allowing the auditor to modify the text; revision marks are enabled and cannot be removed—the ME can show 'final markings' if he wishes to see his modified text without the revision marks; each section includes a short & focused 'check list & tips' explaining how to fill in the document and some general tips (e.g. encouraging the ME to use specific formatting, to summarize at the end in short bullets etc.).

In some embodiments, specific (per Condition) tips may be provided with the auditor guidelines email. In some embodiments, for convenience (as the ME might work offline), these are added as well as an embedded object within the Word Document.

Figure 71:
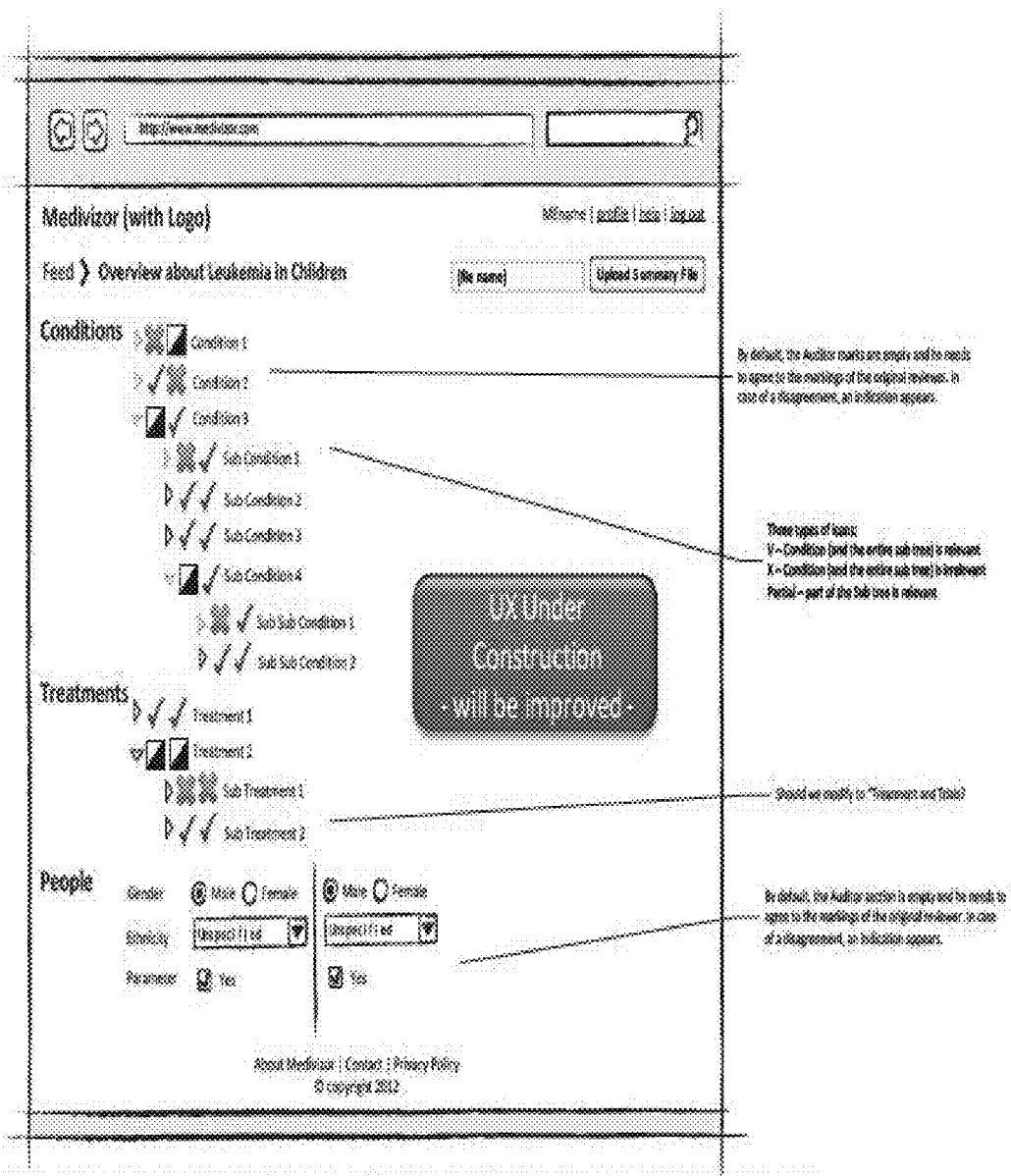
FIG. 71 illustrates features of some embodiments of the present invention.

In some embodiments, the Condition Classification is completed online (access is online either via the ME account or using the link provided in the auditor guidelines email). In some embodiments, the UI is shown on FIG. 71.

In some embodiments, assuming an ME Auditor wishes to start a discussion with the ME Reviewer (for clarifications etc.), the Discussion Board may be utilized for this purpose. In some embodiments, the ME Auditor has the ability to 'Start a Discussion' with a button added to the UI shown on FIG. 71.

In some embodiments, the system includes Dispute Resolution. In some embodiments, the ME Reviewer and the ME Auditor might not share the same view. In some embodiments, in case of a dispute with the Condition Classification, the system will automatically initiate an editing activity. In some embodiments, in case the ME Auditor made some modifications to the Layman's Summary or the Professional Summary, he is then required to note it these are just 'minor changes'. In some embodiments, only if the changes are not considered as minor, then an editing activity is called for (even if there is no dispute with the Condition Classification).

Figure 72:
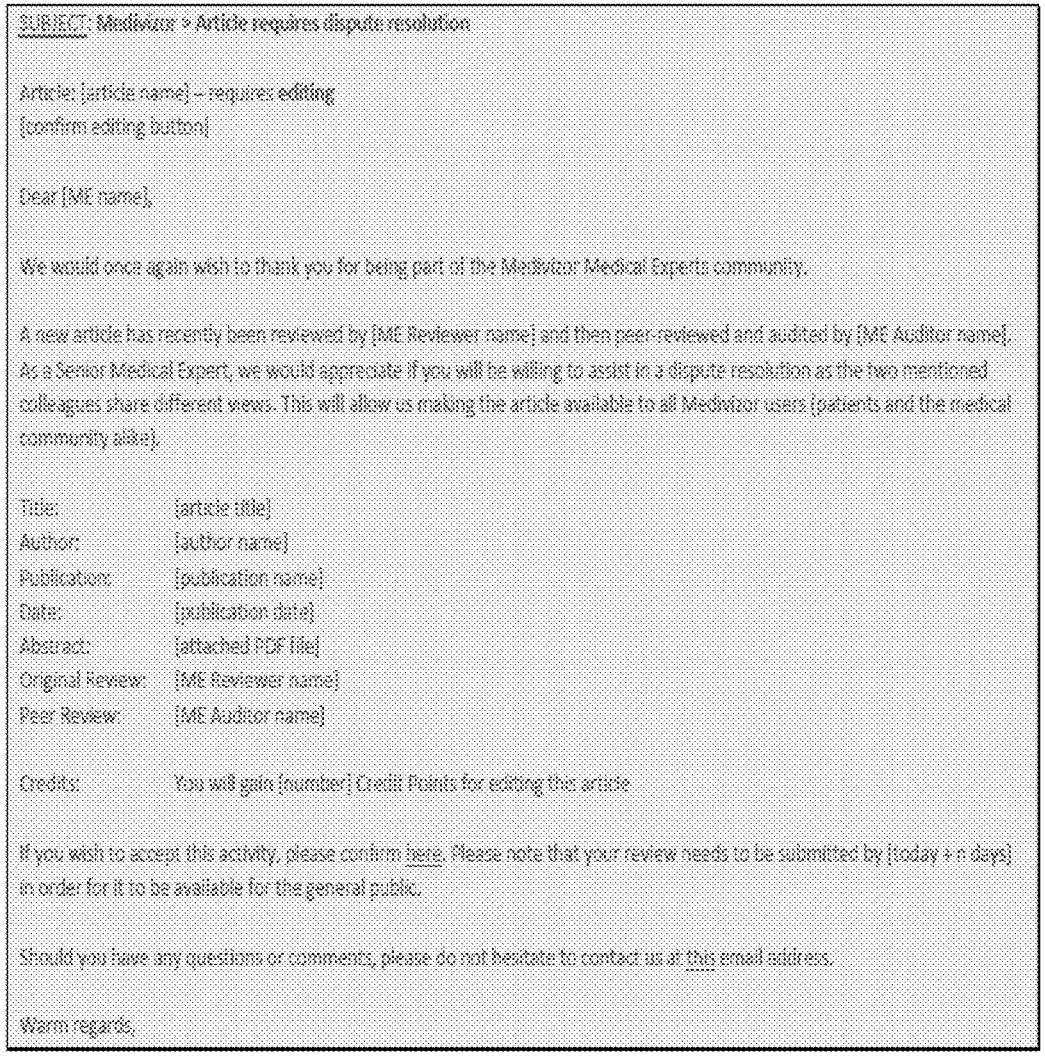
FIG. 72 illustrates features of some embodiments of the present invention.

In some embodiments, in case an editing activity is required, a quest to find an ME Editor begins. The Skill Set Matcher is utilized and an email is sent to a set of ME candidates (those that are defined as Senior Medical Experts in the relevant field). The ME candidates for editing might be those that were originally identified as candidates for reviewing or auditing (of course this list excludes the ME Reviewer and the ME Auditor). The system approaches the candidates with an email such as the one shown on FIG. 72.

In some embodiments, an ME candidate that accepts the editing activity selects the link as described above. In some embodiments, assuming it was the ME to acknowledge the task, an editing guidelines email is sent such as the one shown on FIG. 73. In some embodiments, in case no ME candidate responses within a configurable duration, the Skill Set Matcher is once again utilized and an email is sent to another set of ME candidates. In some embodiments, this is either monitored manually and/or automated.

Figure 74:
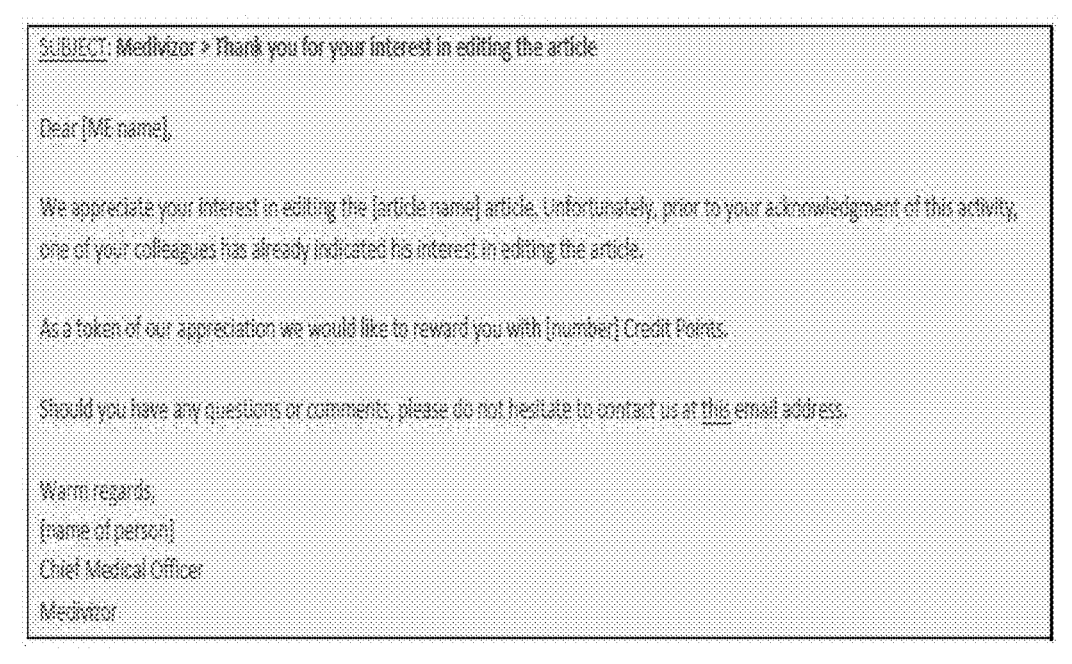

In some embodiments, if an ME candidate wishes to edit the information item but the editing activity has already been assigned to another ME, then the system sends an email such as the one shown on FIG. 74.

In some embodiments, as per the guidelines received in the editing guidelines email, the ME Editor tasks may include, but are not limited to:

Take a final decision regarding the Condition Classification

Decide regarding the official wording used in the Layman's Summary

Decide regarding the official wording used in the Professional Summary.

In some embodiments, the Layman's Summary and the Professional Summary are edited using the Word Template. In some embodiments, the Word Template may include, but is not limited to: similar in nature to the auditor template; include 2 sections—one for the Layman's Summary and one for the Professional Summary; each editable summary is capped to a configurable amount of characters; the ME can only insert his text in the specified location; each section may contain three areas—the top "read only" area displays the original reviewer text, the middle "read only" area displays the auditor modified text where revision marks are enabled, the editor can decide if to view the auditor's section with or without revision marks (a button on the form), and the lower area is intended for the editor's final version where he has an option (button on the form) to copy the original text or the audited text and/or where he can also decide to write from scratch and/or copy/paste portions of the summaries by his colleagues; each section includes a short & focused 'check list & tips' explaining how to fill in the document and some general tips (e.g. encouraging the ME to use specific formatting, to summarize at the end in short bullets etc.).

Figure 75:
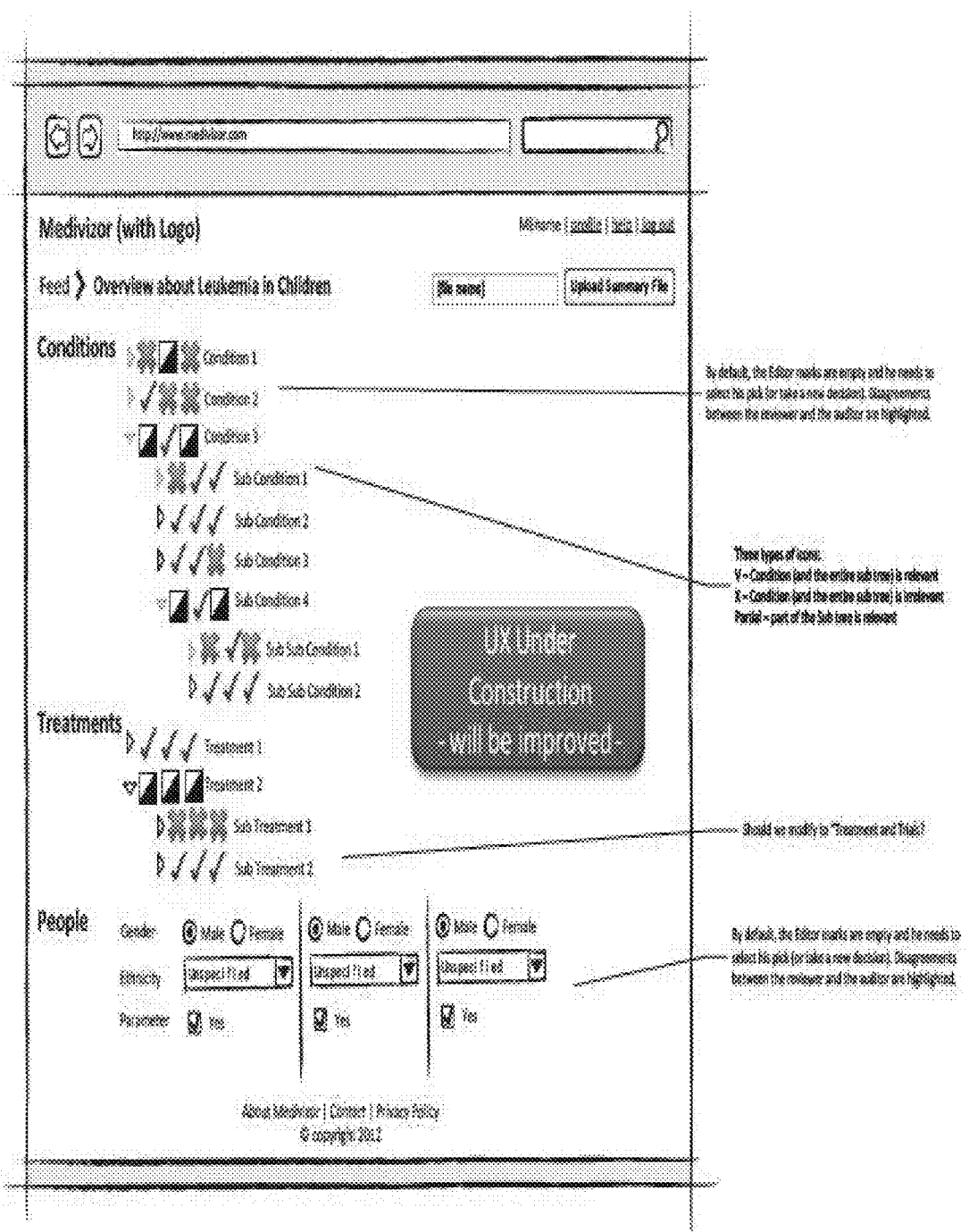
FIG. 75 illustrates features of some embodiments of the present invention.

In some embodiments, specific (per Condition) tips are provided with the editor guidelines email. In some embodiments, for convenience (as the ME might work offline), these would be added as well as an embedded object within the Word Document. In some embodiments, the Condition Classification needs to be done online (access is online, either via the ME account or using the link provided in the editing guidelines email). An example UI for use in this process is shown on FIG. 75.

In some embodiments, once the ME Editor completes his editing work, the information item is considered as 'ready for publication'.

In some embodiments, the system includes Publication. In some embodiments, reviewing the new information, describing it, and classifying it culminates in its publication and making it available to various users. In some embodiments, at the end of the review process that classifies/tags the new information, describes it for lay people and professionals, and does so in an audited and reviewed fashion, it will be published expeditiously.

In some embodiments, at this stage, it enters a queue of work for the Medical Board Secretary. In some embodiments, the Medical Board Secretary reviews a checklist (that may be updated from time to time) and decides to publish it or perform other manual functions prior to publication. Upon publication, in some embodiments, the new information will be sent to users with conditions, treatments, demographics, etc. for which the information item is relevant will be notified. In some embodiments, Medical Professionals with associated patients or expertise and Medical Experts whose Skill Set Matcher identifies as relevant for the new information will also be notified. In some embodiments, such information notifications will depend on user preferences in terms of timing and content—as set in their preferences/settings.

Figure 76:
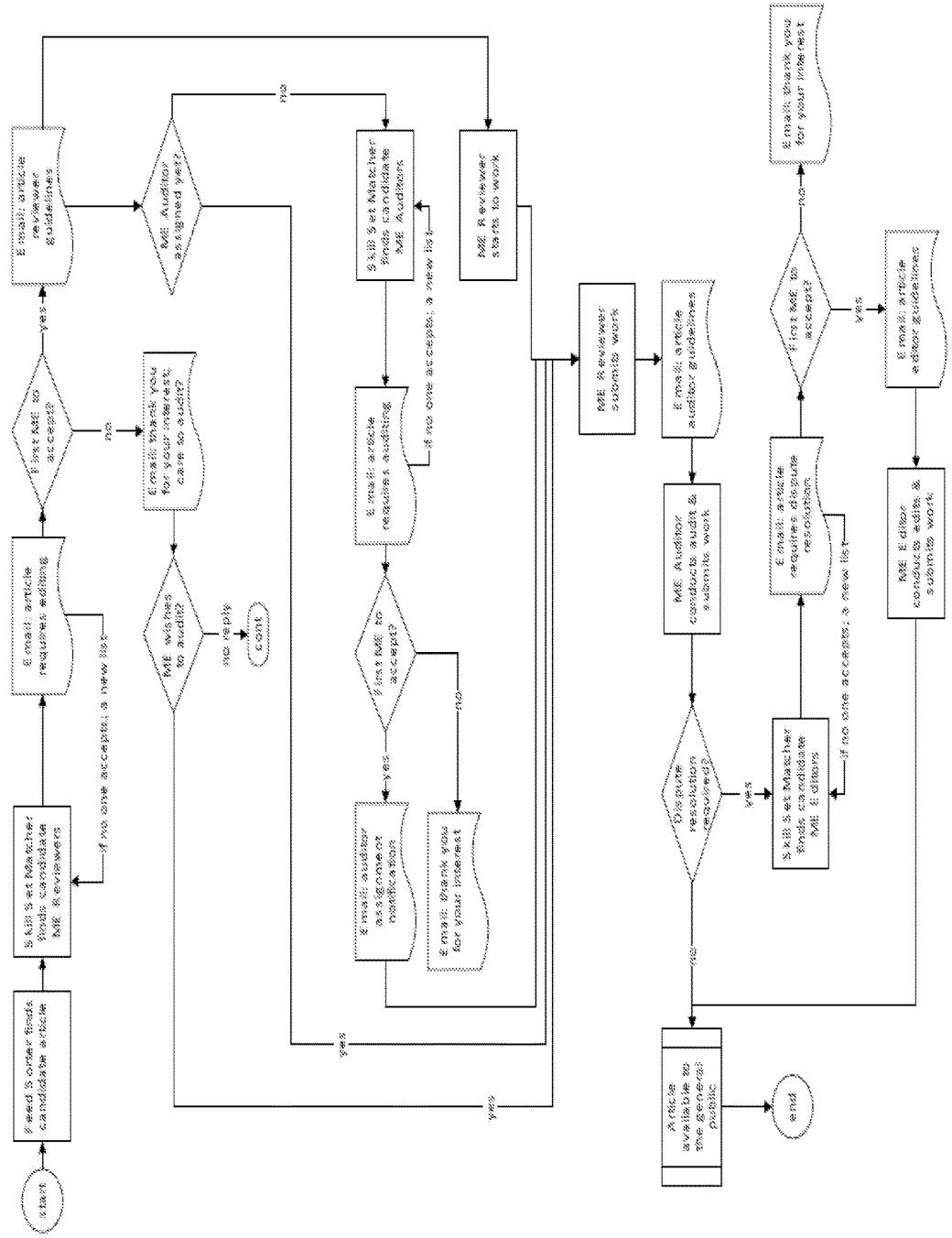
FIG. 76 illustrates features of some embodiments of the present invention.
Figure 77:
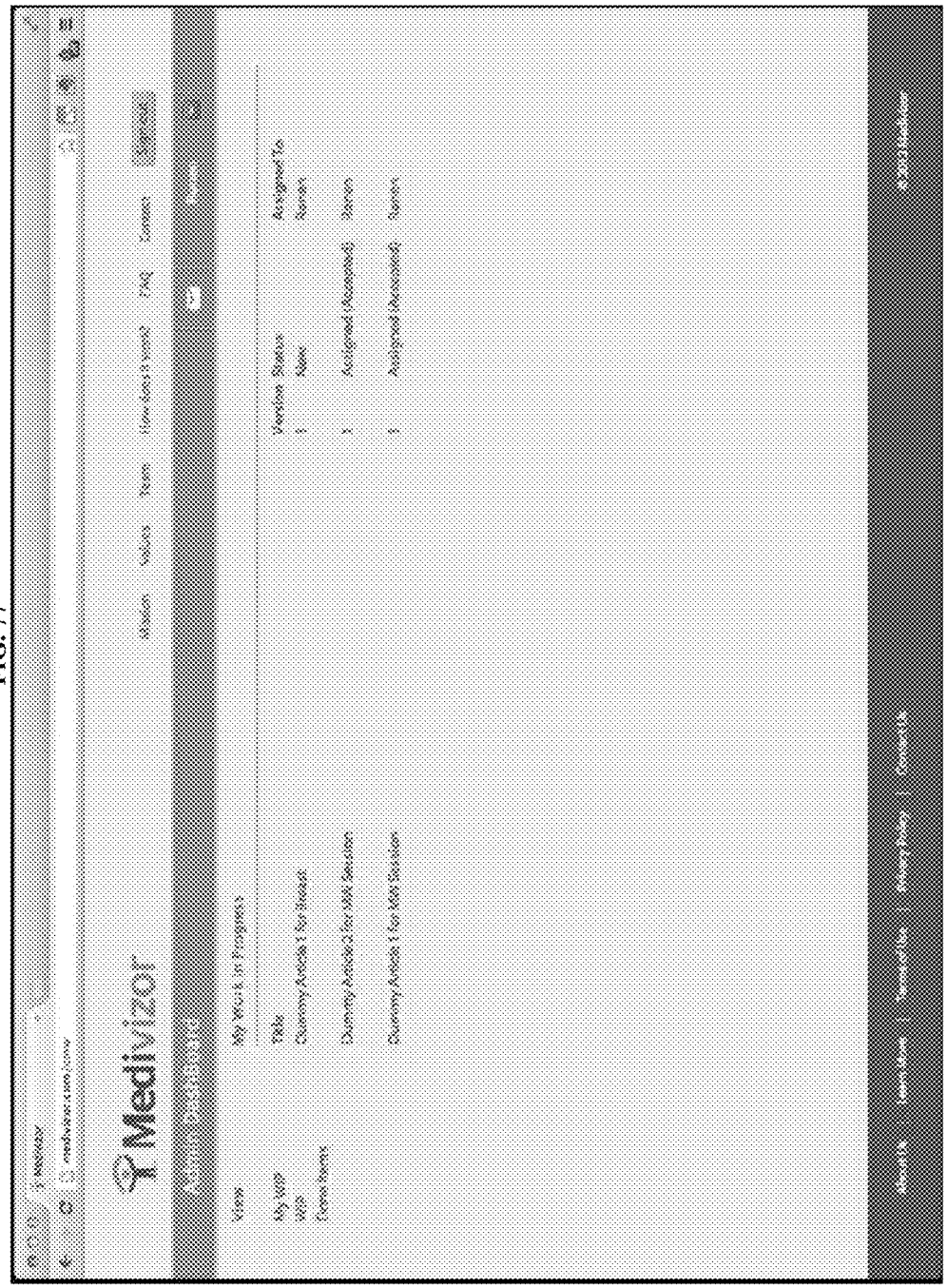
FIG. 77 illustrates features of some embodiments of the present invention.
Figure 78:
FIG. 78 illustrates features of some embodiments of the present invention.
Figure 79:
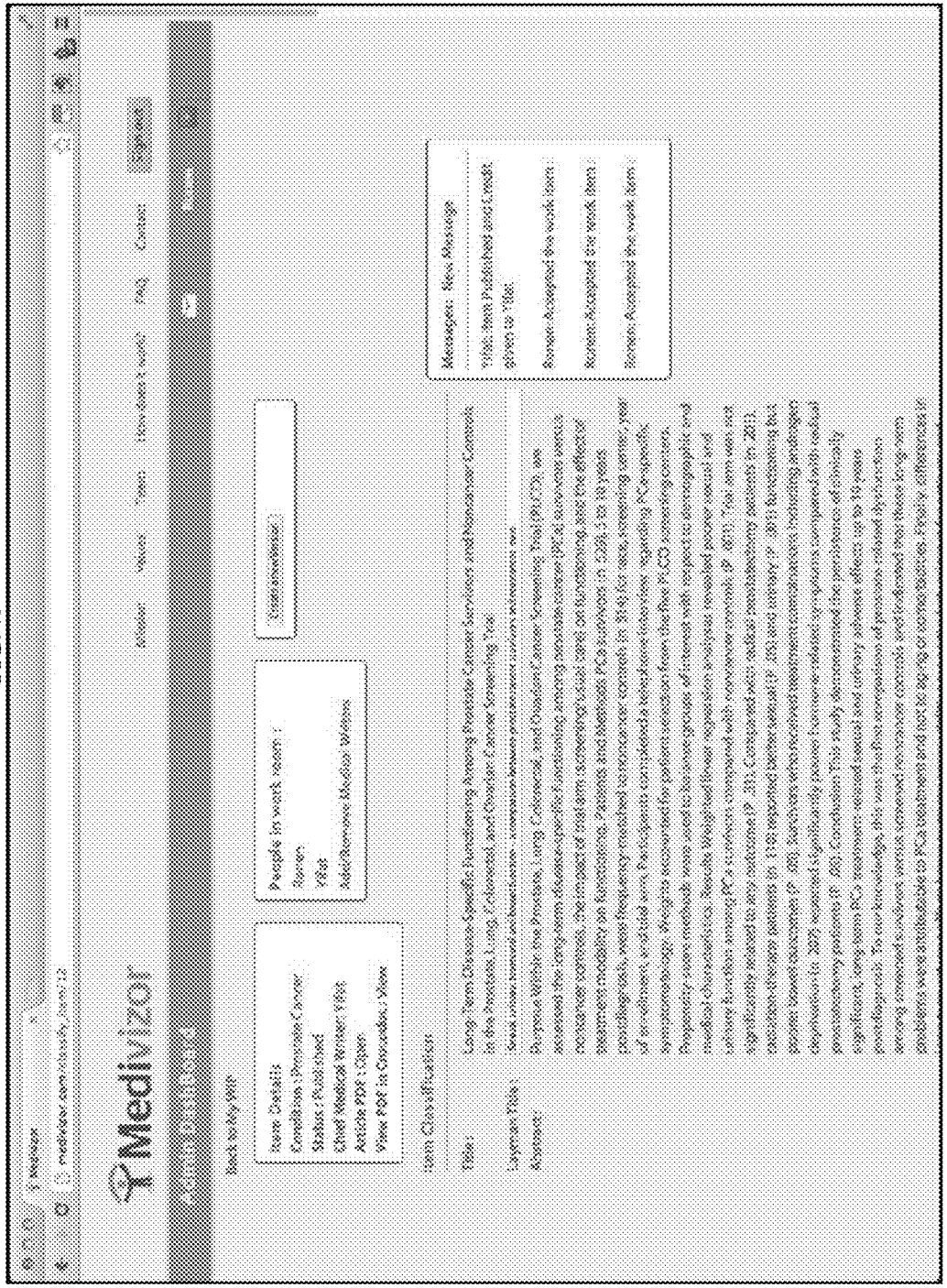
FIG. 79 illustrates features of some embodiments of the present invention.
Figure 80:
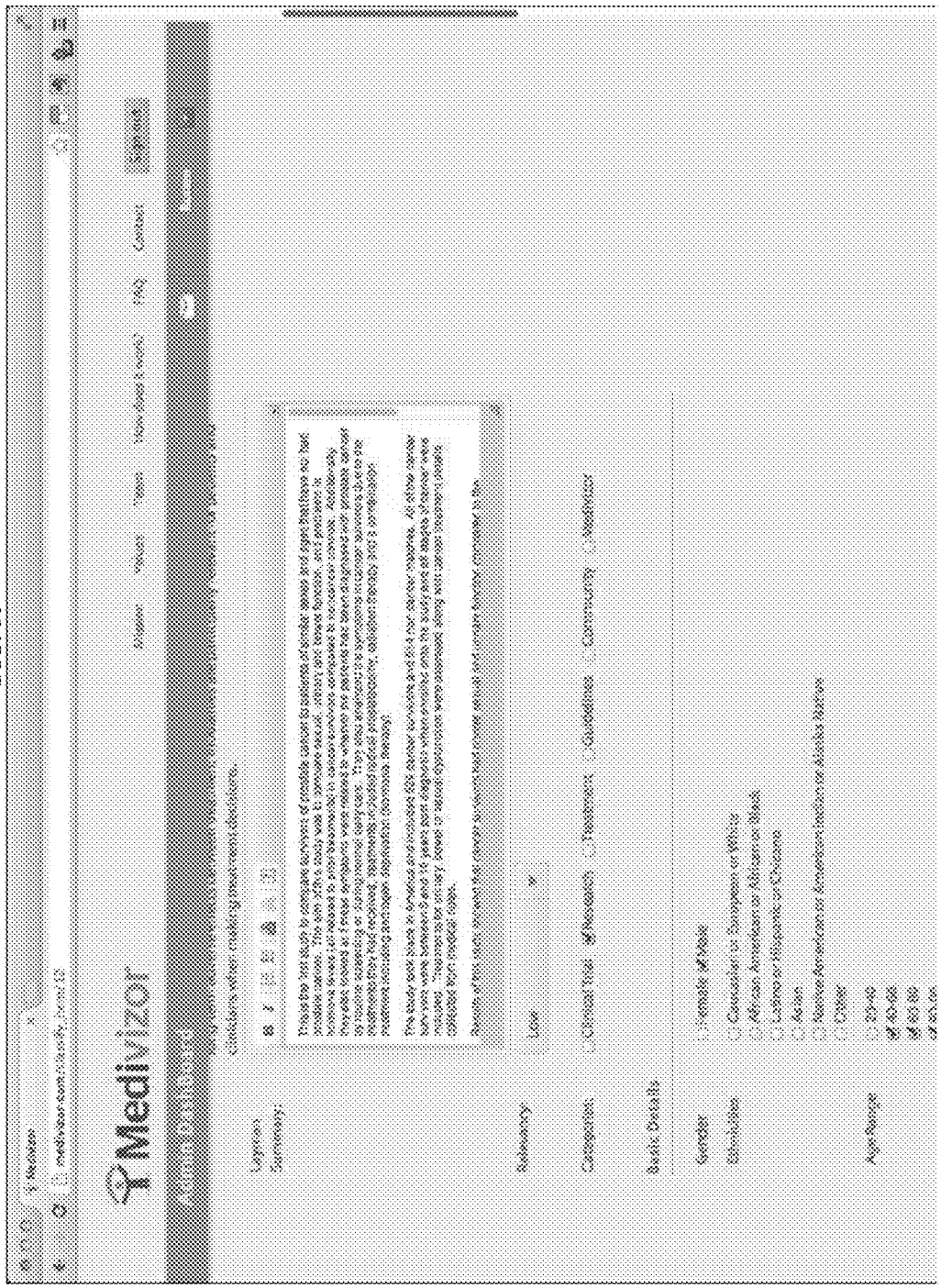
FIG. 80 illustrates features of some embodiments of the present invention.
Figure 81:
FIG. 81 illustrates features of some embodiments of the present invention.
Figure 82:
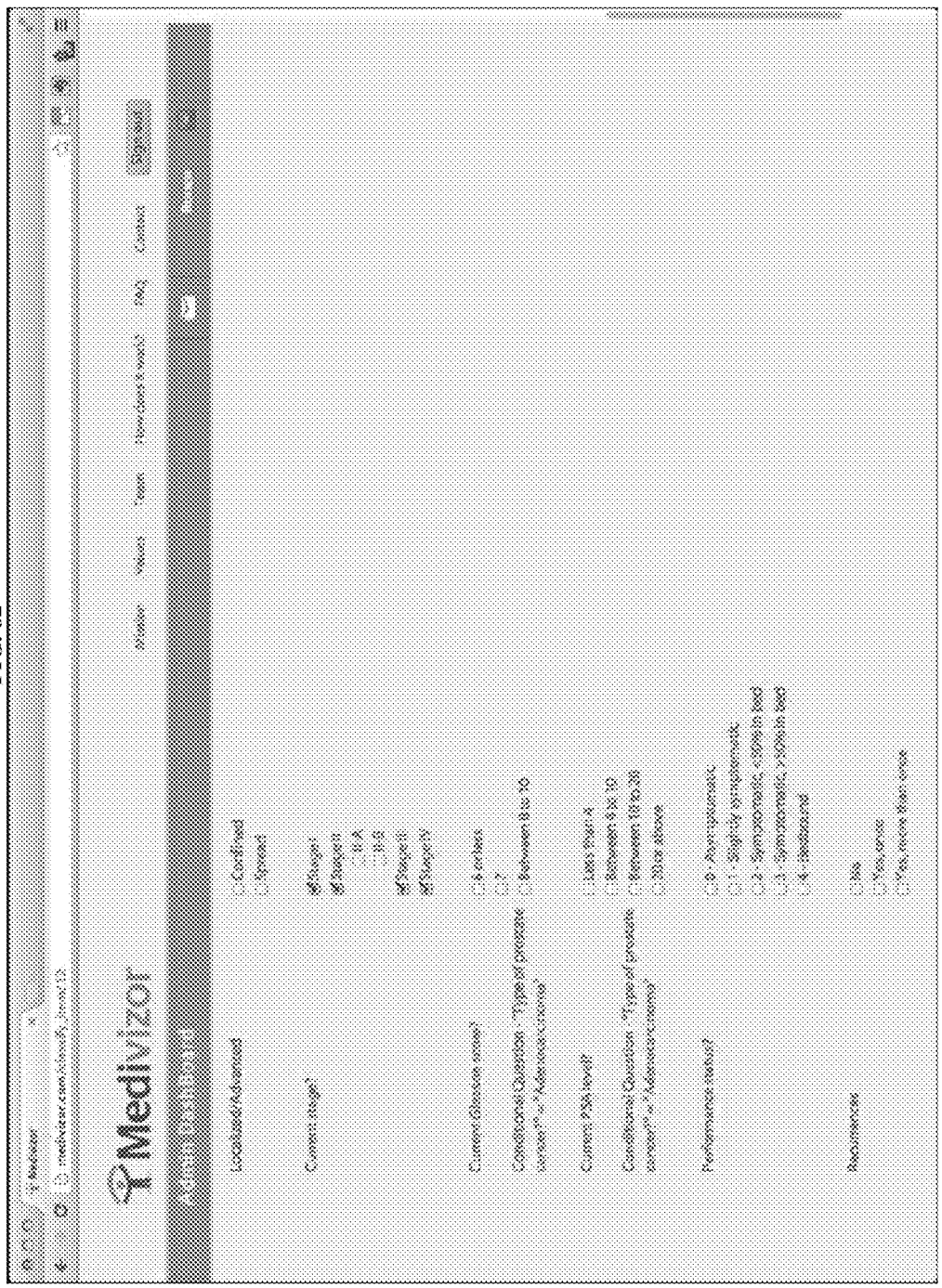
FIG. 82 illustrates features of some embodiments of the present invention.
Figure 83:
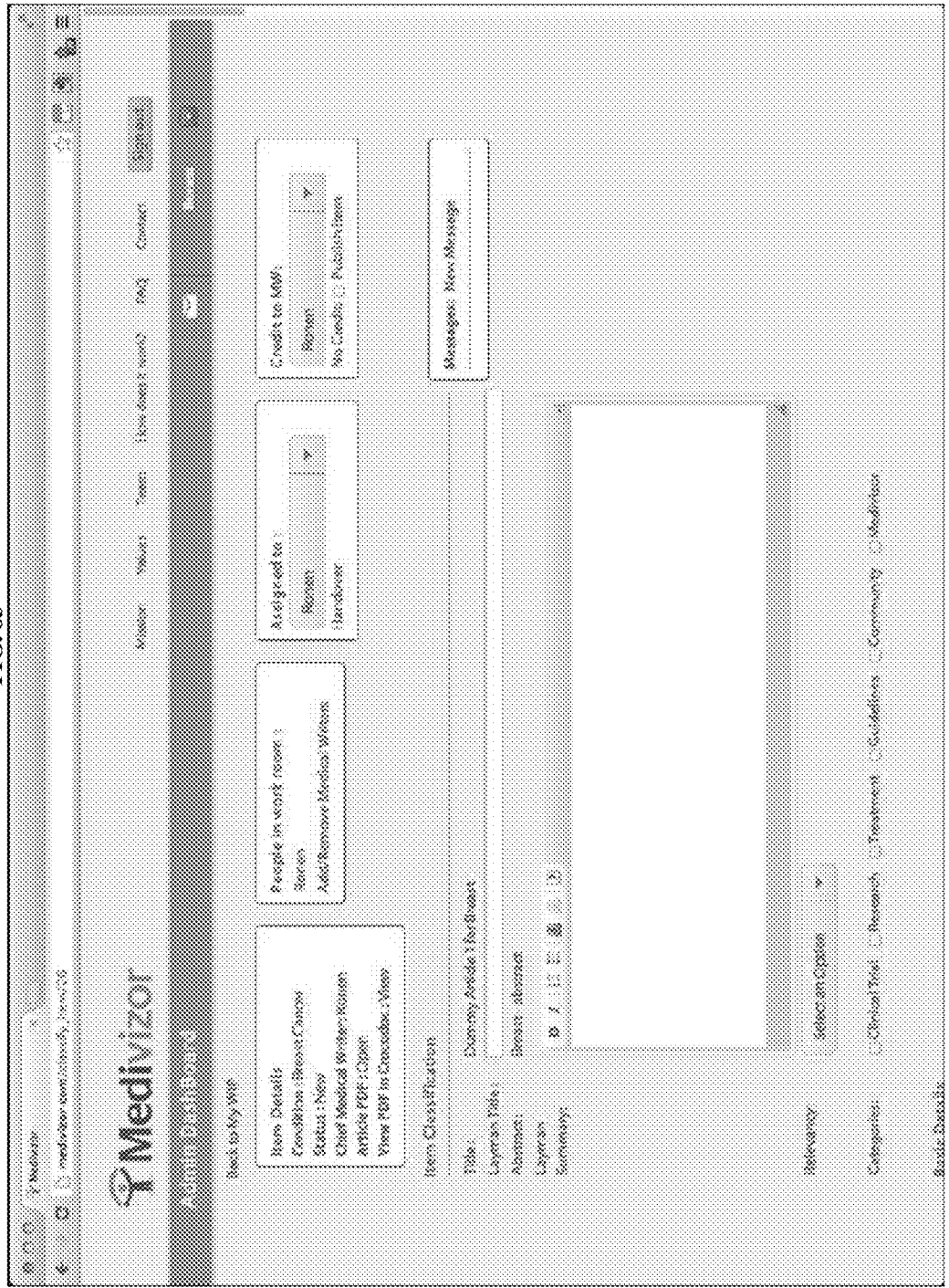
FIG. 83 illustrates features of some embodiments of the present invention.
Figure 84:
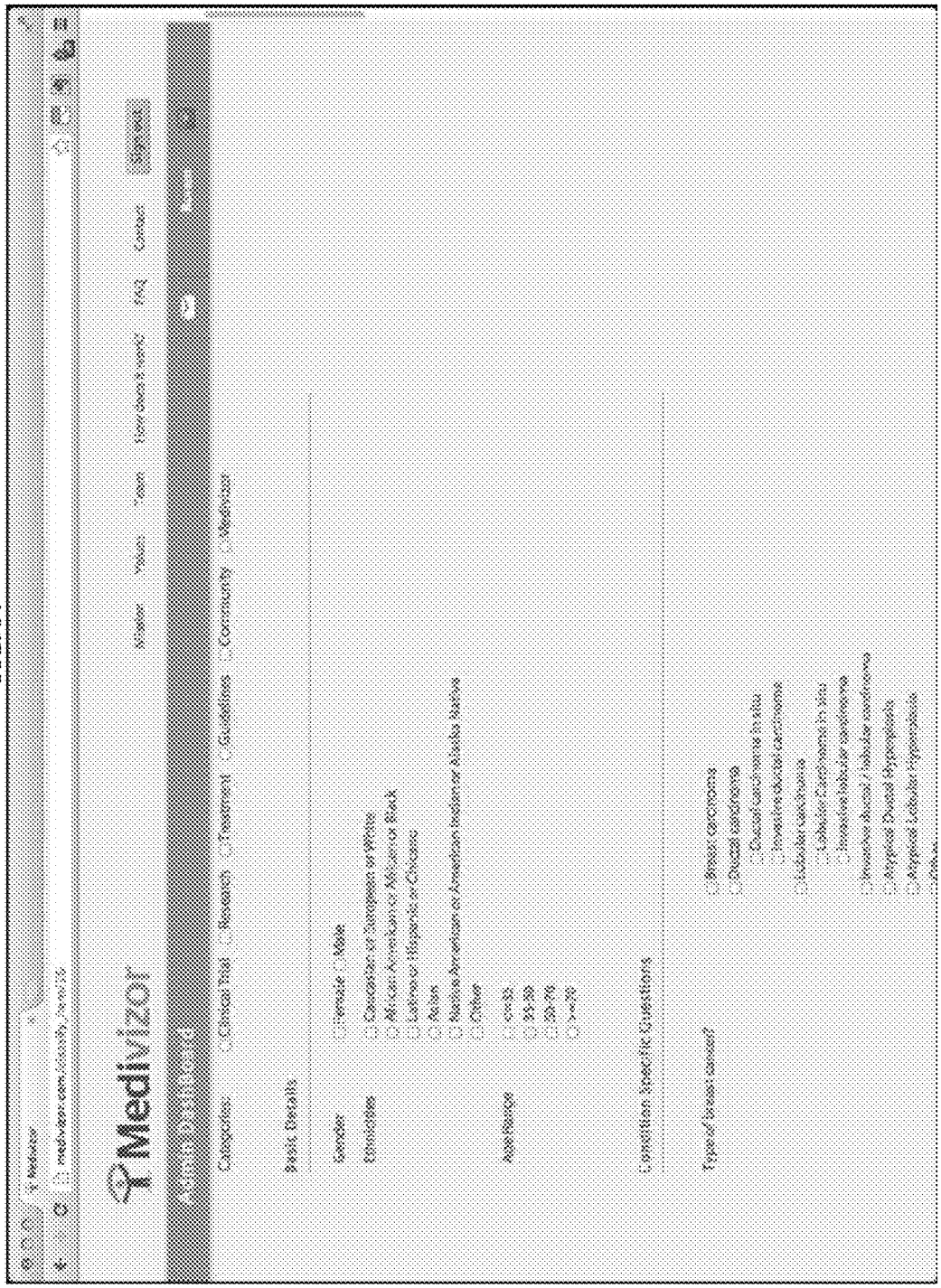
FIG. 84 illustrates features of some embodiments of the present invention.
Figure 85:
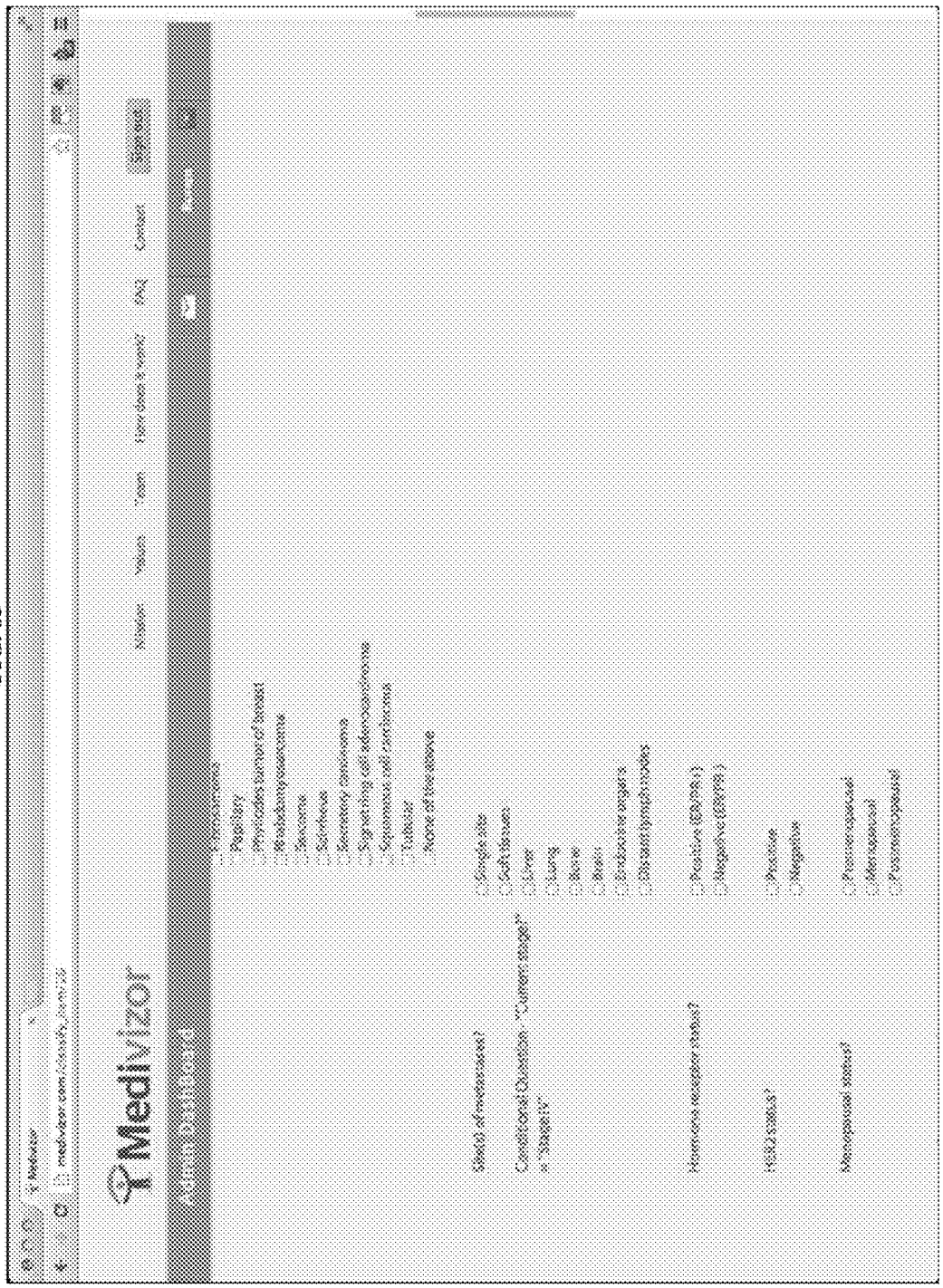
FIG. 85 illustrates features of some embodiments of the present invention.
Figure 86:
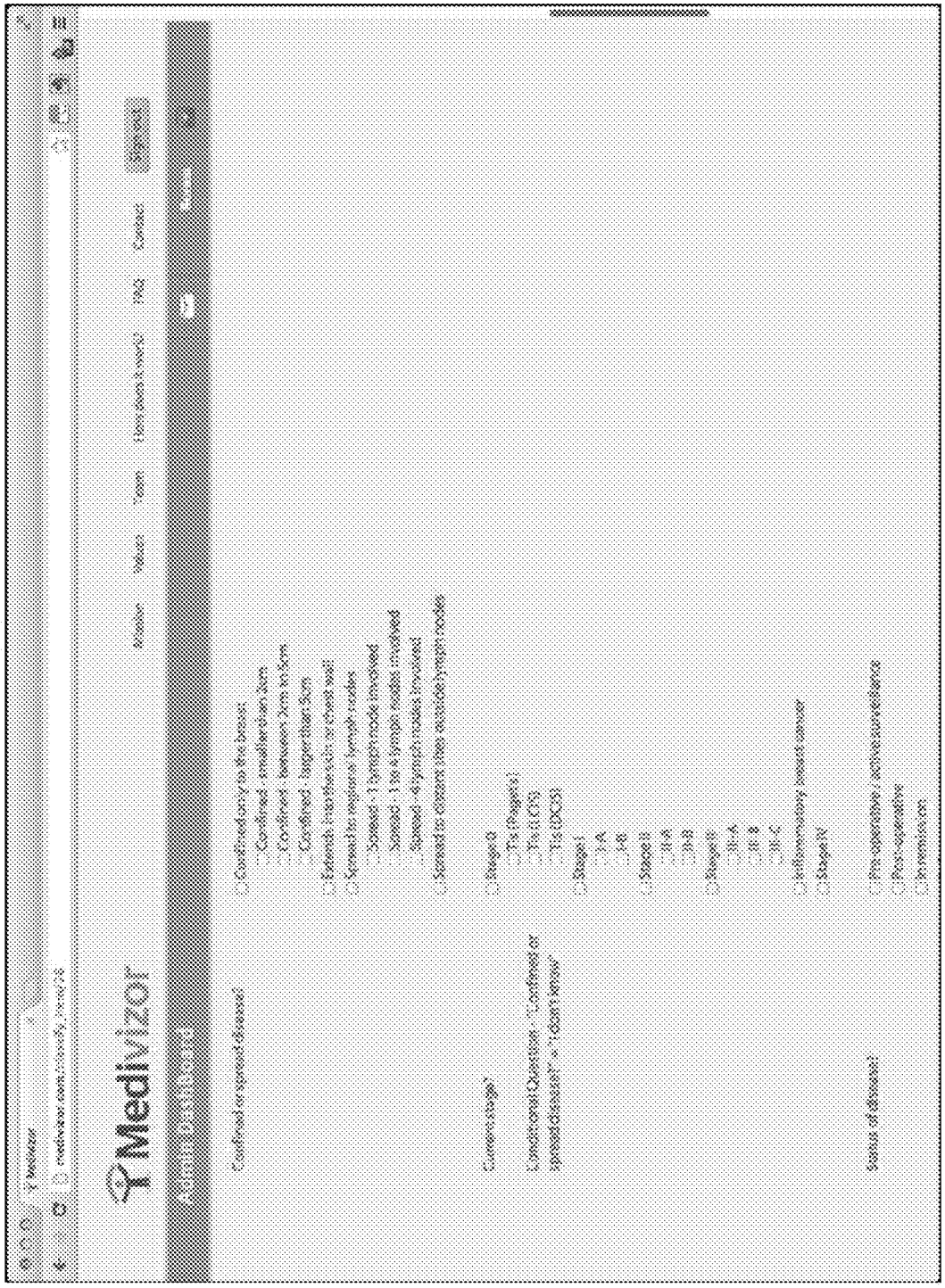
FIG. 86 illustrates features of some embodiments of the present invention.
Figure 87:
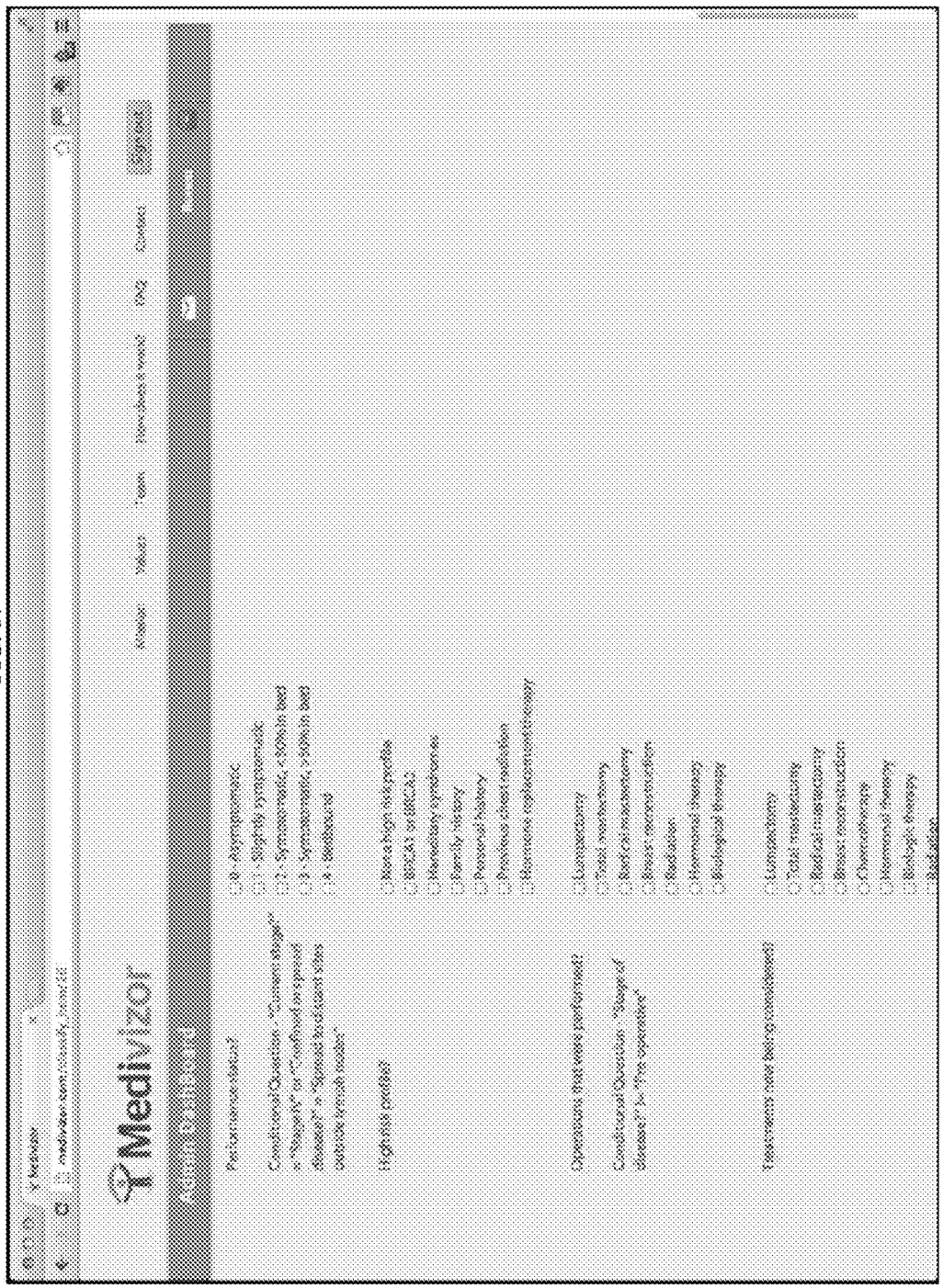
FIG. 87 illustrates features of some embodiments of the present invention.

In some embodiments, a Flow Diagram describing high-level details of the process is shown on FIG. 76.

In some embodiments, screen shots of the system of the present invention are shown on FIGS. 77-87.

In some embodiments, the system includes Author Initiated Reviews. In some embodiments, new material is classified and reviewed by the original creator of the new material—the original author (or institute). In some embodiments, information items (or any new information) would be submitted by the author of the new material and classified by them directly to the system so that it could be distributed to the relevant End Users and Medical Professionals in a timely manner (as soon as their information item is made available in any online form or even before then).

In some embodiments, this may be an exclusive access to authors and institutions will be part of the 'exclusive author initiated review' program In some embodiments, MEs that will be part of the above mentioned program will be able, via their online account, to initiate a review process based on their original information item (them being the original authors is not mandatory). Once doing so, the rest of the process is as described above (excluding the need to find an ME Reviewer), including the need to audit etc.

In some embodiments, a Discussion Board allows the MEs to collaborate and interact with each other about the new information and discuss aspects of classification/interpretation/relevance. In some embodiments, it is open only to internal users (and targeted specifically to the main use of MEs in their review process). In some embodiments, the discussions are in context of a specific information item—and about that information item.

In some embodiments, users other than End Users are automatically 'users' in the Discussion Board (i.e. can view, post etc.). In some embodiments, certain disclaimers apply (respect for others etc.).

In some embodiments, Board is visible only to MEs and other internal users.

In some embodiments, these appear as comments to a blog post where the blog post is the internal representation of the "new information" to which the comments relate.

In some embodiments, the forum is not moderated—though the administrator can remove posts and disable further updates or comments.

In some embodiments, the discussions are very much like comments to blog posts—therefore technologies of relevance can be applied here such as CMS/Joomla or Wordpress—and simplified/customized for this purpose.

In some embodiments, Medical Expert Account Views include Medical Experts (MEs) that have the ability to view and edit their account online. In some embodiments, the account information contains information of various types.

In some embodiments, the Account Profile includes, but is not limited to, basic contact information and information about their medical expertise and professional affiliations. In some embodiments, MEs would be added to the system by an administrator. In some embodiments, MEs would be able to log in and update their account details. In some embodiments, the ability to sign up as an ME would be enabled from the main system page.

In some embodiments, the present invention may include a Tasks Queue. In some embodiments, the list of current activities assigned to the ME including links to get more information about them. This could simply be a view on the email interactions and open tasks so the ME could review his workload and directly access the activities that need tending to.

In some embodiments, the system may include an Information item Feed. In some embodiments, the ME may want to be notified about a different set of filters—including multiple medical conditions, treatments, and domains. They may want distinction between information feed via email vs. online.

In some embodiments, the system includes, but is not limited to a Reward Program that is similar in notion to an airline's Frequent Flyer program. In some embodiments, one receives points by being active. In some embodiments, one receives more points for being very active; and can redeem them (assuming he stays active).

In some embodiments, Participants in the Reward Program include Medical Experts (ME) only. In some embodiments, the program may include other users as well.

In some embodiments, the system may include Gaining Points. In some embodiments, the Gaining points can be achieved, as an example, by MEs in the following ways:

Reviewing an information item: 100 points per each page of the information item

Auditing an information item: 30 points per each page of the information item

Editing an information item: 50 points per each page of the information item

If the ME reviewed an information item during the past 7 days: additional 25%

If the ME audited an information item during the past 7 days: additional 10%

If the ME audited an information item during the past 7 days: additional 15%

In some embodiments, redeeming points can be achieved by MEs in the following ways as an example:

Points never expire but are redeemable as long as the ME has been active (i.e. has gain points) in the past 100 days. Post this period, points become frozen.

Assuming the ME has frozen points; then by being active again (i.e. gaining points), points are made redeemable once again.

Retrieving a summarized information item: 20 points per each page of the information item.

In some embodiments, an alternative program implementation could be based on time as the determining factor—i.e. as long as an ME is active, then he is granted access In some embodiments, the system includes an Internal User Interface and/or a Manager User Interface. In some embodiments, the manager may require some process management UI where they can see activities, their status, and be able to manipulate status. In some embodiments, the main activities are reviewing of new material—assigning it to reviewers, auditors, and eventually, leading to its publication. In some embodiments, the Manager is often synonymous in this document with Medical Board Secretary.

In some embodiments, the system includes Other Internal Users. In some embodiments, these users here are paid to use the app. In some embodiments, a user interface facilitates more efficient use of their time (as opposed to updating database tables, XML files, or other manual operations).

In some embodiments, the system would have the following functions:

Crowdsourced selection of material—when people "Save/Bookmark/Favorite" an information item, it will score it higher for other users with the same conditions.

Crowdsourced highlighting of material—when people annotate material it will appear as highlighted by others and raise the score for the information item and section. Much like Kindle annotations work.

Crowdsourced treatment/medical professional selection—when users thumbs up/like/favorite any of these, it will raise their prominence for other users.

A-B Testing capabilities—the system would include two or more front ends and compare them quickly on different communities. In some embodiments, this could be relevant for the web site itself as well as inner pages of the app.

In some embodiments, aside from the functional requirements clearly visible to users of the solution, there are nonfunctional requirements that must be supported.

In some embodiments, the system will include Privacy and Security. In some embodiments, data entered into the system is personal/private. In some embodiments, only authorized individuals will be allowed access to such data. In some embodiments, the data and systems are designed to prevent unauthorized access to the data. In some embodiments, for example, Medical Experts will not know the personally identifying information about the individuals for which the information about medical condition is sought. In some embodiments, they wouldn't have access to the database of such users—only the particular aspects of the conditions for which they are matching information.

In some embodiments, access to privileged users will be limited—so that such individuals would not have access to data they aren't authorized to access. In some embodiments, no personally identifiable information will be given to 3rd parties without user consent.

In some embodiments, protection against malicious access to the data would be maintained by firewalls, database encryption, OS patch levels, and other protections as deemed necessary. In some embodiments, the privacy and security will be periodically reviewed and updated.

In some embodiments, the system will operate at least 99% of the time. In some embodiments, any outage is reported publicly and explained to the End Users with an appropriate apology. In some embodiments, Web redundancy is maintained—so that multiple servers host the same functionality and content and work collaboratively. In some embodiments, the environment is designed for the availability, to avoid many failure points and for Disaster recovery. In some embodiments, daily backups+transaction logs of user updates will be implemented. So that if a catastrophic failure occurs, it will be possible to use the daily backups+ the log of transactions to automatically reconstruct the data in the system.

In some embodiments, the system will include potentially millions of users and include hundreds of data feeds with tens to hundreds of thousands of items in the overall feeds over time. In some embodiments, the system is designed to scale to such needs without rearchitecting it/rewriting it. In some embodiments, individual services will be stateless and broken down to small enough services that their logic could be spread across multiple physical machines/servers.

In some embodiments, the system will comply with pertinent regulations such as the Health Insurance Portability and Accountability Act ("HIPAA").

In some embodiments, an information item may be provided directly to a medical professional. In some embodiments, an information item may be provided directly to a medical professional responsible, at least in part, for caring for a user. In some embodiments, an information item may be provided directly to a medical professional with personal information related to a user removed to comply with pertinent regulations such as HIPAA.

In some embodiments, the system is an operational live system. In some embodiments, the system learns about its performance and improves over time. In some embodiments, the system can be designed to diagnose failure and events leading up to failure to prevent them from occurring. In some embodiments, logging of many activities and system status (memory, storage, network resources, etc.) is conducted.

In some embodiments, maintenance of the system includes, but is not limited to, upgrading of software. Software upgrades could be partial and only affected components are changed. In some embodiments, A-B testing is supported—different versions of components live in parallel and exposed to different end users based on a variety of criteria (including random and percentage).

In some embodiments, discrete logging and comparison will allow one to distinguish between results of each of the solutions. In some embodiments, ability to see conversion and process in a graphical form should be possible through such tools as Google Analytics, for instance.

In some embodiments, the system may be support multiple geographies, locales, and languages. In some embodiments, the information item is separated into different geographies based on local laws and/or regulations. In some embodiments, the information item may be classified based on geographic information. In some embodiments, the information item may be determined to be relevant to a user based on the user's geographic location and/or the local laws/regulations in the geographic location.

In some embodiments, the text fields are presented in any language. In some embodiments, the static resources such as screen graphics and texts would be stored in a way that a different language front end could be applied based on client preference (a preference of the user set at their configuration preference or implied/inferred from their login information).

In some embodiments, the system development would be managed in a configuration management system that allows distributed users to enter and manage configuration and software and system artifacts.

In some embodiments, the system may include a B2B ecommerce connection with the journal, to bill/charge the end user, collect payment, and distribute funds to the journal/publication.

In some embodiments, the system would include a medical referrals program. In some embodiments, the system may include B2B partners the require reporting/analytics to support their business.

While a number of embodiments of the present invention have been described, it is understood that these embodiments are illustrative only, and not restrictive, and that many modifications may become apparent to those of ordinary skill in the art. Also, the various steps of any method described herein may be carried out in any desired order (and any desired steps may be added and/or any desired steps may be eliminated).

What is claimed is:

1. A computer-implemented method, comprising:
    operating, by at least one specially programmed server, at least one medical information electronic portal, wherein the at least one specially programmed server comprises:
    specialized software, being:
        executed by the at least one specially programmed server, and
        at least partially stored in a non-transient computer medium accessed by the at least one specially programmed server, and at least one dedicated database for storing data accessed through the at least one medical information electronic portal;

causing, by the specially programmed server, via a computer network, to display at least one first graphical user interface associated with the at least one medical information electronic portal on a screen of each computing device of each user of a plurality of users which are concurrently interacting with the at least one medical information electronic portal,
  wherein the at least one first graphical user interface is configured to allow each user of the plurality of users to submit user profile data to the at least one specially programmed server, and
  wherein the user profile data of each user of the plurality of users comprise:
    i) demographic data of each user of the plurality of users, wherein the demographic data of each user comprise at least one geographic locale associated with such user, and
    ii) user-specific medical data of each user of the plurality of users, wherein the user-specific medical data comprise user-specific medical condition information about at least one medical condition of such user;

electronically receiving, by the at least one specially programmed server, via the computer network, the user profile data of each user of the plurality of users, utilizing the at least one first graphical user interface associated with the at least one medical information electronic portal;

electronically receiving, by the at least one specially programmed server, via the computer network, at least one set of medical advice rules, wherein the at least one set of medical advice rules are related to the at least one medical condition of each user of the plurality of users;

electronically receiving, in real-time, by the at least one specially programmed server, via the computer network, current third party data from a plurality of data feeds originated from a plurality of other distinct computer systems,
  wherein the plurality of data feeds comprises one or more of:
    i) a plurality of Rich Site Summary (RSS) feeds, and
    ii) a plurality of non-RSS feeds;
  wherein the plurality of other computer systems comprises one or more of:
    i) at least one of a plurality of health metadata sources,
    ii) at least one of a plurality dynamic data feeds,
    iii) at least one of a plurality of electronic medical records sources, and
    iv) at least one of a plurality of social media sources;
  wherein the current third party data comprises a plurality of informational items of current other medical data which are distinct from the user-specific medical data of at least one particular user of the plurality of users;

automatically determining, in real-time, for the at least one particular user of the plurality of users, by the at least one specially programmed server, a set of user-specific personalized medical condition-related characteristics based, at least in part, on the user-specific profile data of the at least one particular user of the plurality of users;

automatically identifying, in real-time, by the at least one specially programmed server, from the plurality of informational items of the current other medical data, a first set of current user-personalized informational items for the at least one particular user of the plurality of users, based, at least in part, on one or more of:
  i) the set of user-specific personalized medical condition-related characteristics, and
  ii) the pre-determined set of medical advice rules related to the at least one medical condition;

automatically determining, in real-time, by the at least one specially programmed server, a current relevance ranking for the first set of current user-personalized information items to be displayed to the at least one particular user of the plurality of users, wherein the current relevance ranking is, based, at least in part, on:
  i) the set of user-specific personalized medical condition-related characteristics, and
  ii) the pre-determined set of medical advice rules related to the at least one medical condition of the at least one user;

causing, by the at least one specially programmed server, via the computer network, to display the first set of current user-personalized information items on at least one second graphical user interface associated with the at least one medical information electronic portal on a screen of at least one first computing device associated with the at least one particular user of the plurality of users, wherein the at least one second graphical user interface is configured to present the first set of current user-personalized information items in accordance with the current relevance ranking;

tracking, in real-time, by the at least one specially programmed server, on-line activity of a subset of particular users of the plurality of users with respect to each information item of the first set of current user-personalized information items, wherein the subset of particular users comprises the at least one particular user and at least one other user to whom at least one information item of the first set of current user-personalized information items has been shown;

generating, by the at least one specially programmed server, a plurality of item-specific relevancy clues based, at least in part on the tracked on-line activity of the subset of particular users with respect to the first set of current user-personalized information items;

storing, in real-time, by the at least one specially programmed server, the plurality of item-specific relevancy clues for each information item of the first set of current user-personalized information items in the at least one dedicated database;

performing, based on the plurality of item-specific relevancy clues, in real-time, by the at least one specially programmed server, at least one of:
i) removing a particular information item from the first set of current user-personalized information items which is displayed, via the at least one second graphical user interface associated with the at least one medical information electronic portal, on the screen of the at least one first computing device associated with the at least one particular user of the plurality of users;
ii) updating the current relevant ranking to determine an updated relevance ranking and, then, displaying, in accordance with the updated relevance ranking, the first set of current user-personalized information items, via the at least one second graphical user interface associated with the at least one medical information electronic portal, on the screen of the at least one first computing device associated with the at least one particular user of the plurality of users;

iii) removing the particular information item from at least one second set of current user-personalized information items which is displayed, via the at least one second graphical user interface associated with the at least one medical information electronic portal, on a screen of at least one second computing device associated with at least one other user of the plurality of users; and iv) updating the current relevant ranking to determine the updated relevance ranking and, then, displaying, in accordance with the updated relevance ranking, the at least one second set of current user-personalized information items, via the at least one second graphical user interface associated with the at least one medical information electronic portal, on the screen of the at least one second computing device associated with the at least one other user of the plurality of users; and wherein the at least one specially programmed server has been programmed to be capable of performing at least all of the i-iv functions.

2. The computer-implemented method of claim 1, further comprising:

comparing, by the at least one specially programmed server, the first set of current user-personalized information items to a set of past user-personalized information items to identify that at least one obsolete information item; and notifying, by the at least one specially programmed server, the at least one particular user regarding the at least one obsolete information item.

3. The computer-implemented method of claim 1, wherein each information item the first set of current user-personalized information items corresponds to at least one type of information selected from the group consisting of: an electronic social media posting of others, an article, a clinical trial information item, a crowdsourced information item based on activity of others, and any combination thereof.

4. The computer-implemented method of claim 1, wherein the at least one set of medical advice rules are based, at least in part, on a type of a medical test, treatment costs, a status of a clinical trial, a type of available alternative treatment, a side effect, and any combination thereof.

5. The computer-implemented method of claim 1, wherein the set of user-specific personalized medical condition-related characteristics are selected from the group of:
i) a user-specific demographic criterion,
ii) a user-specific health condition criterion, and
iii) a user-specific medical treatment criterion.

6. The computer-implemented method of claim 1, wherein the method further comprises:

classifying, in real-time, by the at least one specially programmed server, the plurality of informational items of the current other medical data in accordance at least one classification determined by the at least one medical advice expert;

determining, in real-time, by the at least one specially programmed server, a plurality of relationships between the plurality of informational items of the current other medical data based, at least in part, on the classifying; and wherein the automatically identifying is further based on:
iii) the plurality of relationships between the plurality of informational items of the current other medical data.

7. The computer-implemented method of claim 1, further comprising:

causing, by the at least one specially programmed server, via the computer network, to display at least one third graphical user interface associated with the at least one medical information electronic portal on a screen of at least one second computing device associated with at least one medical expert; and wherein the at least one third graphic al user interface is configured to allow the at least one medical expert to identify the at least one set of medical advice rules to the at least one specially programmed server.

8. A specifically programmed computer system, comprising:

at least one specialized computer machine, comprising:
a non-transient memory having at least one region for at least partially storing particular computer executable program code; and
at least one processor for executing the particular program code stored in the non-transient memory, wherein the particular program code is configured to at least perform the following operations upon the execution:

operating at least one medical information electronic portal;

causing, via a computer network, to display at least one first graphical user interface associated with the at least one medical information electronic portal on a screen of each computing device of each user of a plurality of users which are concurrently interacting with the at least one medical information electronic portal, wherein the at least one first graphical user interface is configured to allow each user of the plurality of users to submit user profile data to the specially programmed computer system, and wherein the user profile data of each user of the plurality of users comprise:
i) demographic data of each user of the plurality of users, wherein the demographic data of each user comprise at least one geographic locale associated with such user, and
ii) user-specific medical data of each user of the plurality of users, wherein the user-specific medical data comprise user-specific medical condition information about at least one medical condition of such user;

electronic ally receiving, via the computer network, the user profile data of each user of the plurality of users, utilizing the at least one first graphical user interface associated with the at least one medical information electronic portal;

electronically receiving, via the computer network, at least one set of medical advice rules, wherein the at least one set of medical advice rules are related to the at least one medical condition of at least one user of the plurality of users;

electronically receiving, in real-time, via the computer network, current third party data from a plurality of data feeds originated from a plurality of other distinct computer systems, wherein the plurality of data feeds comprises one or more of:
i) a plurality of Rich Site Summary (RSS) feeds, and
ii) a plurality of non-RSS feeds;

wherein the plurality of other computer systems comprises one or more of:
i) at least one of a plurality of health metadata sources, ii) at least one of a plurality dynamic data feeds,
iii) at least one of a plurality of electronic medical records sources, and
iv) at least one of a plurality of social media sources;
wherein the current third party data comprises a plurality of informational items of current other medical data which are distinct from the user-specific medical data of at least one particular user of the plurality of users;
automatically determining, in real-time, for the at least one particular user of the plurality of users, a set of user-specific personalized medical condition-related characteristics based, at least in part, on the user-specific profile data of the at least one particular user of the plurality of users;
automatically identifying, in real-time, from the plurality of informational items of the current other medical data, a first set of current user-personalized informational items for the at least one particular user of the plurality of users, based, at least in part, on one or more of:
  i) the set of user-specific personalized medical condition-related characteristics, and
  ii) the pre-determined set of medical advice rules related to the at least one medical condition;
automatically determining, in real-time, a current relevance ranking for the first set of current user-personalized information items to be displayed to the at least one particular user of the plurality of users, wherein the current relevance ranking is, based, at least in part, on:
  i) the set of user-specific personalized medical condition-related characteristics, and
  ii) the pre-determined set of medical advice rules related to the at least one medical condition of the at least one user;
causing, via the computer network, to display the first set of current user-personalized information items on at least one second graphical user interface associated with the at least one medical information electronic portal on a screen of at least one first computing device associated with the at least one particular user of the plurality of users, wherein the at least one second graphic al user interface is configured to present the first set of current user-personalized information items in accordance with the current relevance ranking;
tracking, in real-time, on-line activity of a subset of particular users of the plurality of users with respect to the first set of current user-personalized information items, wherein the subset of particular users comprises the at least one particular user and at least one other user to whom the at least one information item of the first set of current user-personalized information items has been shown;
generating a plurality of item-specific relevancy clues based, at least in part on the tracked on-line activity of the subset of particular users with respect to the first set of current user-personalized information items;
storing, in real-time, the plurality of item-specific relevancy clues for each information item of the first set of current user-personalized information items in the at least one dedicated database;
performing, based on the plurality of item-specific relevancy clues, in real-time, at least one of:
i) removing a particular information item from the first set of current user-personalized information items which is displayed, via the at least one second graphical user interface associated with the at least one medical information electronic portal, on the screen of the at least one first computing device associated with the at least one particular user of the plurality of users;
ii) updating the current relevant ranking to determine an updated relevance ranking and, then, displaying, in accordance with the updated relevance ranking, the first set of current user-personalized information items, via the at least one second graphical user interface associated with the at least one medical information electronic portal, on the screen of the at least one first computing device associated with the at least one particular user of the plurality of users;
iii) removing the particular information item from at least one second set of current user-personalized information items which is displayed, via the at least one second graphical user interface associated with the at least one medical information electronic portal, on a screen of at least one second computing device associated with at least one other user of the plurality of users; and
iv) updating the current relevant ranking to determine the updated relevance ranking and, then, displaying, in accordance with the updated relevance ranking, the at least one second set of current user-personalized information items, via the at least one second graphic al user interface associated with the at least one medical information electronic portal, on the screen of the at least one second computing device associated with the at least one other user of the plurality of users; and
wherein the particular program code is configured to be capable of performing at least all of the i-iv functions.

9. The specifically programmed computer system of claim 8, wherein the particular program code is further configured to at least perform the following operations upon the execution:
comparing the first set of current user-personalized information items to a set of past user-personalized information items to identify that at least one obsolete information item; and
notifying the at least one particular user regarding the at least one obsolete information item.

10. The specifically programmed computer system of claim 8, wherein each information item the first set of current user-personalized information items corresponds to at least one type of information selected from the group consisting of: an electronic social media posting of others, an article, a clinical trial information item, a crowdsourced information item based on activity of others, and any combination thereof.

11. The specifically programmed computer system of claim 8, wherein the at least one set of medical advice rules are based, at least in part, on a type of a medical test, treatment costs, a status of a clinical trial, a type of available alternative treatment, a side effect, and any combination thereof.

12. The specifically programmed computer system of claim 8, wherein the set of user-specific personalized medical condition-related characteristics are selected from the group of:
  i) a user-specific demographic criterion,
  ii) a user-specific health condition criterion, and
  iii) a user-specific medical treatment criterion.

13. The specifically programmed computer system of claim 8, wherein the particular program code is further configured to at least perform the following operations upon the execution:

classifying, in real-time, the plurality of informational items of the current other medical data in accordance at least one classification determined by the at least one medical advice expert;

determining, in real-time, a plurality of relationships between the plurality of informational items of the current other medical data based, at least in part, on the classifying; and wherein the automatically identifying is further based on:
iii) the plurality of relationships between the plurality of informational items of the current other medical data.

14. The specifically programmed computer system of claim 8, wherein the particular program code is further configured to at least perform the following operations upon the execution:

causing, via the computer network, to display at least one third graphical user interface associated with the at least one medical information electronic portal on a screen of at least one second computing device associated with at least one medical expert; and wherein the at least one third graphical user interface is configured to allow the at least one medical expert to identify the at least one set of medical advice rules to the specially programmed computer system.

* * * * *